United States Patent [19]

Sunagawa et al.

[11] Patent Number: 4,742,052

[45] Date of Patent: May 3, 1988

[54] ANTIBACTERIAL β-LACTAM COMPOUNDS

[75] Inventors: Makoto Sunagawa; Haruki Matsumura, both of Osaka; Takaaki Inoue; Masao Enomoto, both of Hyogo, all of Japan

[73] Assignee: Sumitomo Pharmaceuticals Company, Limited, Osaka, Japan

[21] Appl. No.: 398,489

[22] Filed: Jul. 15, 1982

[30] Foreign Application Priority Data

| Jul. 15, 1981 | [JP] | Japan | 56-111108 |
| Dec. 1, 1981 | [JP] | Japan | 56-193947 |
| Dec. 3, 1981 | [JP] | Japan | 56-195470 |
| Dec. 4, 1981 | [JP] | Japan | 56-196037 |
| Dec. 28, 1981 | [JP] | Japan | 56-211416 |

[51] Int. Cl.⁴ .................. A61K 31/43; C07D 499/00
[52] U.S. Cl. .................................. 514/195; 514/192; 514/197; 540/310; 546/198; 546/270

[58] Field of Search ............... 260/245.2 R, 245.2 T; 426/270; 540/310; 514/195, 197, 192

[56] References Cited

U.S. PATENT DOCUMENTS 4,260,618  4/1981  Christensen et al. ........ 260/245.2 R Primary Examiner—Richard A. Schwartz
Attorney, Agent, or Firm—Sughrue, Mion, Zinn, Macpeak, and Seas

[57] ABSTRACT

Novel β-lactam compounds classified into penem compounds, a process for preparing the same and use of such β-lactam compounds are disclosed. These β-lactam compounds exhibit excellent antimicrobial activities useful as pharmaceuticals or they are important intermediates for the synthesis of compounds having antimicrobial activities.

16 Claims, No Drawings

ANTIBACTERIAL β-LACTAM COMPOUNDS

The present invention relates to novel penem compounds, a process for preparing the same and use of such penem compounds.

The novel penem compounds according to this invention are represented by the formula:

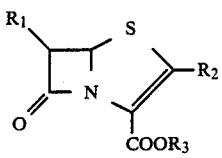

[I]

wherein:

$R_1$ is hydrogen, 1-hydroxyethyl or a protected 1-hydroxyethyl in which the hydroxyl group is protected by a conventional protecting group for a hydroxyl group, $R_2$ is a group of the following formulae (1) to (12):

$$-S(CH_2)_nC(CH_3)_2(CH_2)_mNHR_4 \quad (1)$$

wherein $R_4$ is hydrogen or a conventional protecting group for an amino group, and each of n and m is 0, 1, 2, 3 or 4;

$$-(CH_2)_nC(CH_3)_2(CH_2)_mNHR_4 \quad (2)$$

wherein $R_4$, n and m are as defined above;

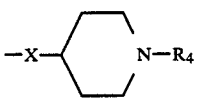

(3)

wherein $R_4$ is as defined above, and X is a group of the formula: $-(CH_2)_l-$, $-S(CH_2)_l-$, $-CH_2S-$, $-CH=CH-$ or $-C(CH_3)=CH-$ wherein l is 0, 1 or 2;

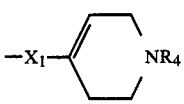

(4)

wherein $R_4$ is as defined above, and $X_1$ is a group of the formula: $-CH=CH-$ or $-SCH_2-$;

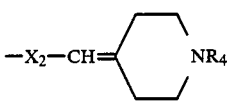

(5)

wherein $R_4$ is as defined above, and $X_2$ is a chemical bond (a direct linkage) or a group of the formula: $-SCH_2-$;

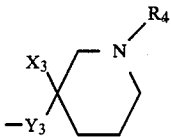

(6)

wherein $R_4$ is as defined above, $X_3$ is hydrogen, and $Y_3$ is a methylene group ($-CH_2-$), or $X_3$ and $Y_3$ may be linked together to form a methylinilydene group ($-CH=$);

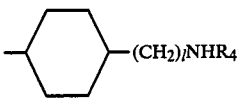

(7)

wherein $R_4$ and l are as defined above;

$$-CH=CH-(CH_2)_{n'}NHR_4 \quad (8)$$

wherein $R_4$ is as defined above and n' is 1 or 2;

$$-CH=CH-C(CH_3)_2-(CH_2)_{n'}-NHR_4 \quad (9)$$

wherein $R_4$ is n' are as defined above;

$$-CH=CH-COOR_3 \quad (10)$$

wherein $R_3$ is hydrogen or a conventional protecting group for a carboxyl group;

$$-(CH_2)_{m'}-COOR_3 \quad (11)$$

wherein $R_3$ is as defined above, and m' is 2 or 3; and

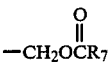

(12)

wherein $R_7$ is (a) a $C_1$-$C_4$ alkyl group substituted with $C_1$-$C_4$ alkoxy, $C_1$-$C_4$ alkylcarbonyloxy, hydroxy or a hydroxy group protected by a conventional protecting group for a hydroxy group, or (b) a group of the formula: $-CH_2CH_2NHR_4$ or

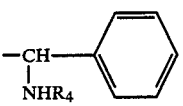

wherein $R_4$ is as defined above; or $R_2$ is an aryl group, cyclohexyl, cyclohexylthio, 4-hydroxymethylcyclohexyl or 4-hydroxymethylcyclohexyl in which the hydroxy group is protected by a conventional protecting group for a hydroxy group; and $R_3$ is hydrogen or a conventional protecting group for a carboxyl group.

The term "conventional protecting group for a hydroxy group" as used herein for the protected 1-hydroxyethyl of $R_1$ and $R_1'$, 4-hydroxymethylcyclohexyl of $R_2$, and hydroxy of $R_7$, Z and Z' includes, for example, a $C_1$-$C_4$ alkoxy carbonyl group such as tert-butyloxycarbonyl, a $C_1$-$C_4$ halogenoalkoxycarbonyl group such as 2-iodoethyloxycarbonyl and 2,2,2-trichloroethyloxycarbonyl, an aralkyloxycarbonyl group such as benzyloxycarbonyl, p-methoxybenzyloxycarbonyl, o-nitrobenzyloxycarbonyl and p-nitrobenzyloxycarbonyl, a tri($C_1$-$C_4$)alkylsilyl group such as tert-butyldimethylsilyl and trimethylsilyl, a $C_4$-$C_{10}$ tert-alkyl group such as tert-butyl, a substituted or unsubstituted mono, di- or tri-phenylmethyl group such as benzyl, p-methoxybenzyl, diphenylmethyl, di(p-anisyl)methyl and trityl.

Examples of the groups of the formulae (1) to (6) for $R_2$ are as follows:

(1)
—S(CH$_2$)$_n$C(CH$_3$)$_2$(CH$_2$)$_m$NHR$_4$
—S(CH$_2$)$_3$C(CH$_3$)$_2$NHR$_4$,
—S(CH$_2$)$_2$C(CH$_3$)$_2$CH$_2$NHR$_4$,
—S(CH$_2$)$_2$C(CH$_3$)$_2$NHR$_4$,
—SCH$_2$C(CH$_3$)$_2$NHR$_4$,
—SCH$_2$C(CH$_3$)$_2$CH$_2$NHR$_4$,
—SCH$_2$C(CH$_3$)$_2$CH$_2$CH$_2$NHR$_4$,
—S(CH$_2$)$_2$C(CH$_3$)$_2$(CH$_2$)$_2$NHR$_4$,
—S(CH$_2$)$_2$C(CH$_3$)$_2$(CH$_2$)$_3$NHR$_4$, etc.

(2)
—(CH$_2$)$_n$C(CH$_3$)$_2$(CH$_2$)$_m$NHR$_4$
—CH$_2$C(CH$_3$)$_2$CH$_2$NHR$_4$,
—CH$_2$C(CH$_3$)$_2$NHR$_4$,
—CH$_2$CH$_2$C(CH$_3$)$_2$NHR$_4$,
—CH$_2$CH$_2$C(CH$_3$)$_2$CH$_2$NHR$_4$,
—CH$_2$CH$_2$CH$_2$C(CH$_3$)$_2$NHR$_4$,
—CH$_2$CH$_2$CH$_2$C(CH$_3$)$_2$CH$_2$NHR$_4$,
—CH$_2$C(CH$_3$)$_2$CH$_2$CH$_2$NHR$_4$,
—CH$_2$C(CH$_3$)$_2$CH$_2$CH$_2$CH$_2$NHR$_4$, etc.

(3)

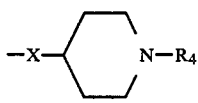

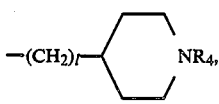

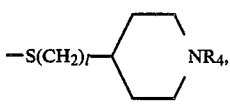

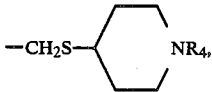

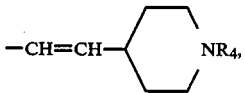

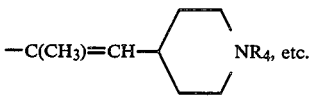

(4)

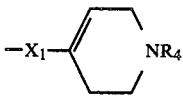

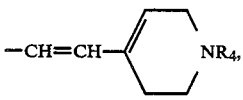

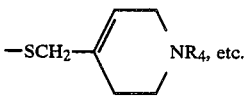

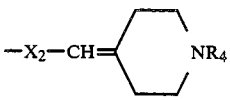

(5)

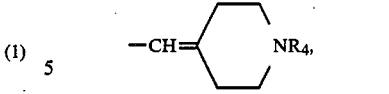

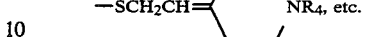

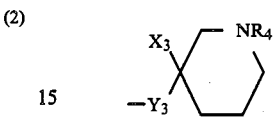

(6)

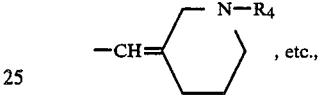

wherein n, m, $R^4$, X, $X_1$, $X_2$, $X_3$ and $Y_3$ are as defined above.

Examples of $R_4$ include hydrogen, a $C_1$–$C_4$ alkoxycarbonyl group such as tert-butyloxycarbonyl, a $C_1$–$C_4$ halogenoalkoxycarbonyl group such as 2-iodoethyloxycarbonyl and 2,2,2-trichloroethyloxycarbonyl, an aralkyloxycarbonyl such as benzyloxycarbonyl, p-methoxybenzyloxycarbonyl, o-nitrobenzyloxycarbonyl and p-nitrobenzyloxycarbonyl, a tri($C_1$–$C_4$)alkylsilyl group such as tert-butyldimethylsilyl and trimethylsilyl, a $C_4$–$C_{10}$ tert-alkyl group such as tert-butyl and a substituted or unsubstituted mono-, di- or triphenylmethyl group such as benzyl, p-methoxybenzyl, diphenylmethyl, di-(p-anisyl)methyl and trityl.

Examples of the aryl group for $R_2$ are the groups of the formula:

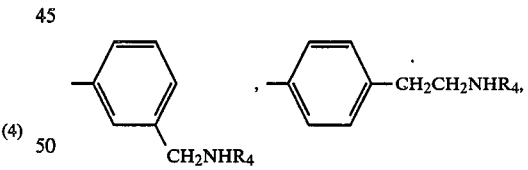

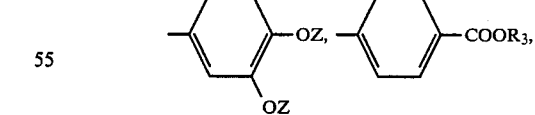

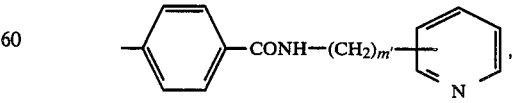

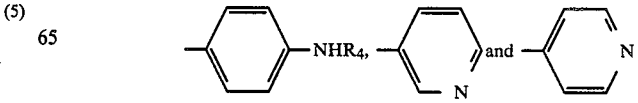

wherein $R_4$, $R_3$ and $m'$ are as defined above, and Z is hydrogen or a conventional protecting group for a hydroxyl group.

Examples of the group $R_3$ are hydrogen, a $C_1$–$C_4$ straight or branched chain alkyl group such as methyl, ethyl, iso-propyl and tert-butyl, a $C_1$–$C_4$ halogenoalkyl group such as 2-iodoethyl and 2,2,2-trichloroethyl, a $C_1$–$C_4$ alkoxymethyl group such as methoxymethyl, ethoxymethyl and iso-butoxymethyl, a $C_1$–$C_4$ alkylcarbonyloxymethyl group such as acetoxymethyl, propionyloxymethyl, butylyloxymethyl and pivaloyloxymethyl, a 1-($C_1$–$C_4$)alkyloxycarbonyloxyethyl group such as 1-methoxycarbonyloxyethyl and 1-ethoxycarbonyloxyethyl, an arylmethyl group such as benzyl, p-methoxybenzyl, o-nitrobenzyl and p-nitrobenzyl, benzhydryl, phthalidyl and a tri($C_1$–$C_4$)alkylsilyl group such as trimethylsilyl and tert-butyldimethylsilyl.

The carboxylic acid compound ($R_3$=H) of the penem compound of the formula [I] can form salts such as inorganic metal salts (e.g. lithium, sodium, potassium, calcium, magnesium, etc.) or ammonium salts (e.g. ammonium, cyclohexyl ammonium, diisopropyl ammonium, triethyl ammonium, etc.). Of these salts, sodium and potassium salts are preferred.

The β-lactam compounds represented by the formula [I] of the present invention are classified into penem derivatives and are novel compounds having a wide variety of substituents at the 2-position thereof. These β-lactam compounds exhibit excellent antimicrobial activities and therefore are useful as pharmaceutical agents, or they are important intermediates for the synthesis of useful compounds having antimicrobial activities.

The novel β-lactam compounds represented by the formula [I] of the present invention exhibit excellent antimicrobial activities against various pathogenic organisms including Gram-positive bacteria such as *Staphylococcus aureus*, *Staphylococcus epidermidis*, *Streptococcus pyogenes*, *Streptococcus faecalis* and the like, and Gram-negative bacteria such as *Escherichia coli*, *Proteus mirabilis*, *Serratia marcescens*, *Pseudomonas aeruginosa* and the like, and are useful compounds as antimicrobial agents as well as intermediates for preparing compounds having antimicrobial agents.

The compounds of the present invention can be used for treatment and prevention of various bacterial infections as antibacterial agents in the dosage forms suitable for oral administration, for example, tablets, capsules, powders, syrup, etc., or parenteral administrations such as intravenous and intramuscular injections or intrarectral administration. The dose level varies depending upon the severity of conditions to be treated, age and body weight of patients, dosage forms and number of administrations per day (single or multiple doses), but, generally, the compounds can be administered at a dose of about 200 to about 3000 mg per day in a single dose or multiple doses for adult human. Of course, the dose level can be decreased or increased, if necessary.

Among the penem compounds [I] of the present invention, the penem compounds of the formula:

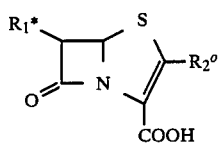

[I-A]

wherein $R_1^*$ is hydrogen or 1-hydroxyethyl, and $R_2^0$ is the group of the formula;

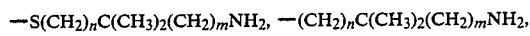

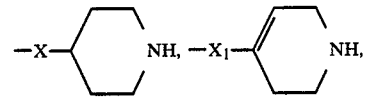

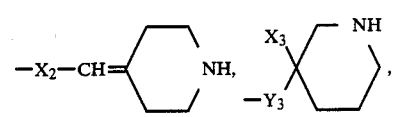

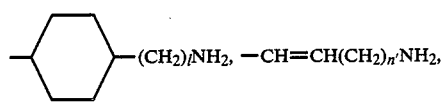

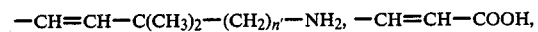

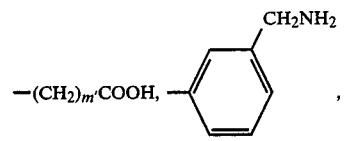

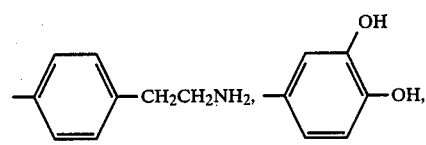

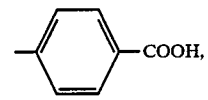

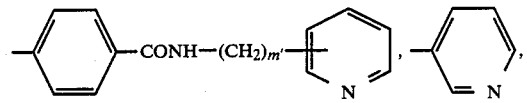

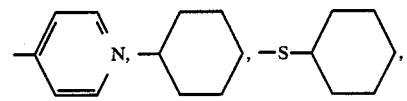

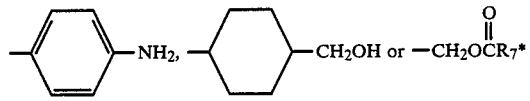

wherein n, m, l, n', m', X, $X_1$, $X_2$, $X_3$ and $Y_3$ are as defined above, $R_7^*$ is (a) a $C_1$–$C_4$ alkyl group substituted with $C_1$–$C_4$ alkoxy, $C_1$–$C_4$ alkylcarbonyloxy or hydroxy group, or (b) 2-aminoethyl or 1-amino-1-phenylmethyl, or non-toxic salts thereof are preferred.

Particularly preferred penem compounds are those having the formula:

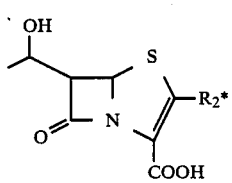

wherein R$_2$* is the group of the formula:

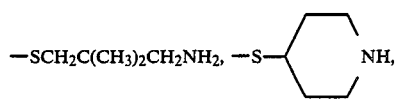
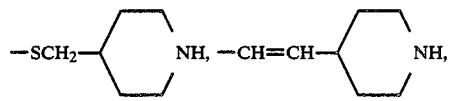
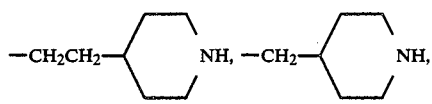
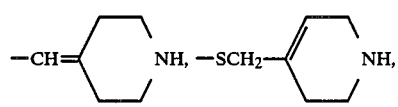
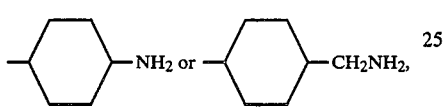

or non-toxic salts thereof.

The compound of the formula [I] contains an asymmetrical carbon atom in the structure and, therefore, may exist in optical isomers and steric isomers. Such isomers are represented herein by a single chemical structure for simplicity, but it should be noted that the present invention includes within its scope these each isomers as well as a racemic mixture thereof. However, the compounds having the same C$_5$-configuration as that of penicillin compounds, i.e., 5-R configuration, can be selected as preferred compounds.

Of the compounds of the formula [I], the steric configuration is now described hereinafter more specifically with respect to the compounds of the formula [I-h]:

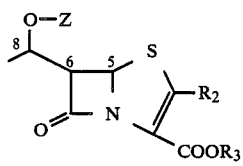

[I-h]

wherein R$_2$ and R$_3$ are as defined above and Z represents a hydrogen atom or a conventional protecting group for a hydroxy group. A preferred group of the compounds of the formula [I-h] is those having (5R, 6R, 8R) configuration, (5R, 6S, 8R) configuration, (5R, 6R, 8S) configuration, and (5R, 6S, 8S) configuration, with the most preferred compounds being those having (b 5R, 6R, 8R) and (5R, 6S, 8R) configurations.

The penem compounds [I] can be prepared by various methods, and typical examples of the methods are hereinafter described.

The penem compounds of the formula:

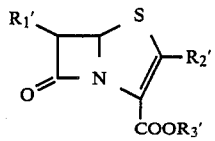

[I-a]

wherein:
R$_1'$ is hydrogen or a protected 1-hydroxyethyl group wherein the hydroxy group is protected with a conventional protecting group for a hydroxyl group;
R$_2'$ is a group of the formula:

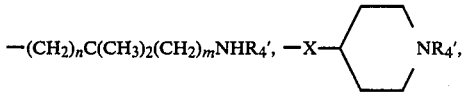

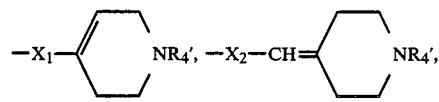

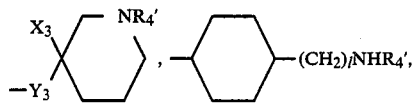

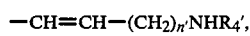

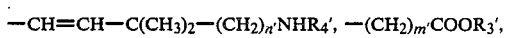

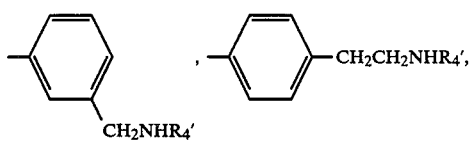

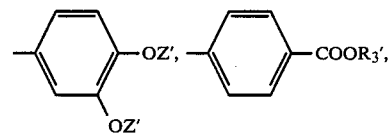

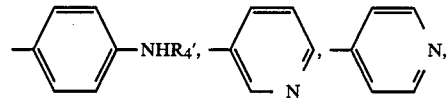

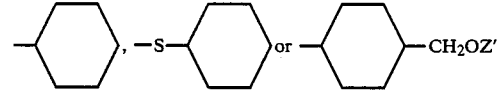

wherein n, m, l, n', m', X, X$_1$, X$_2$, X$_3$ and Y$_3$ are as defined above, R$_3'$ is a conventional protecting group for a carboxyl group, R$_4'$ is a conventional protecting group for an amino group and Z' is a conventional protecting group for a hydroxyl group, and
R$_3'$ represents a conventional protecting group for a carboxyl group, can be prepared by heating a β-lactam compound of the formula:

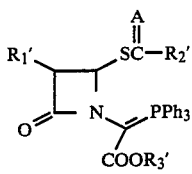

wherein $R_1'$, $R_2'$, $R_3'$ are as defined above, Ph represents a phenyl group and A is an oxygen atom or a sulfur atom, in an inert solvent.

The compounds of the formula [I-a] wherein $R_2'$ is a p-carboxyphenyl group can be prepared from a corresponding starting compound of the formula [II] by the procedure similar to that described above.

Examples of preferred inert solvents include an aromatic hydrocarbon such as benzene, toluene, xylene, o-xylene, etc. or a mixture thereof. If desired, an inert solvent such as an ether (e.g., dioxane, tetrahydrofuran, etc.), an aliphatic hydrocarbon (e.g. cyclohexane, etc.), a halogenated hydrocarbon (e.g. chloroform, 1,2-dichloroethane, etc.) may be used. The reaction temperature can be varied widely from 40° C. to 200° C.

The penum compounds of the formula:

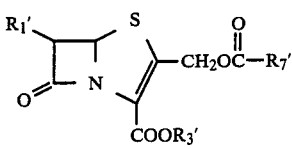

wherein $R_1'$ and $R_3'$ are defined above, $R_7'$ represents (1) a $C_1$–$C_4$ alkyl group substituted with $C_1$–$C_4$ alkoxy, $C_1$–$C_4$ alkylcarbonyloxy or hydroxy group protected with a usual protecting group for a hydroxy group or (2) the group of the formula:

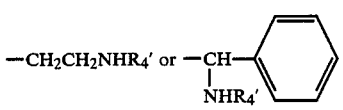

($R_4'$ is as defined above). can be prepared by reacting a penem compound of the formula:

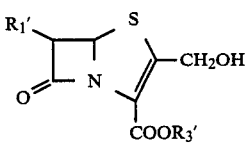

wherein $R_1'$ and $R_3'$ are as defined above, with a carboxylic acid or an active derivative thereof represented by the formula:

wherein $R_7'$ is as defined above.

The reaction can be accomplished by a conventional acylation method comprising the reaction between an alcohol derivative with a carboxylic acid compound or an active derivative thereof.

The reaction is preferably conducted by a direct acylation method comprising reacting an alcohol compound [I-c] with a carboxylic acid ($R_7'COOH$) in the presence of a convensional dehydration agent, or an active acid anhydride method comprising reacting an alcohol compound [I-c] with an active anhydride derivative of the carboxylic acid [$R_7'COOH$] such as the acid chloride, etc. in the presence of a base.

The compounds of the formula [I-c] wherein $R_1'$ is hydrogen can be prepared as disclosed in British Patent Application No. 49842/78 and the compounds of the formula [I-c] wherein $R_1'$ is a protected 1-hydroxyethyl can be prepared from the compounds of the formula [V-a] described below by the procedure as described in British Patent Application No. 49842/78.

The penem compounds of the formula:

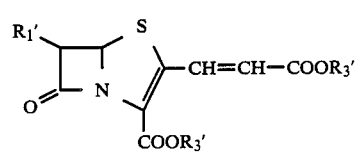

wherein $R_1'$ and $R_3'$ are as defined above, can be prepared by the Wittig-type reaction between the penem compound of the formula:

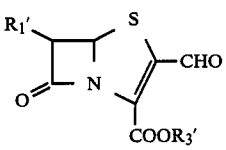

wherein $R_1'$ and $R_3'$ are as defined above, and the compounds of the formula;

wherein $R_3'$ is as defined above and Y represents phenyl or $C_1$–$C_4$ alkoxy such as methoxy and ethoxy, etc.

The starting aldehyde compound [I-e] can be prepared by oxidation of an alcohol compound [I-c].

The penem compound of the formula:

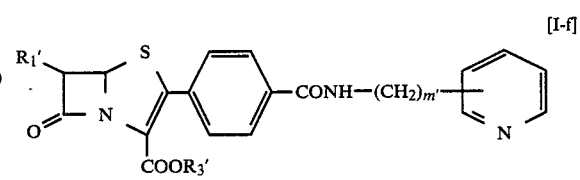

wherein $R_1'$, $R_3'$ and $m'$ are as defined above, can be prepared by dehydrating condensation of a carboxylic acid derivative of the formula:

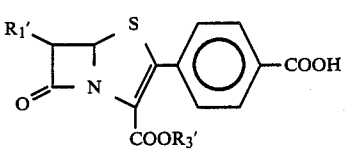

wherein $R_1'$ and $R_3'$ are defined above, and an amine of the formula;

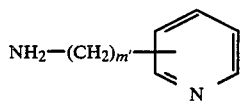

wherein m' is as defined above.

The reaction can be accomplished by a wide variety of acylating methods as conventionally employed for acylation of an amine with a carboxylic acid derivative.

The penem compound of the formula:

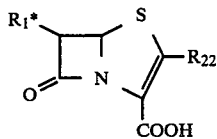

wherein:
$R_1^*$ is hydrogen or 1-hydroxyethyl,
$R_{22}$ represents the group of the formula:

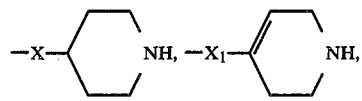

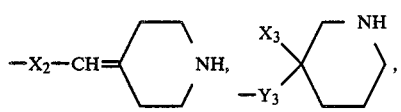

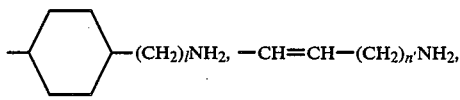

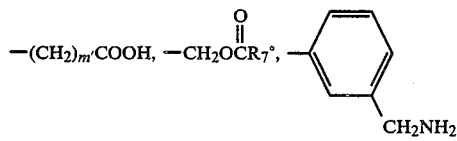

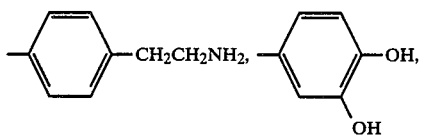

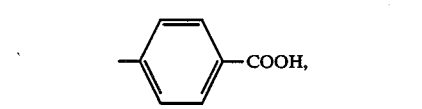

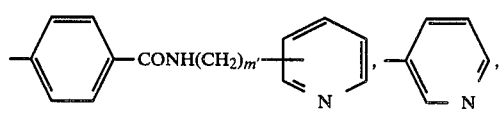

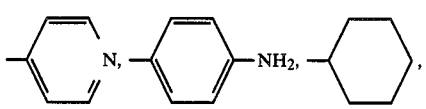

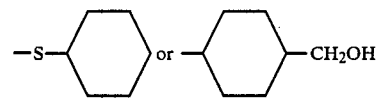

wherein n, m, l, m', X, $X_1$, $X_2$, $X_3$ and $Y_3$ are as defined above, $R_7^0$ is $C_1$–$C_4$ alkyl substituted with $C_1$–$C_4$ alkoxy, $C_1$–$C_4$ alkylcarbonyloxy or hydroxy, or $R_7^0$ is 2-aminoethyl or 1-amino-1-phenylmethyl; can be prepared by a conventional deprotecting reaction of the protecting group of carboxyl, hydroxyl and amino (i.e., $R_3'$, $R_4'$, $Z'$, etc.) from the compound [I-a], [I-b], [I-d] and [I-f].

The protecting group can be removed by any one of the procedures conventionally employed for deprotection of a protecting group of carboxylic acids, alcohols or amines. For example, the deprotection reaction can be accomplished by treatment of the penem compound with an acid such as trifluoroacetic acid, formic acid, boron trifluoride, aluminum chloride, etc. or a base such as sodium carbonate, potassium carbonate, sodium bicarbonate, sodium sulfide, tetrabutyl ammonium fluoride, etc.

Alternatively, the deprotection can be achieved by the reduction method such as catalytic hydrogenation, or the reduction using zinc-acetic acid, etc. The catalytic hydrogenation can be performed by reacting the compound [I-a], [I-b], [I-d] or [I-f] with $H_2$ in the presence of a catalyst such as Pd-C (palladium on carbon), PtO (platinum oxide), etc. in an inert solvent such as an alcohol (e.g., methanol, ethanol, etc.), an ether (e.g. tetrahydrofurane, dioxane, etc.), an aliphatic acid (e.g. acetic acid), water (water per se, aqueous phosphate buffer, etc.) or a mixture thereof. The hydrogenation can be conducted under atmospheric pressure or pressurized conditions and at a temperature varying from ice-cooling to about 40° C.

The penem compounds [I] of the present invention thus produced can be separated from the reaction mixture and purified by conventional procedures which are well known in the art.

The starting materials of the formula [II] used for the synthesis of the penem compounds [I] can be prepared, for example, according to the following scheme.

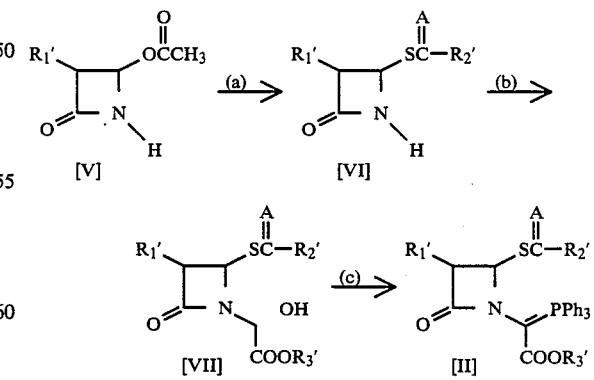

wherein $R_1'$ is hydrogen or 1-hydroxyethyl protected by a conventional protecting group for a hydroxy group, $R_2'$, $R_3'$ and A are as defined above. The conversion in each step can be achieved in the following manner.

(a) The compound [VI] can be obtained by reacting the acetate compound [V] with a compound of the formula:

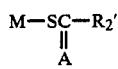   [VIII]

wherein $R_2'$ and A are as defined above, and M is an alkali metal atom such as lithium, sodium and potassium, in an inert solvent such as water, methanol, ethanol, n-propanol, iso-propanol, dioxane, tetrahydrofuran, diethyl ether or a mixture thereof (b) The hydroxy derivative [VII] can be prepared by reacting the compound [VI] with an ester derivative of glyoxylic acid in the presence or absence of an acid such as boron trifluoride, aluminum chloride, etc. or a base such as triethylamine, pyridine, 1,5-diazabicyclo[5,4,-0]undecene-5 (DBU), etc. in an inert solvent. Preferred examples of the inert solvents include an aromatic hydrocarbon such as benzene, toluene, etc., an ether such as tetrahydrofurane, dioxane, etc. The reaction temperature can be varied widely from ice-cooling to a refluxing temperature of the reaction system.

(c) The phosphorane derivative [II] can be prepared from the hydroxy derivative [VII] in two steps. The hydroxy compound [VII] can be first converted to a halide derivative thereof by treatment with a halogenating agent such as thionyl halide (thionyl chloride or thionyl bromide), phosphoryl chloride, phosphorus pentachloride, phosphorus tribromide, oxalyl chloride, etc. in the presence or absence of a base such as triethylamine, pyridine, lutidine, etc. in an inert solvent such as tetrahydrofran, dioxane, etc. The resulting halide derivative can then be converted into the corresponding phosphorane derivative [II] by treating the halide derivative with triphenyl phosphine and a base such as an organic base (e.g., triethylamine, pyridine, lutidine, etc.) or an inorganic base (e.g., NaHCO$_3$, Na$_2$CO$_3$, K$_2$CO$_3$, NaOH, etc.).

Some of the phosphorane derivative [II] can also be prepared by acylating a compound of the formula:

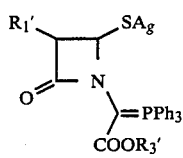

wherein $R_1'$ and $R_3'$ are as defined above, with the corresponding carboxylic acid or an active derivative thereof in the presence of a base.

The starting acetate compounds [V] can be prepared in the manner similar to the method disclosed in Japanese Patent Application (OPI) No. 153789/80 (the term "OPI" used herein refers to a published unexamined patent application). Alternatively, the acetate compounds [V-a] can be prepared easily according to the following novel synthetic route.

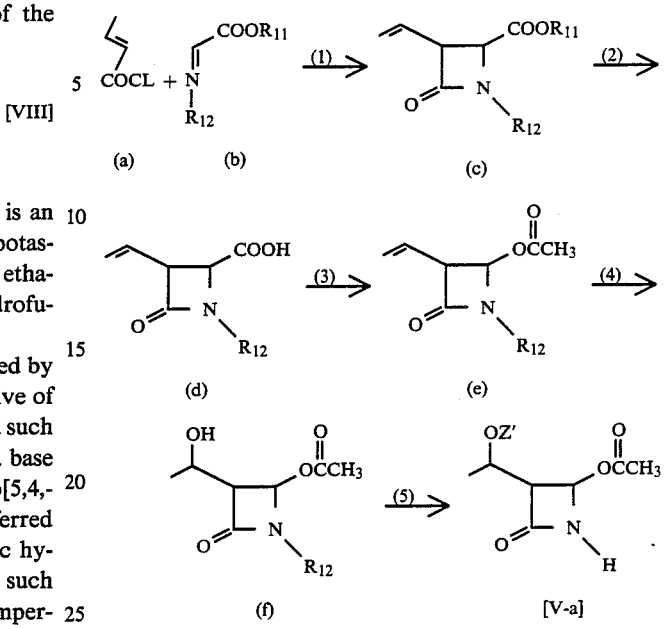

wherein $R_{11}$ is $C_1$-$C_4$ alkyl or aryl-($C_1$-$C_4$)alkyl, $R_{12}$ is substituted or unsubstituted mono- or diphenylmethyl such as p-methoxybenzyl, di(p-anisyl)methyl, diphenylmethyl, etc., and Z' is a conventional protecting group.

The conversion in each of the steps (1) to (5) can be achieved in the following manner.

(1) The β-lactam compound (c) can be prepared by reacting crotonoyl chloride with a Schiff base (which can be prepared from an ester derivative of glyoxylic acid and a corresponding primary amine in a conventional manner) in the presence of a base such as triethylamine, pyridine, lutidine, DBU, etc. in an inert solvent such as halogenated hydrocarbons (chloroform, methylene dichloride, etc.), aromatic hydrocarbons (benzene, toluene, etc.) ethers (diethyl ether, dioxane, tetrahydrofuran, etc.) or a mixture thereof. The temperature for the addition-cyclization reaction can be varied from 0° C. to 100° C., (2) The hydrolysis of the ester compound (c) to the corresponding acid (d) can be achieved in a manner as conventionally employed for hydrolysis of an ester to the corresponding carboxylic acid. The hydrolysis can be easily achieved using an alkali or an acid.

(3) The carboxylic acid (d) can be converted into the acetoxy compound (e) by oxidative decarboxylation with lead tetraacetate. The oxidative decarboxylation can be performed by treating the compound (d) with lead tetraacetate in an amount not less than 1 mole, preferably 1 to 3 moles, per mole of the carboxylic acid (d) in an inert solvent in the presence or absence of a base such as pyridine, lutidine, etc. or a salt such as sodium acetate, potassium acetate, etc.

Examples of suitable inert solvents are aromatic hydrocarbons such as benzene, toluene, etc., acetic acid, dimethylformamide, hexamethyl phospholic triamide, diethyl ether, tetrahydrofuran, dioxane or a mixture thereof.

The reaction temperature can be varied from 0° C. to 100° C.

(4) The hydroxyethyl compound (f) can be obtained by oxidizing the vinyl group of the acetoxy compound (e) with mercuric acetate and then reducing the oxidized derivative with reducing agent such as sodium borohydride in an inert solvent such as water, tetrahydrofuran, dioxane, diethyl ether, acetonitrile or a mixture thereof. The mercuric oxidation can be preferably achieved by reacting the acetoxy compound (e) with mercuric acetate in an amount of 1 to 2 moles per mole of the acetoxy compound at 0° to 100° C. The subsequent reductive demercuration can be carried out by reducing the resulting compound with sodium borohydride (0.25 to 5 molar amount) in the presence of an alkali metal hydroxide (preferably 0.5 to 5 molar amount) such as sodium hydroxide, etc. The optimum temperature for the reduction reaction can be varied from −10° C. to 40° C.

(5) The hydroxyethyl compound (f), for example, can be easily converted into a hydroxy-protected derivative thereof by using an acylating agent (e.g. p-nitrobenzyl chloroformate, etc.) in the presence of a base. The azetidinone compound [V-a] can be prepared by oxidation of the hydroxy-protected derivative described above with ceric ammonium nitrate in an amount of 2 to 4 moles per mole of the hydroxy-protected derivative in an inert solvent such as dimethylformamide, acetonitrile, tetrahydrofuran, dioxane, ethanol, water or a mixture thereof at 0° to 60° C.

The azetidinone derivative [V-a] can also be prepared according to the following scheme.

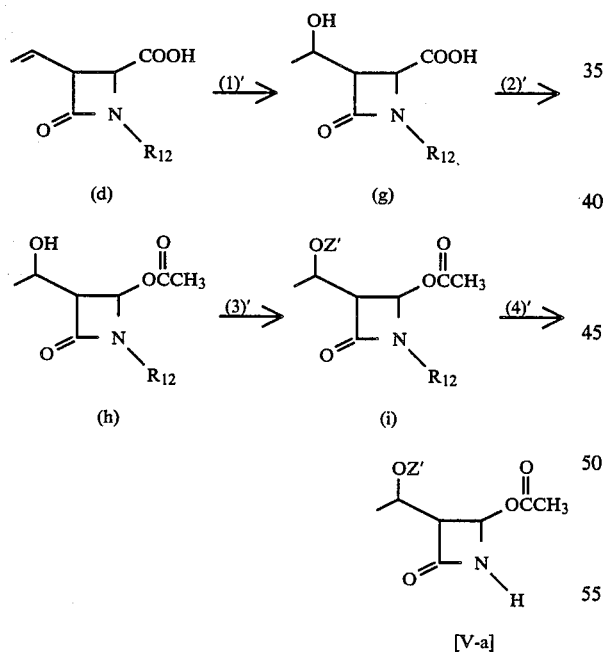

wherein $R_{12}$ and $Z'$ are as defined above.

The hydroxy-introducing reaction by oxymercuration (1)', the conversion reaction of carboxyl group to acetoxy group (2)', the protecting reaction of the hydroxy group (3)' and the elimination reaction of $R_{12}$ (4)' can be accomplished by the methods similar to those described above.

The azetidinone [V-a] can also be prepared according to the following scheme:

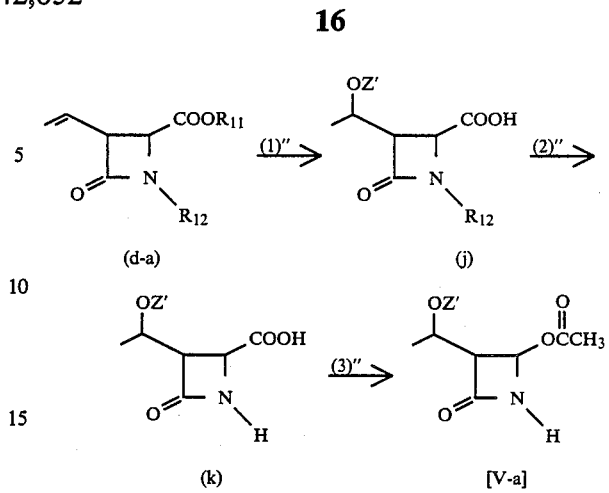

wherein $R_{11}$, $R_{12}$ and $Z'$ are as defined above.

The hydroxy-introducing reaction by oxymercuration, the hydroxy-protecting reaction and the elimination of a carboxyl-protecting group (1)". the oxidative elimination of N-substituent (2)" and the oxidative decarboxylation (3)" can be accomplished by the methods similar to those described above.

Each of the processes for preparing the β-lactam compounds of the formula [V-a] described above is a novel process. The β-lactam compounds of the formula [V-a] may exist in threo and erythro forms with respect to the steric configuration of hydroxy group in the protected hydroxyethyl group at the 3-position. The processes are characterized in that they are capable of producing the threo form with high selectivity.

Among the starting compounds of the formula [VIII], for example, the starting compound of the formula [VIII-a];

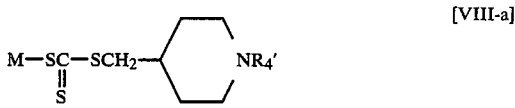

[VIII-a]

wherein M and $R_4'$ are as defined above, can be prepared by a conventional method such as treatment of a thiol compound of the formula;

[XI]

wherein $R_4'$ is as defined above, with carbon disulfide ($CS_2$) in the presence of a base such as alkali metal hydroxides (e.g. sodium hydroxide, potassium hydroxide, etc.), alkali metal alkoxides (e.g. sodium methoxide, sodium ethoxide, potassium ethoxide, etc.).

The starting thiol derivative [XI-a]:

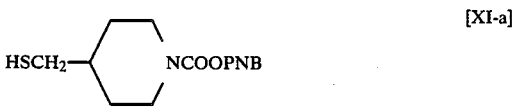

[XI-a]

wherein PNB means p-nitrobenzyl group, can be prepared, for example, according to the following scheme.

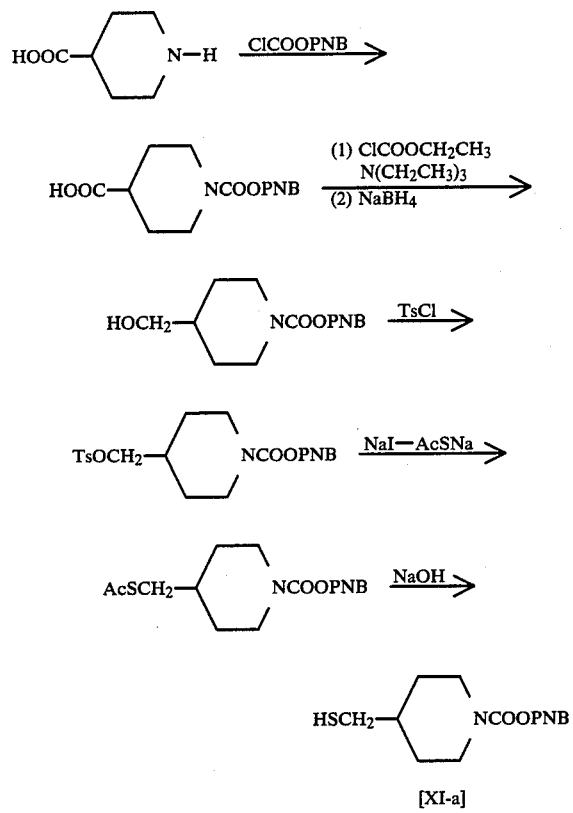

Also, the metal salts of the formula:

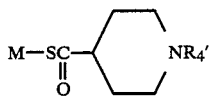

wherein M and $R_4'$ are as defined above, can be prepared from the thiol carboxylic acid of the formula:

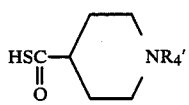

wherein $R_4'$ is as defined above, which can be easily prepared by reacting the compounds of the formula:

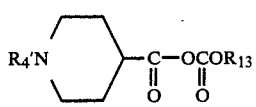

wherein $R_4'$ is as defined above, and $R_{13}$ is a $C_1$-$C_4$ alkyl group, with hydrogen sulfide, by treating with an alkali metal hydroxide such as sodium hydroxide, potassium hydroxide, etc., an alkali metal alkoxide such as sodium methoxide, sodium ethoxide, etc., or an alkali metal hydride such as sodium hydride.

The following examples are given to illustrate the present invention in greater detail, but the present invention is not limited thereto.

EXAMPLE 1

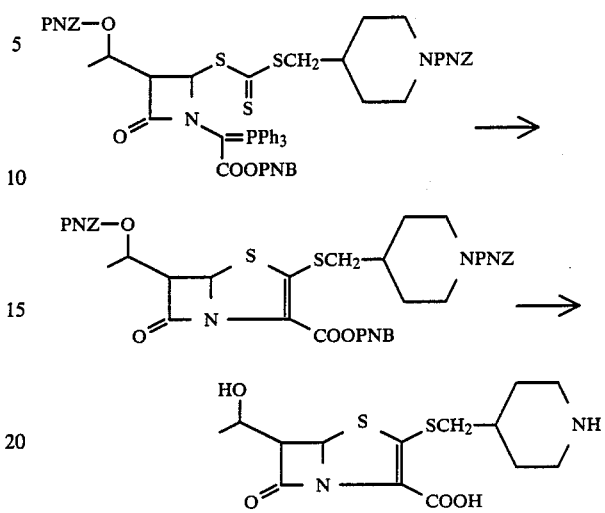

(a) A solution of 3-(1-p-nitrobenzyloxycarbonyloxyethyl)-4-[4-(1-p-nitrobenzyloxycarbonylpiperidinyl)methylthio]-thiocarbonylthio-1-(1-p-nitrobenzyloxycarbonyl-triphenyl-phosphoranylidenemethyl)-2-azetidinone (1.0 g) in o-xylene (200 ml) was refluxed in the presence of a catalytic amount of hydroquinone for 5 hours under nitrogen atmosphere. Evaporation of o-xylene gave an oily residue which was then purified by silica gel chromatography to give 5,6-trans-2-[4-(1-p-nitrobenzyloxycarbonylpiperidinyl)-methylthio]-6-(1-p-nitrobenzyloxycarbonyloxyethyl)penem-3-carboxylic acid p-nitrobenzyl ester and a corresponding 5,6-cis isomer.

5,6-trans isomer $IR_{max}^{CHCl_3}$(cm$^{-1}$): 1790, 1750, 1687, 1608, 1520, 1440, 1347, 1260, 1114, 850.

NMRδ(CDCl$_3$): 1.51(3H, d, J=6.5 Hz), 2.89(2H, d, J=6 Hz), 3.92(1H, dd, J=1.5 and 8 Hz), 5.22(2H, s), 5.25(2H, s), 5.45(1H, d, J=13.5 Hz), 5.66(1H, d, J=1.5 Hz), 7.51(4H, d, J=9 Hz), 7.61(2H, d, J=9 Hz), 8.11(2H, d, J=9 Hz), 8.13(4H, d, J=9 Hz).

5,6-cis isomer $IR_{max}^{CHCl_3}$(cm$^{-1}$): 1787, 1740, 1685, 1605, 1515, 1345, 1240, 1160, 1112, 847.

NMRδ(CDCl$_3$): 1.62(3H, d, J=6.5 Hz), 4.11(1H, dd, J=4 and 10 Hz), 5.22(2H, s), 5.26(2H, s), 5.46 (1H, d, J=14 Hz), 5.77(1H, d, J=4 Hz), 7.51(2H, d, J=8.5 Hz), 7.54(2H, d, J=8.5 Hz), 7.61(2H, d, J=8.5 Hz), 8.22(4H, d, J=8.5 Hz), 8.24(2H, d, J=8.5 Hz).

(b-1) A mixture of 2-[4-(1-p-nitrobenzyloxycarbonylpiperidinyl)-methylthio]-6-(1-p-nitrobenzyloxycarbonyloxyethyl)penem-3-carboxylic acid p-nitrobenzyl ester (5,6-trans isomer, 150 mg) and 5% palladium-charcoal (450 mg) which had been stirred in ethanol under hydrogen atmosphere at room temperature for 1 hour was stirred in tetrahydrofuran (9 ml), ethanol (1 ml) and 0.025M-phosphate buffer (pH 6.8, 10 ml) under hydrogen atmosphere for 3 hours at room temperature. The catalyst was removed by filtration and washed with water. The combined solution was concentrated to a volume of 5 to 10 ml in vacuo and chromatographed on Diaion CHP-20P (15 ml). Fractions eluted with 15% methanol-water were collected and lyophilized to give 2-(4-piperidinylmethylthio)-6-(1-hydroxyethyl)penem-3-carboxylic acid (5,6-trans isomer, 31 mg) as a powder.

IR$_{max}^{KBr}$(cm$^{-1}$): 1765, 1568, 1366.

UV λ$_{max\ nm}^{H2O}$: 250, 320.

NMRδ(D$_2$O): 1.21(3H, d, J=6.4 Hz), 3.81(1H, dd, J=1.2 and 6.4 Hz), 4.15(1H, quintet, J=6.4 Hz), 5.57(1H, d, J=1.2 Hz).

(b-2) 2-(4-Piperidinylmethylthio)-6-(1-hydroxyethyl)-penem-3-carboxylic acid (5,6-cis isomer, 26 mg) as a powder was prepared from 2-[4-(1-p-nitrobenzyloxycarbonylpiperidinyl)-methylthio]-6-(1-p-nitrobenzyloxycarbonyloxyethyl)penem-3-carboxylic acid p-nitrobenzyl ester (5,6-cis isomer, 130 mg) by a procedure similar to that described in (b-1) above.

UV λ$_{max\ nm}^{H2O}$: 250, 317.

(a') (5R,6S)-2-[4-(1-p-Nitrobenzyloxycarbonylpiperidinyl)-methylthio]-6-[(R)-1-p-nitrobenzyloxycarbonyloxyethyl]penem-3-carboxylic acid p-nitrobenzyl ester having a specific rotation of [α]$_D^{20}$+71.6° (C=0.457, CHCl$_3$), and IR and NMR spectra identical to those of trans-isomer described above and (5S,6S)-2-[4-(1-p-nitrobenzyloxycarbonylpiperidinyl)-methylthio]-6-[(R)-1-p-nitrobenzyloxycarbonyloxyethyl]penem-3-carboxylic acid p-nitrobenzyl ester having a specific rotation of [α]$_D^{20}$−68.0° (c=0.22 CHCl$_3$), and IR and NMR identical to those of cis-isomer described above were prepared from (3S,4R)-3-[(R)-1-p-nitrobenzyloxycarbonyloxyethyl]-4-[4-(1-p-nitrobenzyloxycarbonylpiperidinyl)-methylthio]-thiocarbonylthio-1-(1-p-nitrobenzyloxycarbonyltriphenylphosphoranylidenemethyl)-2-azetidinone by a procedure similar to that described in (a) above.

(b') (5R,6S)-2-(4-Piperidinylmethylthio)-6-[(R)-1-hydroxyethyl]penem-3-carboxylic acid having a specific rotation of [α]$_D^{20}$+102.7° (C=0.27, H$_2$O), and IR and UV spectra identical to those 5,6-trans of isomer described above was prepared from (5R,6S)-2-[4-(1-p-nitrobenzyloxycarbonylpiperidinyl)-methylthio]-6-[(R)-1-p-nitrobenzyloxycarbonyloxyethyl]penem-3-carboxylic acid p-nitrobenzyl ester by a procedure similar to that described in (b-1) above.

EXAMPLE 2

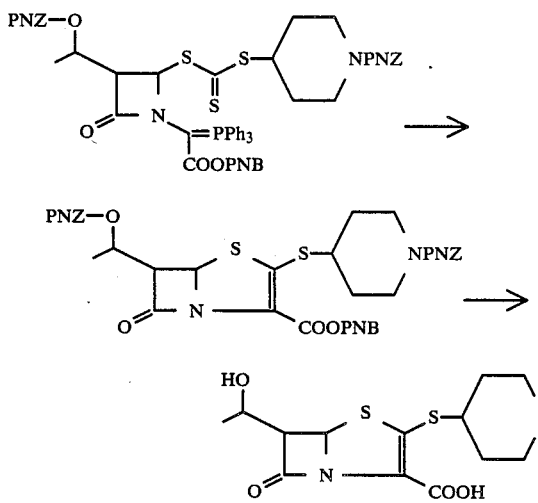

(a) A solution of 3-(1-p-nitrobenzyloxycarbonyloxyethyl)-4-[4-(1-p-nitrobenzyloxycarbonylpiperidinyl)thio]thiocarbonylthio-1-(1-p-nitrobenzyloxycarbonyltriphenylphosphoranylidenemethyl-2-azetidinone (1.75 g) in o-xylene (578 ml) was refluxed in the presence of a catalytic amount of hydroquinone for 9 hours under nitrogen atmosphere. Evaporation of o-xylene gave an oily residue which was then purified by silica gel chromatography to give 5,6-trans-2-[4-(1-p-nitrobenzyloxycarbonylpiperidinyl)thio]-6-(1-p-nitrobenzyloxycarbonyloxyethyl)penem-3-carboxylic acid p-nitrobenzyl ester and a corresponding 5,6-cis isomer.

5,6-trans isomer

IR$_{max}^{CHCl3}$(cm$^{-1}$): 1785, 1722, 1695, 1601, 1518, 1340, 1105.

NMRδ(CDCl$_3$): 1.50(3H, d, J=6.5 Hz), 3.91 (1H, dd, J=7.5 and 2 Hz), 5.21(2H, S), 5.24 (2H, S), 5.30(2H, AB, J=14 Hz), 5.65(1H, d, J=2 Hz).

5,6-cis isomer

IR$_{max}^{CHCl3}$(cm$^{-1}$): 1785, 1740, 1700, 1605, 1520, 1342, 1105.

NMRδ(CDCl$_3$): 1.60(3H, d, J=6.5 Hz), 4.13(1H, dd, J=10.5 and 4 Hz), 5.21(2H, s), 5.24(2H, s), 5.26(2H, AB, J=14.5 Hz), 5.73(1H, d, J=4 Hz).

(b-1) A mixture of 2-[4-(1-p-nitrobenzyloxycarbonylpiperidinyl)thio]-6-(1-p-nitrobenzyloxycarbonyloxyethyl)penem-3-carboxylic acid p-nitrobenzyl ester (5,6-trans isomer, 200 mg) and 5% palladium-charcoal (600 mg) which had been stirred in ethanol under hydrogen atmosphere at room temperature for 1 hour was stirred in tetrahydrofuran (9 ml), ethanol (1 ml) and 0.025M-phosphate buffer (pH 6.8, 10 ml) under hydrogen atmosphere for 5 hours at 25° C. The catalyst was removed by filtration and washed with water. The combined solution was concentrated to a volume of 5 to 10 ml in vacuo and chromatographed on Diaion CHP-20P (15 ml). Fractions eluted with 10% methanol-water were collected and lyophilized to give 2-(4-piperidinylthio)-6-(1-hydroxyethyl)penem-3-carboxylic acid (5,6-trans isomer, 22 mg) as a powder.

IR$_{max}^{KBr}$(cm$^{-1}$): 3400(br), 1765, 1625, 1560, 1370, 1282.

UV λ$_{max\ nm}^{H2O}$(ε): 259(5555), 321(7328).

NMRδ(D$_2$O): 1.25(3H, d, J=6 Hz), 3.89(1H, dd, J=1.5 and 6 Hz), 5.63(1H, d, J=1.5 Hz).

(b-2) 2-(4-Piperidinylthio)-6-(1-hydroxyethyl)penem-3-carboxylic acid (5,6-cis isomer, 30 mg) was prepared from 2-[4-(1-p-nitrobenzyloxycarbonylpiperidinyl)-thio]-6-(1-p-nitrobenzyloxycarbonyloxyethyl)penem-3-carboxylic acid p-nitrobenzyl ester (5,6-cis isomer, 140 mg) by a procedure similar to that described in (b-1) above.

IR$_{max}^{KBr}$(cm$^{-1}$): 1770, 1612, 1565, 1372, 1278, 1125, 1075.

UV λ$_{max\ nm}^{H2O}$: 255, 318.

NMRδ(D$_2$O): 1.32(3H, d, J=7 Hz), 3.91(1H, dd, J=4.5 and 10 Hz), 5.70(1H, d, J=4.5 Hz).

(a') (5R,6S)-2-[4-(1-p-Nitrobenzyloxycarbonylpiperidinyl)thio]-6-[(R)-1-p-nitrobenzyloxycarbonyloxyethyl]penem-3-carboxylic acid p-nitrobenzyl ester having a specific rotation of [α]$_D^{20}$+80.8° (C=0.124, CHCl$_3$), and IR and NMR spectra identical to those of trans-isomer described above, and (5R,6S)-2-[4-(1-p-nitrobenzyloxycarbonylpiperidinyl)thio]-6-[(R)-1-p-nitrobenzyloxycarbonyloxyethyl]penem-3-carboxylic acid p-nitrobenzyl ester having a specific rotation of [α]$_D^{20}$−71.9° (C=0.095, CHCl$_3$), and IR and NMR spectra identical to those of cis-isomer described above were prepared from (3S,4R)-3-[(R)-1-p-nitrobenzyloxycarbonyloxyethyl]-4-[4-(1-p-nitrobenzyloxycarbonyl-piperidinyl)-thio]-thiocarbonylthio1-(1-p-nitrobenzyloxycarbonyltriphenylphosphoranylidenemethyl)-2-azetidinone by a procedure similar to that described in (a) above.

(b') (5R,6S)-2-(4-Piperidinylthio)-6-[(R)-1-hydroxyethyl]penem-3-carboxylic acid having a specific rotation of $[\alpha]_D^{20} + 160.6°$ (C=0.07, H$_2$O), and IR, NMR and UV spectra identical to those of 5,6-trans-isomer described above was prepared from (5R,6S)-2-[4-(1-p-nitrobenzyloxycarbonylpiperidinyl)-thio]-6-[(R)-1-p-nitrobenzyloxycarbonyloxyethyl]penem-3-carboxylic acid p-nitrobenzyl ester by a procedure similar to that described in (b-1) above.

(c) Stereoisomer on 1-p-nitrobenzyloxycarbonyloxyethyl group of 2-[4-(1-p-nitrobenzyloxycarbonyl-piperidinyl)thio]-6-(1-p-nitrobenzyloxycarbonyloxyethyl)penem-3-carboxylic acid p-nitrobenzyl ester (5,6 trans and 6,8-erythro isomer) was prepared from 3-(1-p-nitrobenzyloxycarbonyloxyethyl)-4-[4-(1-p-nitrobenzyloxycarbonylpiperidinyl)thio]-thiocarbonylthio-1-p-nitrobenzyloxycarbonyl-triphenylphosphoranylidenemethyl-2-azetidinone, which was derived from a mixture of (R) and (S) isomers (1:1) on hydroxyethyl group of 1-(di-p-anisyl)methyl-3-hydroxyethyl-4-acetoxy-2-azetidinone, by a procedure similar to that described in (a) above.

IR$_{max}^{CHCl3}$(cm$^{-1}$): 1788, 1746, 1693, 1608, 1522, 1438 1347, 1246, 1205, 1108.

NMRδ(CDCl$_3$): 1.52(3H, d, J=6.5 Hz), 4.05(1H, dd, J=1.5 and 4.5 Hz), 5.22(2H, s), 5.26(2H, s), 5.60(1H, d, J=1.5 Hz), 7.51(2H, d, J=9 Hz), 7.53(2H, d, J=9 Hz), 7.60(2H, d, J=9 Hz), 8.21(6H, d, J=9 Hz).

(d) Stereoisomer on 1-hydroxyethyl group of 2-(4-piperidinylthio)-6-(1-hydroxyethyl)penem-3-carboxylic acid (5,6-trans and 6,8-erythro isomer, 15 mg) was prepared from 2-[4-(1-p-nitrobenzyloxycarbonyl-piperidinyl)thio]-6-(1-p-nitrobenzyloxycarbonyloxyethyl)penem-3-carboxylic acid p-nitrobenzyl ester (5,6-trans and 6,8-erythro isomer, 250 mg) by a procedure similar to that described in (b-1) above.

UV λ$_{max}$ nm$^{H2O}$(ε): 258(5216), 321(6802).

phenylphosphoranylidenemethyl)-2-azetidinone (170 g) in o-xylene (85 ml) was refluxed in the presence of a catalytic amount of hydroquinone for 3.5 hours under nitrogen atmosphere. Evaporation of o-xylene gave an oily residue which was then purified by silica gel chromatography to give 5,6-trans-2-[4-(1-p-nitrobenzyloxycarbonyl)piperidinylmethyl]-6-(1-p-nitrobenzyloxycarbonyloxyethyl)penem-3-carboxylic acid p-nitrobenzyl ester and a corresponding 5,6-cis isomer.

5,6-trans isomer

IR$_{max}^{CHCl3}$(cm$^{-1}$): 1783, 1745, 1700, 1685, 1603, 1520, 1438, 1345, 1312, 1260, 1107, 1005, 845.

NMRδ(CDCl$_3$): 1.49(3H, d, J=6.5 Hz), 3.92(1H, dd, J=1.5 and 7.5 Hz), 5.20(2H, s), 5.23(2H, s), 5.36(1H, d, J=14 Hz), 5.61(1H, d, J=1.5 Hz), 7.47(4H, d, J=8.5 Hz), 7.57(2H, d, J=8.5 Hz), 8.13(6H, d, J=8.5 Hz).

5,6-cis isomer

IR$_{max}^{CHCl3}$(cm$^{-1}$): 1784, 1750, 1695, 1610, 1580, 1526, 1440, 1350, 1315, 1245, 1168, 1114, 1010, 850.

NMRδ(CDCl$_3$): 1.60(3H, d, J=6 Hz), 5.21(2H, s), 5.26(2H, s), 5.41(1H, d, J=13.5 Hz), 5.70(1H, d, J=4 Hz), 7.50(2H, d, J=8.5 Hz), 7.54(2H, d, J=8.5 Hz), 7.60(2H, d, J=8.5 Hz), 8.22(6H, d, J=8.5 Hz).

(b) A mixture of 2-[4-(1-p-nitrobenzyloxycarbonyl)-piperidinyl]methyl-6-(1-p-nitrobenzyloxycarbonyloxyethyl)penem-3-carboxylic acid p-nitrobenzyl ester (5,6-trans isomer, 200 mg) and 5% palladium-charcoal (600 mg) which had been stirred in ethanol under hydrogen atmosphere at room temperature for 1 hour was stirred in tetrahydrofuran (9 ml), ethanol (1 ml) and 0.025M-phosphate buffer (pH 6.8, 10 ml) under hydrogen atmosphere for 1 hour at room temperature. The catalyst was removed by filtration and washed with water. The combined solution was concentrated to a volume of 5 to 10 ml in vacuo and chromatographed on Diaion CHP-20P (20 ml). Fractions eluted with 10% methanol-water were collected and lyophilized to give 2-(4-piperidinyl)methyl-6-(1-hydroxyethyl)penem-3-carboxylic acid (5,6-tarns isomer) as a powder.

UV λ$_{max}$ nm$^{H2O}$: 260, 302.

EXAMPLE 3

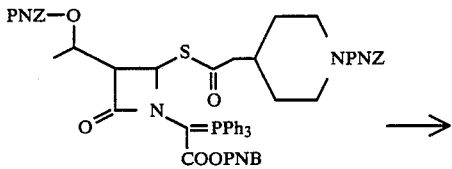

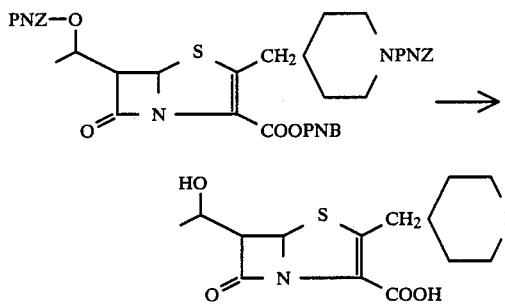

(a) A solution of 3-(1-p-nitrobenzyloxycarbonyloxyethyl)-4-[4-(1-p-nitrobenzyloxycarbonyl)piperidinylmethyl]carbonylthio-1-(1-p-nitrobenzyloxycarbonyltri-

EXAMPLE 4

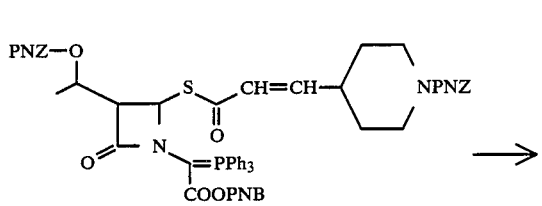

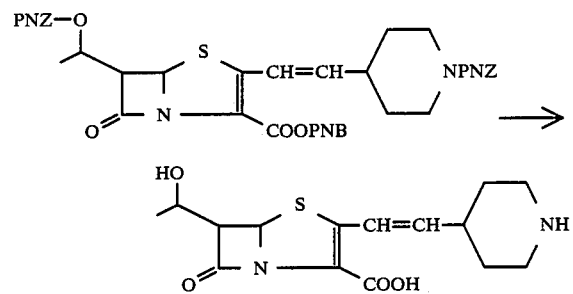

(a) A solution of 3-(1-p-nitrobenzyloxycarbonyloxyethyl)-4-[2-[4-(1-p-nitrobenzyloxycarbonyl)piperidinyl]ethenyl]carbonylthio-1-p-nitrobenzyloxycarbonyltriphenylphosphoranylidenemethyl-2-azetidinone (0.84 g) in toluene (42 ml) was refluxed in the presence of a catalytic amount of hydroquinone for 10 hours under nitrogen atmosphere. Evaporation of toluene gave an oily residue which was then purified by silica gel chromatography to give 5,6-trans-2-[2-[4-(1-p-nitrobenzyloxycarbonyl)piperidinyl]ethenyl]-6-(1-p-nitrobenzyloxycarbonyloxyethyl)penem-3-carboxylic acid p-nitrobenzyl ester and a corresponding 5,6-cis isomer.

5,6-trans isomer

IR$_{max}^{CHCl_3}$(cm$^{-1}$): 1783, 1745, 1690, 1605, 1520, 1440, 1346, 1314, 1245, 1170, 1134, 1108, 1012, 845.

NMRδ(CDCl$_3$): 1.50(3H, d, J=6.5 Hz), 3.90(1H, dd, J=1.5 and 8 Hz), 5.23(2H, S), 5.26(2H, S), 5.53(1H, d, J=1.5 Hz), 6.02(1H, dd, J=6.5 and 16 Hz), 7.21(1H, dd, J=1 and 16 Hz), 7.52(4H, d, J=8.5 Hz), 7.62(2H, d, J=8.5 Hz), 8.21(6H, d, J=8.5 Hz).

5,6-cis isomer

IR$_{max}^{CHCl_3}$(cm$^{-1}$): 1784, 1740(sh), 1702, 1610, 1524, 1442, 1349, 1315, 1250, 1163, 1015, 965, 850.

(b) A mixture of 2-[2-[4-(1-p-nitrobenzyloxycarbonyl)piperidinyl]ethenyl]-6-(1-p-nitrobenzyloxycarbonyloxyethyl)penem-3-carboxylic acid p-nitrobenzyl ester (5,6-trans isomer, 160 mg) and 5% palladium-charcoal (500 mg) which had been stirred in ethanol under hydrogen atmosphere at room temperature for 1 hour was stirred in tetrahydrofuran (9 ml), ethanol (1 ml) and 0.025M-phosphate buffer (pH 6.8, 8 ml) under hydrogen atmosphere for 1 hour at room temperature. The catalyst was removed by filtration and washed with water. The combined solution was concentrated to a volume of 5 to 10 ml in vacuo and chromatographed on Diaion CHP-20P (20 ml). Fractions eluted with 15% methanol-water were collected and lyophilized to give 2-2-(4-piperidinyl)ethenyl)-6-(1-hydroxyethyl)penem-3-carboxylic acid (5,6-trans isomer) as a powder.

IR$_{max}^{KBr}$(cm$^{-1}$): 1760, 1580, 1353.

UV λ$_{max\ nm}^{H2O}$: 260, 330.

NMRδ(D$_2$O): 1.21(3H, d, J=6 Hz), 3.75(1H, dd, J=1.5 and 6 Hz), 4.16(1H, quintet, J=6 Hz), 5.47(1H, d, J=1.5 Hz), 5.86(1H, dd, J=6 and 16 Hz), 7.15(1H, d, J=16 Hz).

(c) Stereoisomer on 1-p-nitrobenzyloxycarbonyloxyethyl group of 2-[2-[4-(1-p-nitrobenzyloxycarbonyl)piperidinyl]ethenyl]-6-(1-p-nitrobenzyloxycarbonyloxyethyl)penem-3-carboxylic acid p-nitrobenzyl ester (6,8-erythro isomer) was prepared from 3-(1-p-nitrobenzyloxycarbonyloxyethyl)-4-[2-[4-(1-p-nitrobenzyloxycarbonyl)piperidinyl]ethenyl]carbonylthio-1-p-nitrobenzyloxycarbonyltriphenylphosphoranylidenemethyl-2-azetidinone, which was derived from a mixture of (R) and (S) isomers (1:1) on hydroxyethyl group of 1-(di-p-anisyl)methyl-3-hydroxyethyl-4-acetoxy-2-azetidinone, by the procedure similar to that described in (a) above.

IR$_{max}^{CHCl_3}$(cm$^{-1}$): 1790, 1745(sh), 1705, 1610, 1525, 1440, 1350, 1318, 1250, 1178, 1140, 1016, 853.

NMRδ(CDCl$_3$): 1.45(3H, d, J=6.5 Hz), 3.93(1H, dd, J=1.5 and 4 Hz), 5.14(2H, S), 5.19(2H, S), 5.36(1H, d, J=14 Hz), 5.36(1H, d, J=1.5 Hz), 5.95(1H, dd, J=6.5 and 15 Hz), 7.21(1H, d, J=15 Hz), 7.42(2H, d, J=8.5 Hz), 7.45(2H, d, J=8.5 Hz), 7.54(2H, d, J=8.5 Hz), 8.13(6H, d, J=8.5 Hz).

EXAMPLE 5

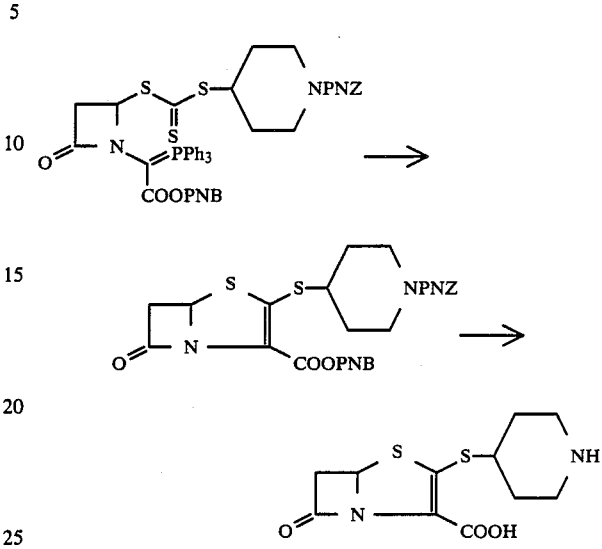

(a) A solution of 4-[4-(1-p-nitrobenzyloxycarbonylpiperidinyl)thio]thiocarbonylthio-1-p-nitrobenzyloxycarbonyltriphenylphosphoranylidenemethyl-2-azetidinone (1.63 g) in o-xylene (543 ml) was refluxed in the presence of a catalytic amount of hydroquinone for 4.5 hours under nitrogen atmosphere. Evaporation of o-xylene gave an oily residue which was then purified by silica gel chromatography to give 2-[4-(1-p-nitrobenzyloxycarbonylpiperidinyl)thio]penem-3-carboxylic acid p-nitrobenzyl ester.

IR$_{max}^{CHCl_3}$(cm$^{-1}$): 1790, 1693, 1608, 1522, 1348, 1325, 1250, 1192, 1110.

NMRδ(CDCl$_3$): 1.37-2.43(4H, m), 2.83-4.37(7H, m), 5.23(2H, s), 5.23(1H, d, J=14 Hz), 5.46(1H, d, J=14 Hz), 5.75(1H, dd, J=2 and 4 Hz), 7.53(2H, d, J=8 Hz), 7.64(2H, d, J=8 Hz), 8.23(4H, d, J=8 Hz).

(b) A mixture of 2-[4-(1-p-nitrobenzyloxycarbonylpiperidinyl)thio]penem-3-carboxylic acid p-nitrobenzyl ester (150 mg) and 5% palladium-charcoal (250 mg) which had been stirred in ethanol under hydrogen atmosphere at room temperature for 1 hour was stirred in tetrahydrofuran (7 ml), ethanol (1 ml) and 0.025M-phosphate buffer (pH 6.8, 10 ml) under hydrogen atmosphere for 1 hour at room temperature. The catalyst was removed by filtration and washed with water. The combined solution was concentrated to a volume of 5 to 10 ml in vacuo and chromatographed on Diaion CHP-20P (10 ml). Fractions eluted with 10% methanol-water were collected and lyophilized to give 2-(4-piperidinyl)thiopenem-3-carboxylic acid as a powder.

IR$_{max}^{KBr}$(cm$^{-1}$): 1762, 1620, 1360, 1270. UV λ$_{max\ nm}^{H2O}$: 250, 318

The following compounds were prepared from the corresponding phosphoran derivatives according to the procedures similar to those described in Examples 1, 3 and 5.

The solvents used in cyclization were selected from aromatic hydrocarbons, i.e., benzene, toluene, xylene and o-xylene, depending on the reaction temperature used as described in the following tables.

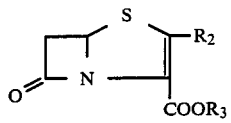

| Example No. | $R_2$ | $R_3$ | Reaction time (hr.) & Temperature | Spectral Data |
|---|---|---|---|---|
| 6 | —S(CH$_2$)$_3$C(CH$_3$)$_2$NHPNZ | PNB | 3.5 145° C. | IR$_{max}^{CHCl_3}$(cm$^{-1}$): 3440, 1790, 1725, 1690, 1605, 1520, 1505, 1345, 1325, 1250, 1190, 1108, 843 NMRδ(CDCl$_3$): 1.31(6H,s), 2.93 (2H,t,J=6Hz), 3..52(1H,dd,J= 2 and 16.5Hz), 3.79(1H,dd,J= 4 and 16.5Hz), 4.80(1H,bs), 5.12(2H,s), 5.23(1H,d,14Hz), 5.42(1H,d,J=14Hz), 5.68(1H,dd, J=2 and 4Hz), 7.46(2H,d,J= 8.5Hz), 7.59(2H,d,J=8.5Hz), 8.16(4H,d,J=8.5Hz) |
|  | —S(CH$_2$)$_3$C(CH$_3$)$_2$NH$_2$ | H | 1 room temp. | IR$_{max}^{KBr}$(cm$^{-1}$): 1780, 1560, 1372, 1288, 1127 |
| 7 | —S(CH$_2$)$_2$C(CH$_3$)$_2$CH$_2$NHPNZ | PNB | 6 145° C. | IR$_{max}^{Nujol}$(cm$^{-1}$): 3350, 1787, 1718, 1680, 1605, 1515, 1350, 1333, 1200, 1113, 1032, 845 NMRδ(CDCl$_3$): 0.96(6H,s), 3.08 (2H,d,J=7Hz), 3.48(2H,s), 3.55 (1H,dd,J=2 and 16.5Hz), 3.80 (1H,dd,J=4 and 16.5Hz), 5.22 (2H,s), 5.28(1H,d,J=14Hz), 5.43(1H,d,J=14Hz), 5.73(1H,dd, J=2 and 4Hz), 7.53(2H,d,J=8Hz), 7.66(2H,d,J=8Hz), 8.22(4H,d, J=8Hz) |
|  | —S(CH$_2$)$_2$C(CH$_3$)$_2$CH$_2$NH$_2$ | H | 1 room temp. | IR$_{max}^{KBr}$(cm$^{-1}$): 1770, 1570, 1370, 1280 UV λ$_{max\ nm}^{H_2O}$: 250, 320 |
| 8 | —S(CH$_2$)$_2$C(CH$_3$)$_2$NHPNZ | PNB | 6 145° C. | IR$_{max}^{CHCl_3}$(cm$^{-1}$): 1790, 1723, 1682, 1605, 1518, 1500, 1345, 1325, 1255, 1190, 1110, 840 NMRδ(CDCl$_3$): 1.36(6H,s), 3.52 (1H,dd,J=2 and 16.5Hz), 3.78 (1H,dd,J=3.5 and 16.5Hz), 4.87(1H,bs), 5.12(2H,s), 5.20 (1H,d,J=14Hz), 5.43(1H,d,J= 14Hz), 5.68(1H,dd,J=2 and 3.5Hz), 7.45(2H,d,J=9Hz),7.56 (2H,d,J=9Hz), 8.14(4H,d,J=9Hz) |
|  | —S(CH$_2$)$_2$C(CH$_3$)$_2$NH$_2$ | H | 1 room temp. | IR$_{max}^{KBr}$(cm$^{-1}$): 1785, 1632, 1570, 1365, 1130 |
| 9 | —SCH$_2$C(CH$_3$)$_2$NHPNZ | PNB | 5.5 145° C. | IR$_{max}^{CHCl_3}$(cm$^{-1}$): 3440, 1793, 1730, 1690, 1610, 1525, 1505, 1350, 1330, 1195, 1113, 1090, 850 NMRδ(CDCl$_3$): 1.43(6H,s),3.42 (1H,d,J=13Hz), 3.52(1H,dd,J= 2 and 16.5Hz), 3.58(1H,d,J= 13Hz), 3.77(1H,dd,J=4 and 16.5Hz), 5.03(1H,bs), 5.13 (2H,s), 5.64(1H,dd,J=2 and 4Hz), 7.42(2H,d,J=9Hz), 7.57 (2H,d,J=9Hz), 8.13(4H,d,J=9Hz) |
|  | —SCH$_2$C(CH$_3$)$_2$NH$_2$ | H | 1 room temp. | IR$_{max}^{KBr}$(cm$^{-1}$): 1770, 1628, 1570, 1375, 1280 |
| 10 | —SCH$_2$C(CH$_3$)$_2$CH$_2$NHPNZ | PNB | 6 145° C. | IR$_{max}^{CHCl_3}$(cm$^{-1}$): 3450, 1792, 1725 1610, 1520, 1347, 1325, 1190, 1110, 845 NMRδ(CDCl$_3$): 1.05(6H,s), 3.00 (2H,s), 3.19(2H,d,J=7Hz), 3.57 (1H,dd,J=2 and 16.5Hz), 3.80 (1H,dd,J=4 and 16.5Hz), 5.22 (2H,s), 5.27(1H,d,J=14Hz), 5.50(1H,,d,J=14Hz), 5.72(1H,dd, J=2 and 4Hz), 7.53(2H,d,J= 8.5Hz), 7.62(2H,d,J=8.5Hz), 8.21(4H,d,J=8.5Hz) |
|  | —SCH$_2$C(CH$_3$)$_2$CH$_2$NH$_2$ | H | 1 |  IR$_{max}^{KBr}$(cm$^{-1}$): 1770, 1562, 1355, |

-continued

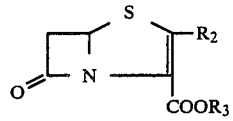

| Example No. | R₂ | R₃ | Reaction time (hr.) & Temperature | Spectral Data |
|---|---|---|---|---|
|  |  |  | room temp. | 1280 |
| 11 | —SCH₂C(CH₃)₂CH₂CH₂NHPNZ | PNB | 5.5<br>145° C. | IR$_{max}^{CHCl_3}$(cm$^{-1}$): 3450, 1790, 1720, 1605, 1507, 1350, 1328, 1110, 845<br>NMRδ(CDCl₃): 1.08(6H,s), 2.98(2H, s), 3.55(1H,dd,J=2 and 16Hz), 3.78(1H,dd,J=3.5 and 16Hz), 5.18(2H,s), 5.23(1H,d,J=14Hz), 5.44(1H,d,J=14Hz), 5.69(1H,dd, J=2 and 3.5Hz), 7.49(2H,d,J= 8.5Hz), 7.62(2H,d,J=8.5Hz), 8.18(4H,d,J=8.5Hz) |
|  | —SCH₂C(CH₃)₂CH₂CH₂NH₂ | H | 1<br>room temp. | $\lambda_{max\ nm}^{H_2O}$: 250, 320 |
| 12 | —CH₂CH₂C(CH₃)₂NHPNZ | PNB | 2<br>145° C. | IR$_{max}^{CHCl_3}$: 1790, 1727, 1610, 1580, 1525, 1348, 1315, 1260, 1197, 1082, 850<br>NMδ(CDCl₃): 1.00(6H,s), 3.50 (1H,dd,J=2 and 16Hz), 3.87(1H, dd,J=4 and 16Hz), 5.00(1H,bs), 5.13(2H,s), 5.20(1H,d,J=14Hz), 5.40(1H,d,J=14Hz), 5.60(1H, dd,J=2 and 4Hz), 7.48(2H,d,J= 9Hz), 7.59(2H,d,J=9Hz), 8.17 (4H,d,J=9Hz) |
|  | —CH₂CH₂C(CH₃)₂NH₂ | H | 1<br>room temp. | IR$_{max}^{KBr}$(cm$^{-1}$): 1762, 1587, 1557, 1368, 1288,<br>UV $\lambda_{max\ nm}^{H_2O}$: 259, 303 |
| 13 | —CH₂C(CH₃)₂CH₂NHPNZ | PNB | 6.5<br>145° C. | IR$_{max}^{Nujol}$(cm$^{-1}$): 3440, 1782, 1722, 1697, 1600, 1563, 1510, 1340, 1302<br>NMR (CDCl₃): 1.02(6H,s), 2.81(1H,d,J= 14Hz), 2.92(1H,d,J=14Hz), 3.08 (2H,d,J=6.5Hz), 3.56(1H,dd,J= 2 and 17Hz), 3.77(1H,dd,J=4 and 17Hz), 5.21(2H,s), 5.26(1H,d, J=14Hz), 5.42(1H,d,J=14Hz), 5.66(1H,dd,J=2 and 4Hz), 7.53 (2H,d,J=9Hz), 7.63(2H,d,J=9Hz), 8.24(4H,d,J=9Hz) |
|  | —CH₂C(CH₃)₂CH₂NH₂ | H | 1<br>room temp. | UV $\lambda_{max\ nm}^{H_2O}$: 255, 300 |
| 14 | —CH₂C(CH₃)₂NHPNZ | PNB | 2<br>145° C. | IR$_{max}^{CHCl_3}$(cm$^{-1}$): 3430, 1782, 1715, 1600, 1562, 1515, 1340, 1305, 1078, 840<br>NMRδ(CDCl₃): 1.40(6H,s), 3.50(1H, dd,J=2 and 16.5Hz), 3.73(1H,dd, J=4 and 16.5Hz), 5.16(2H,s), 5.20(1H,d,J=14Hz), 5.43(1H,d, J=14Hz), 5.62(1H,dd,J=2 and 4Hz), 7.49(2H,d,J=9Hz), 7.59 (2H,d,J=9Hz), 8.19(4H,d,J=9Hz) |
|  | —CH₂C(CH₃)₂NH₂ | H | 1<br>room temp. | IR$_{max}^{KBr}$(cm$^{-1}$): 1770, 1560, 1370, 1288 |
| 15 | —CH₂CH₂C(CH₃)₂CH₂NHPNZ | PNB | 1.5<br>145° C. | IR$_{max}^{CHCl_3}$(cm$^{-1}$): 3450, 3380, 1782, 1704, 1600, 1570, 1518, 1340, 1310, 1255, 1122, 840<br>NMRδ(CDCl₃): 0.91(6H,s), 3.09 (2H,d,J=7Hz), 3.54(1H,dd,J=2 and 16.5Hz), 3.79(1H,dd,J=3.5 and 16.5Hz), 5.23(2H,s), 5.24 (1H,d,J=14Hz), 5.48(1H,d,14Hz), 5.66(1H,d,J=2 and 3.5Hz), 7.52(2H,d,J=9Hz), 7.63(2H,d, J=9Hz), 8.23(4H,d,J=9Hz) |
|  | —CH₂CH₂C(CH₃)₂CH₂NH₂ | H | 1<br>room temp. | IR$_{max}^{KBr}$(cm$^{-1}$): 3400, 1770, 1562, 1370, 1288<br>UV $\lambda_{max\ nm}^{H_2O}$: 254, 300 |
| 16 | —CH₂CH₂CH₂C(CH₃)₂NHPNZ | PNB | 1.5 | IR$_{max}^{CHCl_3}$(cm$^{-1}$): 3440, 1785, 1720, |

-continued

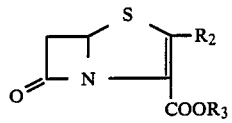

| Example No. | R₂ | R₃ | Reaction time (hr.) & Temperature | Spectral Data |
|---|---|---|---|---|
| | | | 145° C. | 1605, 1570, 1520, 1347, 1313, 1258, 1082, 845 NMRδ(CDCl₃): 1.29(6H,s), 3.52 (1H,dd,H=2 and 16Hz), 3.93(1H, dd,J=3.5 and 16Hz), 4.77(1H, bs), 5.12(2H,s), 5.20(1H,d,J= 14Hz), 5.40(1H,d,J=14Hz), 5.62 (1H,dd,J=2 and 3.5Hz), 7.44 (2H,d,J=8.5Hz), 7.56(2H,d,J= 8.5Hz), 8.16(4H,d,J=8.5Hz) |
| | —CH₂CH₂CH₂C(CH₃)₂NH₂ | H | 1 room temp. | UV λ$_{max\ nm}^{H_2O}$: 255, 300 IR$_{max}^{KBr}$(cm⁻¹): 3400, 1780, 1625, 1547, 1365 |
| 17 | ⌬—NHPNZ | PNB | 5 145° C. | IR$_{max}^{film}$(cm⁻¹): 3350, 1780, 1705, 1600, 1510, 1342, 1310, 1255, 1038, 845 NMRδ(CDCl₃): 3.52(1H,dd,J=2 and 16Hz), 3.77(1H,dd,J=4 and 16Hz), 5.19(2H,s), 5.22(1H,d,J=14Hz), 5.45(1H,d,J=14Hz), 5.62(1H,dd, J=2 and 4Hz), 7.50(2H,d,J=9Hz), 7.63(2H,d,J=9Hz), 8.23(4H,d, J=9Hz) |
| | ⌬—NH₂ | H | 1 room temp. | IR$_{max}^{KBr}$(cm⁻¹): 1765, 1620, 1360, 1080 UV λ$_{max\ nm}^{H_2O}$: 255, 300 |
| 18 | ⌬—CH₂NHPNZ | PNB | 5 145° C. | IR$_{max}^{film}$(cm⁻¹): 3375, 1780, 1710, 1605, 1520, 1345, 1310, 1010, 852 NMRδ(CDCl₃): 3.50(1H,dd,J=2 and 16Hz), 3.77(1H,dd,J=4 and 16Hz), 5.20(2H,s), 5.22(1H,d, J=14Hz), 5.45(1H,d,J=14Hz), 5.62(1H,dd,J=2 and 4 Hz), 7.50 (2H,d,J=9Hz), 7.63(2H,d,J=9Hz), 8.20(4H,d,J=9Hz) |
| | ⌬—CH₂NH₂ | H | 1 room temp. | IR$_{max}^{KBr}$(cm⁻¹): 1775, 1627, 1590, 1510, 1380, 1198, UV λ$_{max\ nm}^{H_2O}$: 255, 300 |
| 19 | ⌬—NPNZ | PNB | 8 145° C. | IR$_{max}^{CHCl_3}$(cm⁻¹): 1785, 1700, 1605, 1568, 1520, 1440, 1347, 1313, 1119, 1075, 1010, 850 NMRδ(CDCl₃): 3.56(1H,dd,J=2 and 16Hz), 3.79(1H,dd,J=4 and 16Hz), 5.23(2H,s,), 5.23(1H,d,J=14Hz), 5.46(1H,d,J=14Hz), 5.61(1H,dd, J=2 and 4Hz), 7.46(2H,d,J= 8.5Hz), 7.64(2H,d,J=8.5Hz), 8.23(4H,d,J=8.5Hz) |
| | ⌬—NH | H | 1 room temp. | IR$_{max}^{KBr}$(cm⁻¹): 1750, 1585, 1350 |

-continued

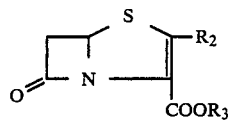

| Example No. | R₂ | R₃ | Reaction time (hr.) & Temperature | Spectral Data |
|---|---|---|---|---|
| 20 | —CH₂—⟨NPNZ⟩ | PNB | 4<br>130° C. | IR$_{max}^{film}$(cm$^{-1}$): 1780, 1695, 1600, 1566, 1510, 1342, 1205, 1110, 1005, 845<br>NMRδ(CDCl₃): 3.54(1H,dd,J=2 and 16.5Hz), 3.77(1H,dd,J=4 and 16.5Hz), 5.22(2H,s), 5.22(1H,d, J=14Hz), 5.42(1H,d,J=14Hz), 5.66(1H,dd,J=2 and 4Hz), 7.52 (2H,d,J=9Hz), 7.62(2H,d,J=9Hz), 8.22(4H,d,J=9Hz) |
|  | —CH₂—⟨NH⟩ | H | 1<br>room temp. | UV λ$_{max\ nm}^{H2O}$: 258, 302 |
| 21 | —CH=⟨NPNZ⟩ | PNB | 5.5<br>111° C. | NMRδ(CDCl₃): 5.23(1H,d,J=14Hz), 5.25(2H,s) 5.43(1H,d,J=14Hz), 5.64(1H,dd, J=2 and 4Hz), 6.68(1H,s,), 7.52 (2H,d,J=8.5Hz), 7.62(2H,d,J= 8,5Hz), 8.22(4H,d,J=8.5Hz) |
|  | —CH=⟨NH⟩ | H | 1<br>room temp. | IR$_{max}^{KBr}$(cm$^{-1}$): 1765, 1630, 1560, 1365<br>UV λ$_{max\ nm}^{H2O}$: 258, 303 |
| 22 | —SCH₂—⟨NPNZ⟩ | PNB | 6<br>140° C. | IR$_{max}^{CHCl3}$(cm$^{-1}$): 1790, 1686, 1605, 1520, 1348, 1323, 1230, 1110, 845<br>NMRδ(CDCl₃): 3.57(1H,dd,J=2 and 16Hz), 3.77(1H,dd,J=3.5 and 16Hz), 5.20(2H,s), 5.23(1H,d, J=14Hz), 5.43(1H,d,J=14Hz), 5.70(1H,dd,J=2 and 3.5Hz), 7.48(2H,d,J=9Hz), 7.60(2H,d, J=9Hz), 8.17(4H,d,J=9Hz) |
|  | —SCH₂—⟨NH⟩ | H | 1<br>room temp. | IR$_{max}^{KBr}$(cm$^{-1}$): 1770, 1575, 1365<br>UV λ$_{max\ nm}^{H2O}$: 250, 320 |
| 23 | —CH₂CH₂COO—ONB | PNB | 7<br>111° C. | IR$_{max}^{CHCl3}$ 1790, 1743, 1712, 1608, 1577, 1523, 1345, 1314, 1260, 1192, 1163, 1133, 853<br>NMRδ(CDCl₃): 2.68(2H,m), 3.14 (2H,m), 3.54(1H,dd,J=2 and 16Hz), 3.74(1H,dd,J=4 and 16Hz), 5.24(1H,d,J=14Hz), 5.43(1H,d, J=14Hz), 5.54(2H,s), 5.66(1H, dd,J=2 and 4Hz), 7.63(2H,d,J= 9Hz), 8.19(2H,d,J=9Hz) |
|  | —CH₂CH₂COONa | Na | 1<br>room temp. | KR$_{max}^{KBr}$(cm$^{-1}$): 1740, 1575, 1370<br>UV λ$_{max\ nm}^{H2O}$: 240(sh), 302 |
| 24 | —CH=CH—C(CH₃)₂CH₂NHPNZ | PNB | 2.5<br>111° C. | IR$_{max}^{film}$(cm$^{-1}$): 3370, 1775, 1705, 1600, 1340, 1305, 1235, 1070, 1038, 1003, 842<br>NMRδ(CDCl₃): 1.09(6H,s), 3.18 (2H,d,J=6.5Hz), 3.53(1H,dd, J=2 and 16Hz), 3.77(1H,dd,J= 4 and 16Hz), 5.20(2H,s), 5.59 (1H,dd,J=2 and 4Hz), 6.03(1H, d,J=16Hz), 7.29(1H,d,J=16Hz), 7.51(2H,d,J=9Hz), 7.65(2H,d, J=9Hz), 8.22(4H,d,J=9Hz) |
|  | —CH=CHC(CH₃)₂CH₂NH₂ | H | 1<br>room temp. | IR$_{max}^{KBr}$(cm$^{-1}$): 1763, 1620, 1570, 1550, 1356, 1285 |

-continued

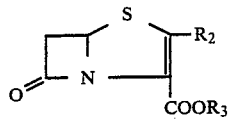

| Example No. | $R_2$ | $R_3$ | Reaction time (hr.) & Temperature | Spectral Data |
|---|---|---|---|---|
| | | | | UV $\lambda_{max\ nm}^{H2O}$: 257, 330 |
| 25 | —⟨phenyl⟩—CH$_2$CH$_2$NHPNZ | PNB | 6<br>110° C. | IR$_{max}^{Nujol}$(cm$^{-1}$): 3350, 1783, 1705, 1610, 1518, 1350, 1278, 1185, 840<br>NMRδ(CDCl$_3$): 2.85(2H,t,J=6.5Hz), 3.47(2H,t,J=6.5Hz), 3.65(1H,dd, J=2 and 16Hz), 3.83(1H,dd,J= 4 and 16Hz), 5.20(4H,s,), 5.78 (1H,dd,J=2 and 4Hz), 8.13(2H, d,J=9Hz), 8.19(2H,d,J=9Hz) |
| | —⟨phenyl⟩—CH$_2$CH$_2$NH$_2$ | H | 1<br>room temp. | IR$_{max}^{KBr}$(cm$^{-1}$): 1772, 1600, 1370<br>UV $\lambda_{max\ nm}^{H2O}$: 322 |
| 26 | —⟨phenyl⟩—NHPNZ | PNB | 4<br>145° C. | IR$_{max}^{Nujol}$(cm$^{-1}$): 3350, 1780, 1720, 1700, 1605, 1590, 1515, 1460, 1347, 1222, 840<br>NMRδ(CDCl$_3$): 3.63(1H,dd,J=2 and 16Hz), 3.84(1H,dd,J=4 and 16Hz), 5.15(1H,d,J=14Hz), 5.25(1H,d,J=14Hz), 5.30(2H,s), 5.75(1H,dd,J=2 and 4Hz), 6.53 (1H,bs), 7.56(2H,d,J=8.5Hz), 8.13(2H,d,J=8.5Hz), 8.23(2H, d,J=8.5Hz) |
| | —⟨phenyl⟩—NH$_2$ | Na | 1<br>room temp. | IR$_{max}^{KBr}$(cm$^{-1}$): 1760, 1605, 1380, 1295, 1080<br>UV $\lambda_{max\ nm}^{H2O}$: 290, 330 |
| 27 | —⟨phenyl, CH$_2$NHPNZ meta⟩ | PNB | 5<br>120° C. | IR$_{max}^{film}$: 3375, 1780, 1720, 1605, 1510, 1343, 1240, 1190, 1155, 1100, 1040, 850<br>NMRδ(CDCl$_3$): 3.63(1H,dd,J=2 and 16Hz), 3.82(1H,dd,J=4 and 16Hz), 4.33(2H,d,J=6.5Hz), 5.19(4H,s), 5.75(1H,dd,J=2 and 4 Hz), 8.05 (2H,d,J=9Hz), 8.13(2H,d,J=9Hz) |
| | —⟨phenyl, CH$_2$NH$_2$ meta⟩ | H | 1<br>room temp. | IR$_{max}^{KBr}$(cm$^{-1}$): 1760, 1580, 1355<br>UV $\lambda_{max\ nm}^{H2O}$: 322 |
| 28 | —⟨phenyl, OPNZ, OPNZ⟩ | PNB | 3<br>110° C. | IR$_{max}^{CHCl_3}$(cm$^{-1}$): 1780, 1718, 1610, 1525, 1350, 1318, 1250<br>NMRδ(CDCl$_3$): 3.68(1H,dd,J=2 and 16.5Hz), 3.84(1H,dd,J=4 and 16.5Hz), 5.13(1H,d,J=14Hz), 5.26(1H,d,J=14Hz), 5.33(4H,s), 5.79(1H,dd,J=2 and 4Hz), 8.19 (2H,d,J=9Hz), 8.16(4H,d,J=9Hz) |
| | —⟨phenyl, OH, OH⟩ | Na | 1<br>room temp. | IR$_{max}^{KBr}$(cm$^{-1}$): 1755, 1590, 1507, 1292<br>UV $\lambda_{max\ nm}^{H2O}$: 282, 320 |

-continued

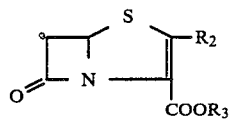

| Example No. | $R_2$ | $R_3$ | Reaction time (hr.) & Temperature | Spectral Data |
|---|---|---|---|---|
| 29* | ![phenyl-COOH] | PNB | 5<br>111° C. | $IR_{max}^{Nujol}(cm^{-1})$: 1780, 1708, 1612, 1530, 1353, 1320, 1281<br>NMRδ(DMSO—$d_6$): 3.71(1H,dd,J=2 and 15Hz), 3.97(1H,dd,J=4 and 16.5Hz), 5.37(2H,s,),5.93(1H, dd,J=2 and 4Hz), 9.18(1H,s) |
|  | ![phenyl-COONa] | Na | 1<br>room temp. | $IR_{max}^{KBr}(cm^{-1})$: 1755, 1590, 1372, 1290<br>$UV_{max\ nm}^{H2O}$250, 330 |
| 30 | ![4-pyridyl] | PNB | 3<br>111° C. | $IR_{max}^{film}(cm^{-1})$: 1785, 1713, 1600, 1568, 1515, 1342, 1305, 1175, 1112, 1015<br>NMRδ(CDCl$_3$): 3.68(1H,dd,J=2 and 16Hz), 3.83(1H,dd,J=4 and 16Hz), 5.14(1H,d,J=13.5Hz), 5.29(1H,d,J=13.5Hz), 5.85(1H, dd,J=2 and 4Hz), 8.13(2H,d, J=9Hz), 8.61(2H,m) |
| 31 | ![3-pyridyl] | PNB | 3<br>111° C. | $IR_{max}^{CHCl_3}$: 1792, 1718, 1602, 1522, 1435, 1347, 1310, 1172, 1119<br>NMRδ(CDCl$_3$): 3.66(1H,dd,J=2 and 16Hz), 3.81(1H,dd,J=3.5 and 16Hz), 5.14(1H,d,J=14Hz), 5.25(1H,d,J=14Hz), 5.78(1H,dd, J=2 and 3.5Hz), 8.09(2H,d,J= 9Hz), 8.64(2H,m) |
|  | ![3-pyridyl] | H | 1<br>room temp. | $IR_{max}^{KBr}(cm^{-1})$: 1765, 1583, 1318, 1285 |

*The compound of example 29 was prepared by the following procedure.
4-(4-Carboxybenzoylthio)-1-p-nitrobenzyloxycarbonyl-triphenylphosphoranylidenemethyl-2-azetidinone (704 mg) and bis(trimethylsilyl)acetamide (BSA) (610 mg) in tetrahydrofuran (15 ml) was refluxed for 0.5 hour, and the mixture was evaporated in vacuo to give the corresponding silylated compound. Then, the resulting silylated compound was refluxed in toluene (30 ml) for 3 hours under nitrogen atmosphere, and the mixture was evaporated in vacuo to give an oily residue which was then purified by silica gel chromatography to give 2-(4-carboxyphenyl)penem-3-carboxylic acid p-nitrobenzyl ester.

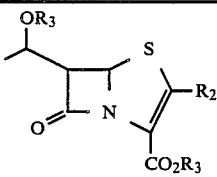

| Example No. | $R_2$ | $R_3$ | Reaction time (hr.) & Temperature | Spectral Data |
|---|---|---|---|---|
| 32 | —SCH$_2$C(CH$_3$)$_2$CH$_2$NHPNZ<br>trans | PNB | 4<br>145° C. | $IR_{max}^{CHCl_3}(cm^{-1})$: 1790, 1728, 1608, 1518, 1347, 1260, 1110, 1015, 850<br>NMRδ(CDCl$_3$): 1.03(6H,s), 1.49 (3H,d,J=6Hz), 2.98(2H,s), 3.17(2H,d,J=6.5Hz), 3.90 (1H, dd,J=1.5 and 8Hz), 5.20(2H,s), 5.20(1H,d,J=14Hz), 5.23(2H,s), 5.45(1H,d,J=14Hz), 5.62(1H,d,J=1.5Hz), 7.50(4H, d,J=9Hz), 7.58(2H,d,J=9Hz), 8.15(6H,d,J=9Hz) |

-continued

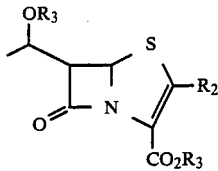

| Example No. | R₂ | R₃ | Reaction time (hr.) & Temperature | Spectral Data |
|---|---|---|---|---|
|  | —SCH₂C(CH₃)₂CH₂NH₂<br>trans | H | 1<br>room temp. | IR$_{max}^{KBr}$(cm$^{-1}$): 1750, 1580, 1370, 1290, 1080<br>$\lambda_{max\ nm}^{H2O}$: 250, 320 |
| 33 | —SCH₂C(CH₃)₂CH₂NHPNZ<br>cis | PNB | 4<br>145° C. | IR$_{max}^{CHCl3}$(cm$^{-1}$): 3625, 1786, 1723, 1605, 1510, 1342, 1318, 1250, 1159, 1108, 1008, 845<br>NMRδ(CDCl₃): 1.04(6H,s), 1.59 (3H,d,J=6Hz), 3.05(2H,s), 3.17(2H,d,J=7Hz), 4.09(1H,dd, J=4 and 10Hz), 5.18(2H,s), 5.26(2H,s), 5.43(1H,d,J=14Hz), 5.72(1H,d,J=4Hz) |
|  | —SCH₂C(CH₃)₂CH₂NH₂<br>cis | H | 1<br>room temp. | $\lambda_{max\ nm}^{H2O}$: 250, 317 |
| 34 | —CH₂CH₂C(CH₃)₂NHPNZ<br>trans | PNB | 3.5<br>137° C. | IR$_{max}^{CHCl3}$(cm$^{-1}$): 1782, 1720, 1606, 1522, 1347, 1260, 1205, 903<br>NMRδ(CDCl₃): 1.32(6H,s), 1.49 (2H,d,J=6.5), 1.93(2H,t,J=8), 3.88(1H,dd,J=8 and 1.5), 4.93(1H,bs), 5.14(2H,s), 5.25 (2H,s), 5.56(1H,d,J=1.5) 8.20(4H,d,J=9), 8.22(2H,d, J=9) |
|  | —CH₂CH₂C(CH₃)₂NH₂<br>trans | H | 1<br>room temp. | UV $\lambda_{max\ nm}^{H2O}$: 258, 302 |
| 35 | —CH= (piperidinyl)NPNZ<br>trans | PNB | 4<br>145° C. | IR$_{max}^{CHCl3}$(cm$^{-1}$): 1788, 1748, 1695, 1608, 1520, 1434, 1346, 1314, 1263, 1170, 1110, 1010, 848<br>NMRδ(CDCl₃): 1.51(3H,d,J=6.5Hz), 3.90(1H,dd,J=1.5 and 8Hz), 5.24(4H,s), 5.44(1H,d,J=13.5Hz), 5.61(1H,d,J=1.5Hz), 6.85(1H,Bs), 7.52(4H,d,J=8.5Hz), 7.61(2H,d, J=8.5Hz), 8.20(2H,d,J=8.5Hz), 8.22(4H,d,J=8.5Hz) |
|  | —CH= (piperidinyl)NH<br>trans | H | 1<br>room temp. | $\lambda_{max\ nm}^{H2O}$: 258, 315 |
| 36 | H, (piperidinyl)NPNZ<br>trans | PNB | 9.5<br>111° C. | IR$_{max}^{CHCl3}$(cm$^{-1}$): 1785, 1708, 1608, 1578, 1522, 1400, 1346, 1313, 1257, 1165, 1133, 1010, 847<br>NMRδ(CDCl₃): 1.55(3H,d,J=6.5Hz), 3.85(1H,dd,J=1.5 and 8.0Hz), 5.31(2H,s), 5.33(2H,s), 5.36 (1H,d,J=13.5Hz), 5.60(1H,d,J= 1.5Hz), 6.78(1H,Bd,J=1.5Hz), 7.48(4H,d,J=8.5Hz), 7.55(2H,d, J=8.5Hz), 8.15(6H,d,J=8.5Hz) |
|  | H, (piperidinyl)NH<br>trans | H | 1<br>room temp. | UV $\lambda_{max\ nm}^{H2O}$: 258, 313 |

-continued

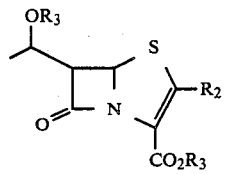

| Example No. | R₂ | R₃ | Reaction time (hr.) & Temperature | Spectral Data |
|---|---|---|---|---|
| 37 | H—C(=)—CH₂—NPNZ (cyclohexyl), trans | PNB | 7<br>111° C. | $IR_{max}^{CHCl_3}(cm^{-1})$: 1785, 1745, 1708, 1608, 1578, 1523, 1400, 1348, 1315, 1260, 1136, 1010, 848<br>NMRδ(CDCl₃): 1.49(3H,d,J=6.5Hz), 3.82(1H,dd,J=1.5 and 8Hz), 5.18(2H,s), 5.22(2H,s), 5.37 (1H,d,J=14Hz), 5.57(1H,d,J= 1.5Hz), 6.82(1H,Bd,J=2.5Hz), 7.49(4H,d,J=8.5Hz), 7.56(2H,d, J=8.5Hz), 8.13(6H,d,J=8.5Hz) |
|  | H—C(=)—CH₂—NH (cyclohexyl), trans | H | 1<br>room temp. | UV $\lambda_{max\ nm}^{H2O}$: 258, 313 |
| 38 | —CH=CH—(cyclohexyl)—N—PNZ, trans | PNB | 10<br>110° C. | $IR_{max}^{CHCl_3}(cm^{-1})$: 1788, 1730(sh), 1702, 1608, 1523, 1440, 1348, 1320, 1210, 1173, 1110, 1040, 850<br>NMRδ(CDCl₃): 1.52(3H,d,J=6.5), 3.92(1H,dd,J=1.5 and 7.5) 5.26(4H,s). 5.58(1H,d,J=1.5), 6.49(1H,d,J=16), 7.53(4H,d, J=9), 7.63(2H,d,J=9), 8.20 (6H,d,J=9) |
|  | —CH=CH—(cyclohexyl)—NH, trans | H | 1<br>room temp. | UV $\lambda_{max\ nm}^{H2O}$: 276, 320(sh), 340(sh) |
| 39 | —C(CH₃)=C—(cyclohexyl)—NPNZ, 5,6-trans (E,Z: mixture) | PNB | 9.5<br>137° C. | $IR_{max}^{CHCl_3}(cm^{-1})$: 1785, 1745, 1693, 1608, 1520, 1435, 1345, 1260, 1203, 1132, 1100, 850<br>NMRδ(CDCl₃): 1.50(3H,d,J=6.5), 1.90(3H,s), 5.22(2H,s), 5.25(2H,s), 5.58(½H,d,J=1.5), 5.72(½H,d,J=1.5), 8.22(6H, d,J=9) |
|  | —C(CH₃)=CH—(cyclohexyl)—NH, trans (E,Z:mixture) | H | 2.5<br>room temp. | UV $\lambda_{max\ nm}^{H2O}$: 257, 307 |
| 40 | —CH₂—(cyclohexyl)—NPNZ, trans | PNB | 10.5<br>111° C. | $IR_{max}^{CHCl_3}(cm^{-1})$: 1783, 1747, 1700, 1612, 1580, 1520, 1440, 1346, 1312, 1260, 1125, 1008, 848<br>NMRδ(CDCl₃): 1.49(3H,d,J=6.5Hz), 3.88(1H,dd,J=1.5 and 7.5Hz), 5.21(2H,s), 5.24(2H,s), 5.39 (1H,d,J=14Hz), 5.59(1H,d,J= 1.5Hz), 7.50(4H,d,J=9Hz), 7.58 (2H,d,J=9Hz), 8.21(6H,d,J=9Hz) |

-continued

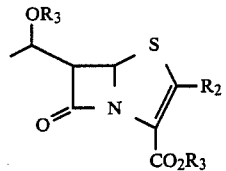

| Example No. | R₂ | R₃ | Reaction time (hr.) & Temperature | Spectral Data |
|---|---|---|---|---|
|  | —CH₂—[piperidine-NH] trans | H | 1 room temp. | UV $\lambda_{max\ nm}^{H_2O}$: 256, 302 |
| 41 | —CH₂CH₂—[piperidine-NPNZ] trans | PNB | 10.5 111° C. | IR$_{max}^{CHCl_3}$(cm$^{-1}$): 1790, 1750, 1695, 1612, 1582, 1527, 1447, 1350, 1320, 1265, 1170, 1148, 1018, 855<br>NMRδ(CDCl₃): 1.50(3H,d,J=6.5Hz), 3.90(1H,dd,J=1.5 and 8Hz), 5.21(2H,s), 5.25(2H,s), 5.41(1H,d,J=14Hz), 5.58(1H,d,J=1.5Hz), 7.51(4H,d,J=9Hz), 7.59(2H,d,J=9Hz), 8.22(6H,d,J=9Hz) |
|  | —CH₂CH₂—[piperidine-NH] trans | H | 1 room temp. | UV $\lambda_{max\ nm}^{H_2O}$: 258, 300 |
| 42 | —CH₂S—[piperidine-NPNZ] trans | PNB | 5 111° C. | IR$_{max}^{CHCl_3}$(cm$^{-1}$): 1788, 1745, 1705, 1610, 1580, 1527, 1445, 1350, 1267, 1252, 1113, 1010, 850<br>NMRδ(CDCl₃): 1.51(3H,d,J=6.5Hz), 5.21(2H,s), 5.25(2H,s), 5.42(1H,d,J=13.5Hz), 5.60(1H,d,J=1.5Hz), 7.51(4H,d,J=9Hz), 7.61(2H,d,J=9Hz), 8.22(6H,d,J=9Hz) |
|  | —CH₂S—[piperidine-NH] trans | H | 1 room temp. | UV $\lambda_{max\ nm}^{H_2O}$: 260, 307 |
| 43 | —SCH₂CH₃ [piperidine-NPNZ] trans | PNB | 10 137° C. | IR$_{max}^{CHCl_3}$(cm$^{-1}$): 1785, 1763, 1688, 1605, 1520, 1435, 1343, 1255, 1107, 845<br>NMRδ(CDCl₃): 1.51(3H,d,J=6.5), 3.93(1H,dd,J=1.5 and 8), 5.23(2H,s), 5.32(2H,s), 5.68(1H,d,J=1.5), 7.51(4H,d,J=8.5), 7.61(2H,d,J=8.5), 8.18(6H,d,J=8.5) |
|  | —SCH₂CH₂—[piperidine-NH] trans | H | 6 30° C. | UV $\lambda_{max\ nm}^{H_2O}(\epsilon)$: 254(5241), 323(7187) |

-continued

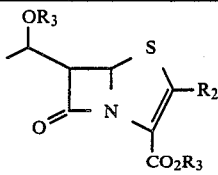

| Example No. | R₂ | R₃ | Reaction time (hr.) & Temperature | Spectral Data |
|---|---|---|---|---|
| | —SCH₂CH₂—[ring]—NPNZ  cis | PNB | 10  137° C. | IR$_{max}^{CHCl_3}$(cm$^{-1}$): 1785, 1740, 1687, 1605, 1520, 1346, 1200, 1158, 1108  NMRδ(CDCl₃): 1.61(3H,d,J=6), 4.11(1H,dd,J=4 and 10), 5.21 (2H,s), 5.26(2H,s), 5.44(1H, d,J=13.5), 5.77(1H,d,J=4), 7.50(2H,d,J=9), 7.54(2H,d,J= 9), 7.60(2H,d,J=9), 8.12(4H, d,J=9), 8.24(2H,d,J=9) |
| 44 | —SCH₂CH=[ring]=NPNZ  trans | PNB | 9  137° C. | IR$_{max}^{CHCl_3}$(cm$^{-1}$): 1790, 1746, 1690, 1610, 1520, 1440, 1350, 1327, 1260, 1220, 1114, 850  NMRδ(CDCl₃): 1.51(3H,d,J=6.5) 3.92(1H,dd,J=1.5 and 8), 5.24 (4H,s), 5.43(1H,d,J=13.5), 5.65(1H,d,J=1.5), 7.52(4H,d, J=8.5), 7.60(2H,d,J=8.5), 8.21 (6H,d,J=8.5) |
| | —SCH₂CH=[ring]=NH  trans | H | 4  30° C. | UV λ$_{max\ nm}^{H_2O}$(ε): 251(5757), 323 (7209) |
| | —SCH₂CH=[ring]=NPNZ  cis | PNB | 9  137° C. | IR$_{max}^{CHCl_3}$(cm$^{-1}$): 1790, 1745, 1693, 1610, 1520, 1435, 1342, 1220, 1160, 1110, 850  NMRδ(CDCl₃): 1.61(3H,d,J=6), 5.24 (4H,s), 5.76(1H,d,J=4), 8.21 (6H,d,J=9) |
| 45 | —SCH₂—[ring]—NPNZ  trans | PNB | 9.5  137° C. | IR$_{max}^{CHCl_3}$(cm$^{-1}$): 1787, 1743, 1695, 1603, 1520, 1342, 1260, 1103  NMRδ(CDCl₃): 1.50(3H,d,J=6), 5.23(4H,s), 5.62(1H,d,J=1.5) 7.49(4H,d,J=9), 7.57(2H,d, J=9), 8.16(6H,d,J=9) |
| | —SCH₂—[ring]—NH  trans | H | 3  30° C. | UV λ$_{max\ nm}^{H_2O}$(ε): 255(4662) 323 (6122) |
| | —SCH₂—[ring]—NPNZ  cis | PNB | 9.5  137° C. | IR$_{max}^{CHCl_3}$(cm$^{-1}$): 1790, 1748, 1700, 1610, 1525, 1440, 1350, 1250, 1163, 1110, 823  NMRδ(CDCl₃): 1.58(3H,d,J=6.5), 4.12(1H,dd,J=4 and 10), 5.27 (4H,s), 5.71(1H,d,J=4), 7.48 (4H,d,J=8.5), 7.54(2H,d,J= 8.5), 8.13(6H,d,J=8.5) |
| 46 | —[ring]—CH₂NHPNZ  trans | PNB | 6.5  145° C. | IR$_{max}^{CHCl_3}$(cm$^{-1}$): 1786, 1750(sh), 1720, 1610, 1570, 1520, 1450, 1380, 1347, 1314, 1260, 1210, 1172, 1135, 1110, 1013, 850  NMRδ(CD₃COCD₃): 1.46(3H,d,J=6Hz), 4.05(1H,dd,J=1.5 and 6Hz), 5.18(2H,s), 5.28(2H,s), 5.41 (1H,d,J=13.5Hz), 5.66(1H,d, J=1.5Hz), 8.12(6H,d,J=8.5Hz) |

-continued

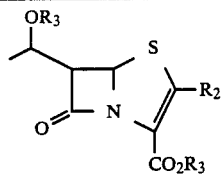

| Example No. | R₂ | R₃ | Reaction time (hr.) & Temperature | Spectral Data |
|---|---|---|---|---|
|  | —⟨cyclohexyl⟩—CH₂NH₂ trans | H | 4.5 30° C. | IR$_{max}^{KBr}$(cm$^{-1}$): 1760, 1555, 1360 UV $\lambda_{max\ nm}^{H2O}(\epsilon)$: 258(3846), 303 (5291) |
| 47 | —⟨cyclohexyl⟩—CH₂CH₂NHPNZ trans | PNB | 9.5 138° C. | IR$_{max}^{CHCl_3}$(cm$^{-1}$): 1785, 1723, 1608, 1517, 1448, 1347, 1252, 1212, 1155, 846 NMRδ(CDCl₃): 1.44(3H,d,J=6.5Hz) 5.19(2H,s), 5.25(2H,s) 8.20(6H,d,J=8.5Hz) |
|  | —⟨cyclohexyl⟩—CH₂CH₂NH₂ trans | H | 3 room temp. | UV $\lambda_{max}^{H2O}$ nm: 258, 302 |
| 48 | —⟨cyclohexyl⟩—NHPNZ trans | PNB | 9 145° C. | IR$_{max}^{CHCl_3}$(cm$^{-1}$): 3440, 1785, 1745(sh), 1713, 1608, 1570, 1520, 1345, 1312, 1255, 1170, 1037, 850 NMRδ(CDCl₃): 1.49(3H,d,J=6.5Hz), 4.67(1H,d,J=5Hz), 5.18(2H,s), 5.24(2H,s), 5.55(1H,d,J= 1.5Hz), 7.51(4H,d,J=8.5Hz), 7.59(2H,d,J=8.5Hz), 8.21(6H, d,J=8.5Hz) |
|  | —⟨cyclohexyl⟩—NH₂ trans | H | 4 30° C. | IR$_{max}^{KBr}$(cm$^{-1}$): 1758, 1568, 1360 UV $\lambda_{max\ nm}^{H2O}$: 258, 303 |
| 49 | —⟨cyclohexyl⟩—CH₂OPNZ trans | PNB | 8 137° C. | IR$_{max}^{CHCl_3}$(cm$^{-1}$): 1785, 1743, 1713 1612, 1523, 1345, 1315, 1255, 1205, 1190, 850 NMRδ(CDCl₃): 1.49(3H,d,J=6.5), 5.24(4H,s), 5.54(1H,d,J=1.5), 7.52(2H,d,J=8.5), 7.55(2H,d, J=8.5), 7.62(2H,d,J=8.5), 8.22(6H,d,J=8.5) |
|  | —⟨cyclohexyl⟩—CH₂OH trans | Na | 2 room temp. | UV $\lambda_{max\ nm}^{H2O}$: 256, 302 |
| 50 | —⟨cyclohexyl⟩ | PNB | 11 137° C. | IR$_{max}^{CHCl_3}$(cm$^{-1}$): 1780, 1740, 1705, 1605, 1560, 1520, 1345, 1260, 1202, 900 NMRδ(CDCl₃): 1.49(3H,d,J=6.5) 3.86(1H,dd,J=8 and 1.5), 5.24 (4H,s), 5.52(1H,d,J=1.5), 7.52(2H,d,J=8.5), 7.61(4H,d, J=8.5), 8.21(6H,d,J=8.5) |
|  |  | H | 2 room temp. | UV $\lambda_{max}^{MeOH}$ nm: 245(sh), 315 |

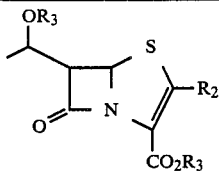

| Example No. | R2 | R3 | Reaction time (hr.) & Temperature | Spectral Data |
|---|---|---|---|---|
| 51 | —S-cyclohexyl, trans | PNB | 12.5 137° C. | IR$_{max}^{CHCl_3}$(cm$^{-1}$): 1788, 1745, 1688, 1607, 1521, 1350, 1325, 1265, 1205, 1110, 847 NMRδ(CDCl$_3$): 1.50(3H,d,J=6), 3.90(1H,dd,J=1.5 and 8), 5.25 (2H,s), 5.43(1H,d,J=14), 5.64 (1H,d,J=1.5), 7.53(2H,d,J= 8.5), 7.61(2H,d,J=8.5), 8.20 (2H,d,J=8.5), 8.22(2H,d,J=8.5) |
|  | —S-cyclohexyl, trans | Na | 2 room temp. | UV λ$_{max\ nm}^{MeOH}$: 260, 322 |
|  | —S-cyclohexyl, cis | PNB | 12.5 137° C. | IR$_{max}^{CHCl_3}$(cm$^{-1}$): 1780, 1738, 1690, 1600, 1515, 1340, 1315, 1243, 1155, 1103, 840 NMRδ(CDCl$_3$); 1.61(3H,d,J=6.5), 4.10(1H,dd,J=4 and 10), 5.28 (2H,s), 5.37(1H,d,J=14), 5.75 (1H,d,J=4), 7.55(2H,d,J=8.5), 7.61(2H,d,J=8.5), 8.12(2H,d, J=8.5), 8.24(2H,d,J=8.5) |
| 52 | —CH=CH—CH$_2$—CH$_2$NHPNZ | PNB | 1.5 138° C. | NMRδ(CDCl$_3$): 1.51(3H,d,J=6.5Hz), 2.47(2H,q,J=7Hz), 3.35(2H,q,J=6Hz), 3.88(1H,dd,J=1.5 and 8Hz), 5.19(2H,s), 5.25(2H,s), 5.51(1H,d,J=1.5Hz), 6.03(H,dt,J=15.5 and 7Hz), 8.20(4H,d, J=9Hz), 8.22(2H,d,J=9Hz) |
|  | —CH=CH—CH$_2$—CH$_2$NH$_2$ | H | 3 room temp. | UV λ$_{max}^{H2O}$ nm: 258, 321 NMRδ(D$_2$O): 1.29(3H,d,J=6.5Hz) 7.27(1H,d,J=15.5Hz) |

EXAMPLE 53

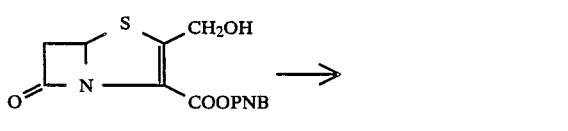

To a mixture of 2-hydroxymethyl-penem-3-carboxylic acid p-nitrobenzyl ester (168 mg) and triethylamine (60 mg) in dichloromethane (4 ml) was added methoxyacetyl chloride (0.05 ml) with ice-cooling under nitrogen atmosphere and stirred for 1 hour at the same temperature. The reaction mixture was diluted with dichloromethane, washed successively with aqueous sodium bicarbonate and water, dried over anhydrous sodium sulfate and evaporated to give an oily residue which was then purified by silica gel chromatography to give 2-methoxyacetoxymethyl-penem-3-carboxylic acid p-nitrobenzyl ester.

IR$_{max}^{film}$(cm$^{-1}$): 1780, 1725, 1604, 1580, 1515, 850.
NMRδ(CDCl$_3$): 3.48(3H, s), 3.62(1H, dd, J=2 and 17 Hz), 5.72(1H, dd, J=2 and 4 Hz), 3.79(1H, dd, J=4 and 17 Hz), 7.65(2H, d, J=8.5 Hz), 4.10(2H, s), 5.32(2H, s), 8.25(2H, d, J=8.5 Hz).

EXAMPLE 54

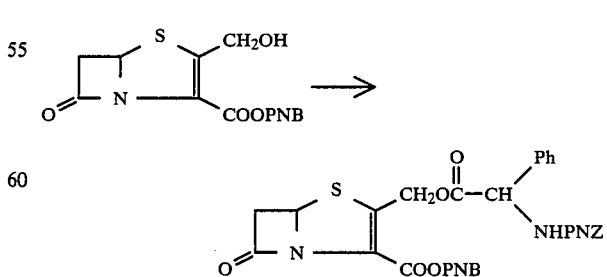

A mixture of 2-hydroxymethyl-penem-3-carboxylic acid p-nitrobenzyl ester (152 mg) and dicyclohexylcarbodiimide (DCC) (120 mg) in tetrahydrofuran (15 ml)

was stirred for 30 minutes under nitrogen atmosphere. The reaction mixture was filtered and the filtrate was evaporated to give an oily residue which was then purified by silica gel chromatography to give 2-N-p-nitrobenzyloxycarbonylphenylglycyloxymethyl-penem-3-carboxylic acid-p-nitrobenzyl ester.

IR$_{max}^{CHCl_3}$(cm$^{-1}$): 3440, 1795, 1725, 1606, 1520, 1350, 1319, 1162, 1053, 906.

NMRδ(CDCl$_3$): 3.51(1H, dd, J=2 and 16.5 Hz), 3.72(1H, dd, J=3.5 and 16.5 Hz), 5.17(2H, s), 5.41(2H, s), 7.33(5H, s), 7.55(2H, d, J=9 Hz), 8.17(4H, d, J=9 Hz).

EXAMPLE 55

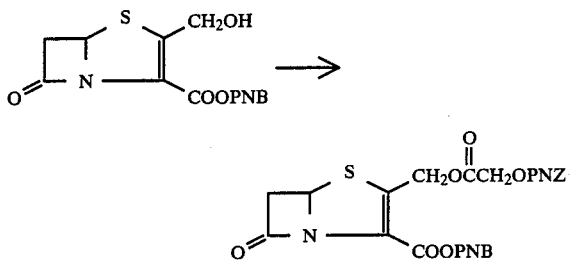

(a) To a mixture of glycolic acid (760 mg) and triethylamine (1.1 g) in tetrahydrofuran (20 ml) was added p-nitrobenzyl chloroformate (2.26 g) with ice-cooling and the resulting mixture was stirred for 1 hour at room temperature. The reaction mixture was diluted with ethyl acetate, washed successively with diluted hydrochloric acid and water, dried over anhydrous sodium sulfate and evaporated to give p-nitrobenzyloxycarbonyloxyacetic acid.

(b) A mixture of p-nitrobenzyloxycarbonyloxyacetic acid (300 mg) and 1,1-dichlorodimethyl ether (1 ml) in ethyl acetate (7.5 ml) was refluxed for 5 hours. The reaction mixture was evaporated to give p-nitrobenzyloxycarbonyloxyacetyl chloride, which was then added to a solution of 2-hydroxymethyl-penem-3-carboxylic acid p-nitrobenzyl ester (168 mg) and triethylamine (0.1 ml) in dichlormethane (10 ml) with ice-cooling, followed by stirring for 1 hour. The reaction mixture was treated by the procedure similar to that described in Example 53 to give 2-p-nitrobenzyloxycarbonyloxyacetoxymethyl-penem-3-carboxylic acid p-nitrobenzyl ester.

IR$_{max}^{CHCl_3}$(cm$^{-1}$): 1790, 1752, 1705, 1600, 1519, 1342, 1312, 1277, 1260, 1178, 902.

NMRδ(CDCl$_3$): 3.64(1H, dd, J=2 and 16.5 Hz), 3.82 (1H, dd, J=4 and 16.5 Hz), 4.70(2H, s), 5.30(4H, s), 5.67(1H, dd, J=2 and 4 Hz), 7.52(2H, d, J=9 Hz), 7.57(2H, d, J=9 Hz), 8.17(4H, d, J=9 Hz).

EXAMPLE 56

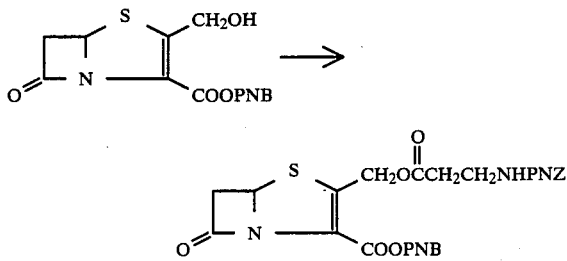

2-(2-N-p-Nitrobenzyloxycarbonylaminopropionyl-)oxymethyl-penem-3-carboxylic acid p-nitrobenzyl ester was prepared from 2-hydroxymethyl-penem-3-carboxylic acid p-nitrobenzyl ester and 3-N-p-nitrobenzyloxycarbonylaminopropionyl chloride by the procedure similar to that described in Example 53.

IR$_{max}^{film}$(cm$^{-1}$): 3380, 1782, 1710, 1602, 1575, 1512, 1341, 1062, 1000, 845.

NMRδ(CDCl$_3$): 2.85(2H, t, J=6 Hz), 3.44(2H, t, J=6 Hz), 3.60(1H, dd, J=2 and 16 Hz), 3.73(1H, dd, J=4 and 16 Hz), 5.13(1H, d, J=14 Hz), 5.16(2H, s), 5.21(1H, d, J=13 HZ), 5.41(1H, d, J=13 Hz), 5.44(1H, d, J=14 Hz), 5.64(1H, dd, J=2 and 4 Hz), 7.44(2H, d, J=9 Hz), 7.55(2H, d, J=9 Hz), 8.15(4H, d, J=9 Hz).

The starting material, 3-N-p-nitrobenzyloxycarbonylaminopropionyl chloride, was prepared by the following procedure.

To β-alanine (1.14 g) in 4N sodium hydroxide (7.8 ml) was added p-nitrobenzyl chloroformate (3 g) in dioxane (8 ml) with ice-cooling and stirred for 1 hour. The reaction mixture was filtered and the filtrate was neutralized with hydrochloric acid. The resulting precipitate was collected to give N-p-nitrobenzyloxycarbonyl-β-alanine, which was then converted into the corresponding acid chloride by reaction with thionyl chloride.

EXAMPLE 57

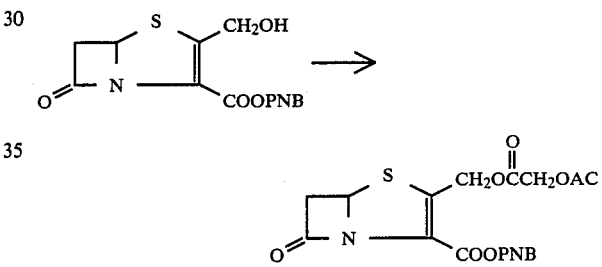

2-Acetoxyacetoxymethyl-penem-3-carboxylic acid-p-nitrobenzyl ester was prepared from 2-hydroxymethyl penem-3-carboxylic acid p-nitrobenzyl ester and acetoxyacetyl chloride by the procedure similar to that described in Example 53.

IR$_{max}^{film}$(cm$^{-1}$): 1780, 1730, 1600, 1575, 1515, 840.

NMRδ(CDCl$_3$): 2.17(3H, s), 3.65(1H, dd, J=2 and 16 Hz), 3.82(1H, dd, J=4 and 16 Hz), 4.65(2H, s), 5.21(1H, d, J=14 Hz), 5.27(1H, d, J=13 Hz), 5.44(1H, d, J=13 Hz), 5.56(1H, d, J=14 Hz), 5.74(1H, dd, J=2 and 4 Hz), 7.62(2H, d, J=8.5 Hz), 8.22(2H, d, J=8.5Hz).

EXAMPLE 58

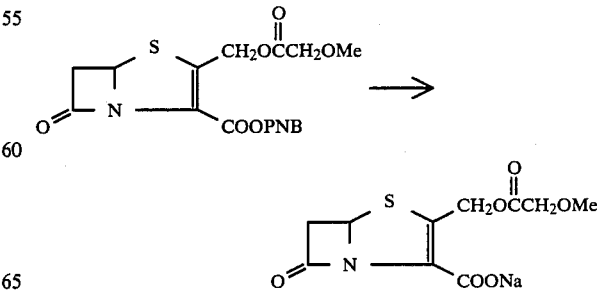

A mixture of 2-methoxyacetoxymethyl-penem-3-carboxylic acid p-nitrobenzyl ester (65 mg) and 5% palladium-charcoal (120 mg) in ethyl acetate (4.5 ml) and water (2 ml) was stirred under hydrogen atmosphere at room temperature for 1 hour. The catalyst was removed by filtration and washed with water. After addition of sodium bicarbonate (30 mg), the combined solution was concentrated to a volume of about 2 ml in vacuo, and chromatographed on Biogel P-2 (10 ml). Fractions eluted with water were collected and lyophilized to give 2-methoxyacetoxymethyl-penem-3-carboxylic acid sodium salt as a colorless powder.

$IR_{max}^{KBr}(cm^{-1})$: 1788, 1740, 1580, 1220.

UV $\lambda_{max\ nm}^{H2O}$: 255, 303.

EXAMPLE 59

The following compounds were prepared by the procedure similar to that described above.

| R | R7' | Starting Materials |
|---|---|---|
| H | -CH(NH2)-C6H5 | Compound described in Example 54 |
| Na | —CH2OH | Compound described in Example 55 |
| H | —CH2CH2NH2 | Compound described in Example 56 |
| Na | —CH2OAc | Compound described in Example 57 |

EXAMPLE 60

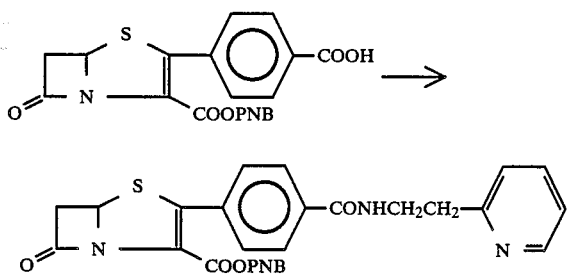

A mixture of 2-(4-carboxyphenyl)-penem-3-carboxylic acid p-nitrobenzyl ester (500 mg) and carbonyldiimidazole (210 mg) in tetrahydrofuran (10 ml) was stirred at room temperature for 6 hours. After addition of 2-(2-aminoethyl)pyridine (215 mg), the resulting mixture was stirred at room temperature for 3 hours, diluted with ethyl acetate, washed with water, dried over anhydrous sodium sulfate and evaporated to give a residue which was then purified by silica gel chromatography to give 2-(4-(2-pyridinylethylamino)carbonylphenyl)-penem-3-carboxylic acid p-nitrobenzyl ester.

$IR_{max}^{Nujol}(cm^{-1})$: 3350, 1795, 1712, 1642, 1520, 1345, 1278, 1180.

NMRδ(CDCl3): 3.10(2H, t, J=6 Hz), 5.08(1H, d, J=14 Hz), 5.25(1H, d, J=14 Hz,), 5.80(1H, m), 8.51(1H, m).

EXAMPLE 61

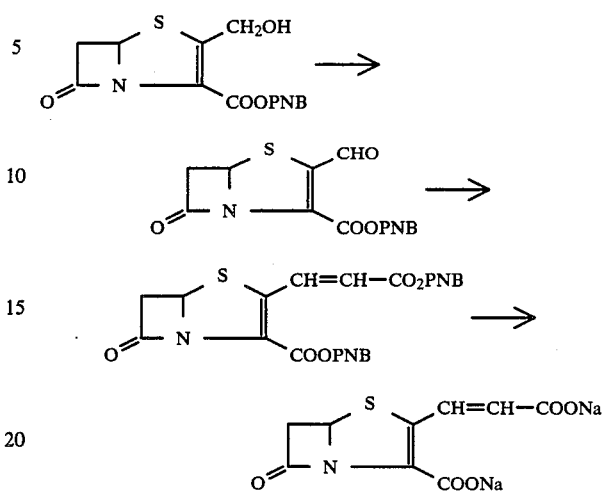

(a) To a solution of oxalyl chloride (0.5 ml) in dichloromethane (30 ml) was added dropwise dimethyl sulfoxide (0.85 ml) at −50° to −60° C. under nitrogen atmosphere. After stirring for 10 minutes, 2-hydroxymethyl-penem-3-carboxylic acid p-nitrobenzyl ester (1.68 g) in dichloromethane (30 ml) was added dropwise to the reaction mixture. The mixture was stirred for 15 minutes at −50° to −60° C. and finally triethylamine (3.5 ml) was added dropwise thereto, followed by stirring for 15 minutes. The reaction mixture was diluted with cooled water and extracted with ether. The ether extract was washed successively with diluted hydrochloric acid and water, dried over anhydrous sodium sulfate and evaporated to give 2-formyl-penem-3-carboxylic acid p-nitrobenzyl ester.

$IR_{max}^{CHCl3}(cm^{-1})$: 1800, 1720, 1665, 1520, 1350, 1312, 1050, 903.

NMRδ(CDCl3): 3.78(1H, dd, J=2 and 17 Hz), 3.86(1H, dd, J=4 and 17 Hz), 5.37(1H, d, J=14 Hz), 5.44(1H, d, J=14 Hz), 5.73(1H, dd, J=2 and 4 Hz), 7.63(2H, d, J=8.5 Hz), 8.23(2H, d, J=8.5 Hz), 10.41(1H, s).

(b) A mixture of 2-formyl-penem-3-carboxylic acid p-nitrobenzyl ester and p-nitrobenzyloxycarbonylmethylenetriphenylphosphoran (2.2 g) in tetrahydrofuran (200 ml) was refluxed for 15 minutes, cooled to room temperature and evaporated to give a residue which was then purified by silica gel chromatography to give 2-(2-(p-nitrobenzyloxycarbonyl)ethenyl)-penem-3-carboxylic acid p-nitrobenzyl ester.

$IR_{max}^{film}(cm^{-1})$: 1785, 1720, 1600, 1520, 1340, 1063, 1003, 845.

NMRδ(CDCl3): 3.63(1H, dd, J=2 and 16 Hz), 3.80(1H, dd, J=16 Hz), 5.28(2H, s), 5.67(1H, dd, J=2 and 3.5 Hz), 6.08(1H, d, J=16 Hz), 8.17(4H, d, J=9 Hz).

(c) A mixture of 2-[2-(p-nitrobenzyloxycarbonyl)ethenyl]-penem-3-carboxylic acid p-nitrobenzyl ester (140 mg) and 5% palladium-charcoal (260 mg) in ethylacetate (16 ml) and water (5 ml) was stirred under hydrogen atmosphere at room temperature for 1 hour. The catalyst was removed by filtration and washed with water. After addition of sodium bicarbonate (60 mg), the combined solution was concentrated to a volume of about 6 ml in vacuo, and the concentrate was chromatographed on Biogel P-2 (30 ml). Fractions eluted with water were collected and lyophilized to give 2-(2-carboxyethenyl)penem-3-carboxilic acid sodium salt as a colorless powder.

UV $\lambda_{max\ nm}^{H_2O}$: 255, 338.

EXAMPLE 62

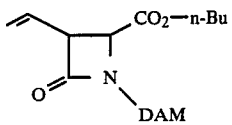

Di-p-anisylmethylamine (10 g) and n-butylglyoxylate (7.3 g) in toluene were azeotropically dehydrated to give a Schiff base. To the toluene solution (about 600 ml), crotonylchloride (5.1 g) in toluene (25 ml) were added dropwise at 70° C. over about 1 hour in the presence of triethylamine (6.2 g), followed by stirring for 2 hours. The reaction mixture was cooled, washed successively with water, 2N hydrochloric acid, aqueous sodium bicarbonate and again water, dried over anhydrous sodium sulfate and evaporated to give an oily residue which was then purified by silica gel chromatography to give 1-(di-p-anisylmethyl)-3-ethenyl-4-n-butoxycarbonyl-2-azetidinone.

$IR_{max}^{CHCl_3}(cm^{-1})$: 1758, 1615, 1252, 1180, 1030, 930, 825.

NMRδ(CDCl$_3$): 0.87(3H, br, t, J=6), 1.0-1.7(4H, m), 3.78(6H, s), 5.1-5.8(3H, m), 5.77(1H, s).

EXAMPLE 63

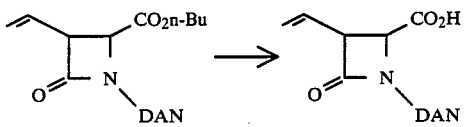

A solution of 1-(di-p-anysylmethyl)-3-ethyl-4-n-butoxycarbonyl-2-azetidinone (0.5 g) in 1N sodium hydroxide (1.2 ml), tetrahydrofuran (15 ml) and methanol (15 ml) was stirred for 2 hours at room temperature. After addition of 2N hydrochloric acid (0.7 ml), the reaction mixture was concentrated to a quarter of its original volume, diluted with water and extracted with diethyl ether. The ether extract was re-extracted with an aqueous alkaline solution. The aqueous alkaline layer was acidified with hydrochloric acid and extracted with diethyl ether. The ether extract was washed with water, dried over sodium sulfate and evaporated to give 1-(di-p-anisylmethyl)-3-ethenyl-4-carbonyl-2-azetidinone.

$IR_{max}^{CHCl_3}(cm^{-1})$: 1753, 1612, 1297, 1245, 1170, 1109, 1027, 828.

NMRδ(CDCl$_3$): 3.80(6H, s), 5.1-5.9(3H, m), 5.83(1H, s), 8.64(1H, s).

EXAMPLE 64

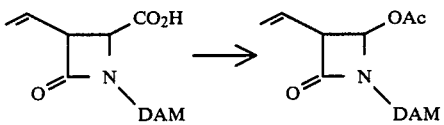

To a solution of 1-(di-p-anisylmethyl)-3-ethenyl-4-carboxyl-2-azetidinone (1.5 g) and potassium acetate (0.8 g) in dimethylformamide (7.5 ml) was added lead tetraacetate (2.17 g) in portions, followed by stirring for 1 hour at room temperature. The reaction mixture was diluted with water and extracted with ethyl acetate. The extract was washed with water, dried over anhydrous sodium sulfate and evaporated to give an oily residue which was purified by silica gel chromatography to give 1-(di-p-anisylmethyl)-3-ethenyl-4-acetoxy-2-azetidinone.

$IR_{max}^{CHCl_3}(cm^{-1})$: 1760, 1608, 1298, 1240, 1174, 1024, 974, 923.

NMRδ(CDCl$_3$): 1.90(3H, s), 3.79(6H, s), 5.74(1H, br, s), 5.91(1H, s).

EXAMPLE 65

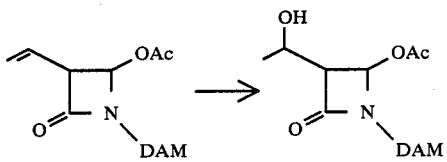

A solution of 1-(di-p-anisylmethyl)-3-ethenyl-4-acetoxy-2-azetidinone (3.80 g) and mercuric acetate (3.20 g) in tetrahydrofuran (10 ml) and water (4 ml) was stirred for 1 hour at room temperature. The reaction mixture was treated with 1N sodium hydroxide (9 ml) at 0° C. and then a solution of sodium borohydride (0.4 g) in 1N aqueous sodium hydroxide. After stirring at the same temperature for 5 to 6 minutes, the reaction mixture was neutralized with dilute hydrochloric acid, diluted with diethyl ether and filtered to remove any insoluble materials over Cerite. The filtrate was extracted with diethyl ether and the ether extract was washed successively with aqueous sodium bicarbonate and water, dried over anhydrous sodium sulfate and evaporated to give an oily residue which was then purified by silica gel chromatography to give 1-(di-p-anisyl-methyl)-3-(1-hydroxyethyl)-4-acetoxy-2-azetidinone.

$IR_{max}^{CHCl_3}(cm^{-1})$: 1752, 1608, 1357, 1302, 1242, 1174, 1028, 953.

NMRδ(CDCl$_3$): 1.25(3H, d, J=7), 1.90(3H, s), 3.07 (1H, br, d, J=6.5), 3.78(6H, s), 5.83(1H, s), 5.88(1H, br, s).

EXAMPLE 66

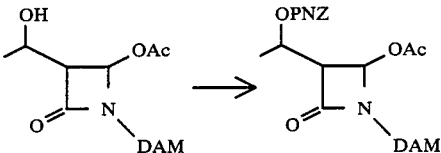

P-Nitrobenzyl chloroformate (3.52 g) in dichloromethane (9 ml) was added dropwise to a mixture of 1-(di-p-anisylmethyl)-3-(1-hdyroxyethyl)-4-acetoxy-2-azetidinone (5.3 g) and dimethylaminopyridine (1.98 g) in dichloromethane (18 ml). The reaction mixture was stirred overnight at room temperature, washed successively with water, dilute hydrochloric acid and again water, dried over anhydrous sodium sulfate and evaporated to give an oily residue which was then purified by silica gel chromatography to give 1-(di-p-anisylmethyl)-3-(1-p-nitrobenzyloxycarbonyloxyethyl)-4-acetoxy-2-azetidinone.

IR$_{max}^{film}$(cm$^{-1}$): 1770(shoulder), 1740, 1610, 1583, 1020, 850, 818, 735.

NMRδ(CDCl$_3$): 1.42(3H, d, J=6), 1.85(3H, s), 3.28 (1H, br, d, J=6), 5.22(2H, s), 5.87(1H, s), 6.11(1H, br, s).

EXAMPLE 67

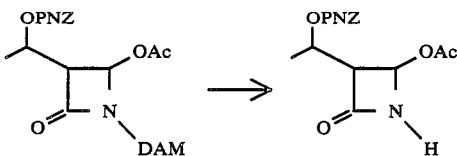

Ceric ammonium nitrate (12.1 g) was added to the solution of 1-(di-p-anisylmethyl)-3-(1-p-nitrobenzyloxycarbonyloxyethane-4-acetoxy-2-azetidinone (6.06 g) in 10% H$_2$O-acetonitrile (90 ml) in portions over 1 hour at room temperature, followed by stirring for 30 minutes. The reaction mixture was diluted with water and extracted with ethyl acetate. The extract was washed with water, dried over anhydrous sodium sulfate and evaporated to give an oily residue which was then purified by silica gel chromatography to give 3-(1-p-nitrobenzyloxycarbonyloxyethyl)-4-acetoxy-2-azetidinone.

IR$_{max}^{film}$(cm$^{-1}$): 1744, 1745, 1602, 1513, 1344, 1258, 1029, 843.

NMRδ(CDCl$_3$): 1.45(3H, d, J=6), 2.09(3H, s), 3.37 (1H, br, d, J=6, d), 5.87(1H, br, s), 6.96(1H, br, s).

EXAMPLE 68

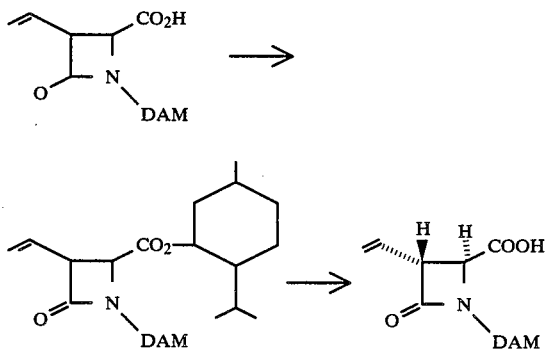

A solution of oxalyl chloride (4.25 g) in dichloromethane (5 ml) was added dropwise over 20 minutes to a mixture of 1-(di-p-anisylmethyl)-3-ethenyl-4-carboxyl-2-azetidinone (recemic form) (10.24 g) and a catalytic amount of dimethyl formamide in dichloromethane (45 ml) at room temperature. The resulting mixture was stirred for 1.5 hours at the same temperature and evaporated. The residue was dissolved in dichloromethane (30 ml) and cooled on ice-bath. The mixture was added dropwise to a mixture of 4-dimethylaminopyridine (3.58 g) and l-(−)-menthol (4.59 g) in dichloromethane (30 ml), followed by stirring for 2 hours. The reaction mixture was washed successively with 2N hydrochloric acid and aqueous sodium bicarbonate, dried over anhydrous sodium sulfate and evaporated to give an oily residue which was then crystallized from methanol to give l-menthyl ester derivative (the ratio of the two isomers was about 1:1) (m.p. 96°~97° C.).

The above crystals (10 g) were dissolved in methanol (400 ml) by heating and cooled at −5° C. Collection of the resulting crystals by filtration gave crystals of (3R, 4S)-1-(di-p-anisylmethyl)-3-ethenyl-4-l-(−)-menthyloxycarbonyl-2-azetidinone, which was further purified by recrystallization from methanol to give pure (3S, 4R)-l-(−)-menthyl ester derivative [m.p. 114°~115° C., specific rotation [α]$_D^{22}$ = +20.2°1 (C=0.26, CHCl$_3$)].

The separation of the two isomers of l-(−)-menthyl ester derivative obtained as described above was also accomplished using high performance liquid chromatography (Column Lichrosorb SI-60, solvent 1.5% isopropanol-hexane).

(3R, 4S)-1-(di-p-anisylmethyl)-3-ethenyl-4-carboxyl-2-azetidinone [specific rotation [α]$_D^{22}$ = +63.3° (C=0.12, CHCl$_3$)] was obtained from (3S, 4R)-1-(di-p-anisylmethyl-3-ethenyl-4-menthyloxycarbonyl-2-azetidinone in the similar procedure as described in Example 63.

EXAMPLE 69

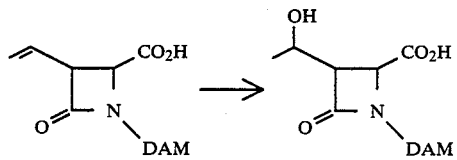

A mixture of 1-(di-p-anisylmethyl)-3-ethenyl 4-carboxyl-2-azetidinone (1.0 g) and mercuric acetate (0.9 g) in tetrahydrofuran (8.8 ml) and water (2 ml) was refluxed for 8 hours. After addition of 1N aqueous sodium hydroxide (7.2 ml) at 0° C., a solution of sodium borohydride (0.1 g) in 1N aqueous sodium hydroxide (1 ml) was added to the mixture, followed by stirring at the same temperature for 5 to 6 minutes. The reaction mixture was neutralized with 6N hydrochloric acid, diluted with diethyl ether, filtered over Cerite. The filtrate was extracted with diethyl ether and the extract was washed with saturated aqueous sodium chloride, dried over anhydrous sodium sulfate and evaporated to give an oily residue which was then purified by silica gel chromatography to give 1-(di-p-anisylmethyl)-3-(1-hydroxyethyl)-4-carboxyl-2-azetidinone (0.85 g).

IR$_{max}^{Nujol}$(cm$^{-1}$): 3250, 1750, 1723, 1515, 1305, 1250, 1177, 1030, 835.

NMRδ(CDCl$_3$): 1.22(3H, d, J=6 Hz), 3.18(1H, m), 3.72(6H, s), 4.10(1H, d, J=2 Hz), 5.75(1H, s).

Optically active (3R-, 4S)-1-(di-p-anisylmethyl)-3-((R)-1-hydroxyethyl)-4-carboxyl-2-azetidinone [specific rotation [α]$_D^{22}$ = +22.0°(C=0.14, CHCl$_3$)] was obtained from (3R-4S)-1-(di-p-anisylmethyl)-3-ethenyl-4-carboxyl-2-azetidinone by the similar procedure as described above.

EXAMPLE 70

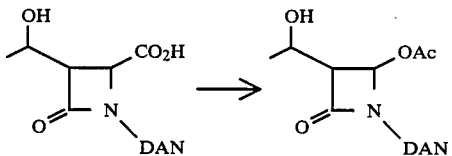

To a solution of 1-(di-p-anisylmethyl)-3-(1-hydroxyethyl)-4-carboxyl-2-azetidinone (4.0 g) (in dimethylformamide (40 ml) was added potassium acetate (1.0 g) Then, lead tetraacetate (5.3 g) was added in portions to the mixture at 40° C., followed by stirring for 1 hour. The reaction mixture was treated with ethylene glycol to destroy the residual lead tetraacetate, diluted with ethyl acetate and saturated aqueous sodium chloride and filtered over Celite to remove insoluble materials. The filtrate was extracted with ethyl acetate and the extract was washed with water, dried over anhydrous sodium sulfate and evaporated to give an oily residue which was then purified by silica gel chromatography to give 1-(di-p-anisylmethyl)-3-(1-hydroxyethyl)-4-acetoxy-2-azetidinone (3.03 g).

IR$_{max}^{CHCl_3}$(cm$^{-1}$): 1752, 1357, 1302, 1242, 1174, 1028, 953.

NMRδ(CDCl$_3$): 1.26(3H, d, J=6.5 Hz), 1.90(3H, s), 3.07(1H, br, d, J=6.5 Hz), 3.78(6H, s), 4.07(1H, m), 5.83(1H, br, s), 5.88(1H, br, s).

Optically active (3S, 4S)-1-(di-p-anisylmethyl)-3-((R)-1-hydroxyethyl)-4-acetoxy-2-azetidinone [specific rotation $[α]_D^{22}$=+26.0° (C=0.04, CHCl$_3$)] was obtained from (3S-4S)-1-(di-p-anisylmethyl)-3-((R)-1-hydroxyethyl)-4-carboxy-2-azetidinone by the procedure similar to that described above. (3S,4S)-3-((R)-1-p-nitrobenzyloxycarbonyloxyethyl)-4-acetoxy-2-azetidinone [specific rotation $[α]_D^{22}$=+36.6° C=0.09, CHCl$_3$)] was obtained from the above optical active acetoxy derivative by the procedures similar to those described in Examples 66 and 67 via (3R,4R)-1-(di-p-anisylmethyl)-3-((R)-1-p-nitrobenzyloxycarbonyloxyethyl)-4-acetoxy-2-azetidinone (specific rotation $[α]_D^{22}$=+40.5° (C=0.38, CHCl$_3$)).

EXAMPLE 71

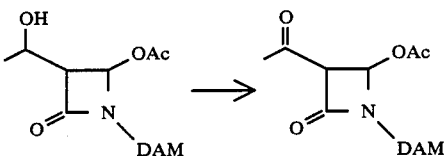

Jones' reagent (~1 ml) was added dropwise at room temperature to a solution of 1-(di-p-anisylmethyl)-3-(1-hydroxyethyl)-4-acetoxy-2-azetidinone (0.40 g) in acetone (5 ml), followed by stirring for 10 minutes. The reaction mixture was diluted with water and extracted with ethyl acetate. The extract was washed with water, dried over anhydrous sodium sulfate and evaporated to give an oily residue which was then purified by silica gel chromatography to give 1-(di-p-anisylmethyl)-3-acetyl-4-acetoxy-2-azetidinone.

IR$_{max}^{film}$(cm$^{-1}$): 1760, 1608, 1580, 1508, 1350, 1300, 1170, 1110, 1020, 815.

NMRδ(CDCl$_3$): 1.83(3H, s), 2.25(3H, s), 3.75(6H, s), 4.10(1H, d, J=1.5 Hz), 5.78(1H, s), 6.12(1H, d, J=1.5 Hz).

EXAMPLE 72

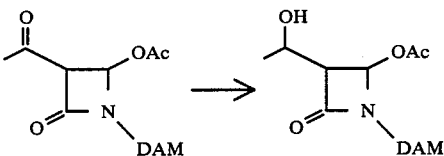

A mixture of sodium borohydride (38 mg) and 1-(di-p-anisylmethyl)-3-acetyl-4-acetoxy-2-azetidinone (397 mg) in isopropanol (6 ml) was stirred for 0.5 hour at room temperature. The reaction mixture was diluted with water and extracted with ethyl acetate. The extract was washed with water, dried over anhydrous sodium sulfate and evaporated to give 1-(di-p-anisylmethyl)-3-(1-hydroxyethyl)-4-acetoxy-2-azetidinone (the product was a mixture of two stereoisomers (about 1:1) of hydroxyethyl group).

NMRδ(CDCl$_3$); 3.10(1/2H, d, J=6.6 Hz), 3.16(1/2H, d, J=4.4 Hz).

Other peaks of NMR and IR spectra were similar to those of the compound obtained as described in Example 65.

EXAMPLE 73

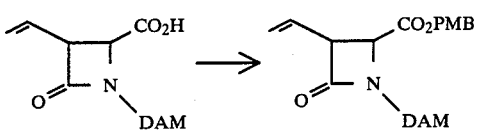

A mixture of 1-(di-p-anisylmethyl)-3-ethenyl-4-carboxyl-2-azetidinone (10 g), triethylamine (3.30 g) and p-methoxybenzyl chloride (5.19 g) in dimethylformamide (50 ml) was stirred at 70° C. for 20 hours. The reaction mixture was diluted with ethyl acetate, washed successively with water, 2N hydrochloric acid and aqueous sodium bicarbonate, dried over anhydrous sodium sulfate and evaporated to give an oily residue which was then purified by silica gel chromatography to give 1-(di-p-anisylmethyl)-3-ethenyl-4-p-methoxybenzyloxycarbonyl-2-azetidinone.

IR$_{max}^{neat}$(cm$^{-1}$): 1745, 1610, 1505, 1455, 1300, 1170, 1027, 822, 750.

NMRδ(CDCl$_3$): 3.72(3H, s), 3.75(6H, s), 4.83(2H, s), 5.1–6.0(3H, m), 5.78(1H, s).

EXAMPLE 74

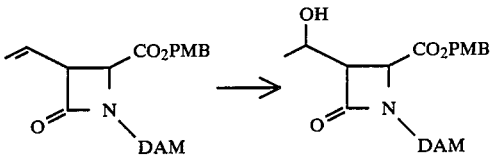

A mixture of 1-(di-p-anisylmethyl)-3-ethenyl-4-p-methoxybenzyloxycarbonyl-2-azetidinone (10 g) and mercuric acetate (6.6 g) in terahydrofuran (40 ml) and water (20 ml) was stirred at room temperature for 5 hours. The reaction mixture was treated with 1N aqueous sodium hydroxide (40 ml) and then sodium borohydride (0.78 g) in 1N aqueous sodium hydroxide (2 ml) at ~0° C. The mixture was acidified with 2N hydrochloric acid, filtered to remove any insoluble materials. The filtrate was extracted with diethyl ether. The extract was washed successively with water and aqueous sodium bicarbonate, dried over anhydrous sodium sulfate and evaporated to give an oily residue which was then purified by silica gel chromatography to give 1-(di-p-anisylmethyl)-3-(1-hydroxyethyl)-4-p-methoxybenzyloxycarbonyl-2-azetidinone.

IR$_{max}^{CHCl_3}$(cm$^{-1}$): 3400, 1742, 1510, 1303, 1242, 1175, 1032, 824.

NMRδ(CDCl$_3$): 1.17(3H, d, J=6 Hz), 3.13(1H, dd, J=2.2 and 3.4 Hz), 3.73(3H, s), 3.84(3H, s), 4.12(1H, d, J=2.2 Hz), 4.88(2H, d), 5.82(1H, s).

The above hydroxyethyl derivative was also prepared from 1-(di-p-anisylmethyl)-3-(1-hydroxyethyl)-4-carboxyl-2-azetidinone in a similar manner to that described in Example 12.

EXAMPLE 75

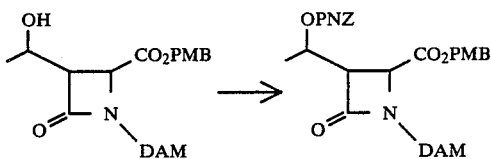

To a solution of 1-(di-p-anisylmethyl)-3-(1-hydroxyethyl)-4-p-methoxybenzyloxycarbonyl-2-azetidinone (4.5 g) in dichloromethane (25 ml) and 4-N,N-dimethylaminopyridine (1.31 g) was added dropwise p-nitrobenzylchloroformate (2.31 g) in dichloromethane (20 ml) with ice-cooling, followed by stirring for 2 hours. The reaction mixture was diluted with ethyl acetate, washed with 2N hydrochloric acid, dried over anhydrous sodium sulfate and evaporated to give an oily residue which was then purified by silica gel chromatography to give 1-(di-p-anisylmethyl)-3-(1-p-nitrobenzyloxycarbonyloxyethyl)-4-p-methoxybenzyloxycarbonyl-2-azetidinone.

IR$_{max}{}^{CHCl_3}$(cm$^{-1}$): 1760, 1515, 1347, 1250, 1176, 1030, 847.

NMRδ(CDCl$_3$): 1.38(3H, d, J=7 Hz), 3.32(1H, dd, J=3 and 7 Hz), 3.70(3H, s), 3.73(3H, s), 3.77(3H, s), 4.10 (1H, d, J=3 Hz), 4.87(2H, s), 5.18(2H, s), 5.78(1H, s).

EXAMPLE 76

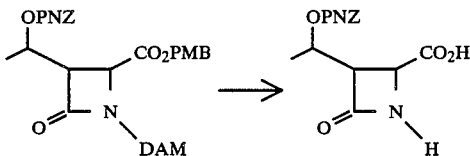

A mixture of 1-(di-p-anisylmethyl)-3-(1-p-nitrobenzyloxycarbonyloxyethyl)-4-p-methoxybenzyloxycarbonyl-2-azetidinone (0.64 g), anisol (0.43 g) and trifluoroacetic acid (1.2 ml) was stirred at 40° C. for 20 hours. The reaction mixture was concentrated, diluted with ethyl acetate, washed with water, dried over anhydrous sodium sulfate and evaporated to give an oily residue which was then purified by silica gel chromatography to give 3-(1-p-nitrobenzyloxycarbonyloxyethyl)-4-carboxyl-2-azetidinone.

IR$_{max}{}^{KBr}$(cm$^{-1}$): 3380, 1760, 1520, 1350, 1270, 1016, 850.

NMRδ((CD$_3$)$_2$SO): 1.33(3H, d, J=7 Hz), 3.40(1H, dd, J=2 and 5 Hz), 3.95(1H, d, J=2 Hz), 5.28(2H, s), 7.57(2H, d, J=9 Hz), 8.17(2H, d, J=9 Hz).

EXAMPLE 77

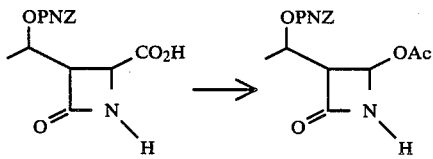

To a mixture of 3-(1-p-nitrobenzyloxycarbonyloxyethyl)-4-carboxyl-2-azetidinone (3.40 g) in dimethylformamide (20 ml) and potassium acetate (1.0 g) was added in portions lead tetraacetate (5.30 g) at 40° C. The reaction mixture was stirred for 1 hour, treated with ethylene glycol (~1 ml) for several minutes, diluted with ethyl acetate and saturated aqueous sodium chloride and filtered over Celite. The filtrate was extracted with ethyl acetate. The extract was washed with water, dried over anhydrous sodium sulfate and evaporated to give a residue which was then purified by silica gel chromatography to give 3-(1-p-nitrobenzyloxycarbonyloxyethyl)-4-acetoxy-2-azetidinone (2.46 g).

IR$_{max}{}^{CHCl_3}$(cm$^{-1}$): 1752, 1352, 1302, 1242, 1174, 1028, 953.

NMRδ(CDCl$_3$): 1.26(3H, d, J=6.5 Hz), 1.90(3H, s), 3.07 (1H, br, d, J=6.5 Hz), 3.78(6H, s), 4.07(1H, m), 5.83(1H, br, s), 5.88(1H, br, s).

EXAMPLE 78

A solution of sodium thioacetate, prepared by treating a solution of thioacetic acid (3.24 g) in dioxane (8 ml) and water (21.5 ml) with 1N aqueous sodium hydroxide, was added to a solution of 3-(1-p-nitrobenzyloxycarbonyloxyethyl)-4-acetoxy-2-azetidinone (15.0 g) in dioxane (56 ml) at 0° to 10° C. under nitrogen atmosphere. The reaction mixture was stirred at 0° C. for 15 minutes, diluted with ice-cooled dichloromethane, washed with water, dried over anhydrous sodium sulfate and evaporated to give an oily residue which was then purified by silica gel chromatography to give 3-(1-p-nitrobenzyloxycarbonyloxyethyl)-4-acetylthio-2-azetidinone.

IR$_{max}{}^{film}$(cm$^{-1}$): 1740, 1693, 1615, 1525, 1454, 1383, 1260, 1180, 1133, 1056, 1017, 960, 852.

NMRδ(CDCl$_3$): 1.42(3H, d, J=6 Hz), 2.02(3H, s), 3.37(1H, dd, J=2.2 and 6.5 Hz), 5.23(2H, s).

EXAMPLE 79

A mixture of 3-(1-p-nitrobenzyloxycarbonyloxyethyl)-4-acetylthio-2-azetidinone (9.37 g) and p-nitrobenzylglyoxylate (6.14 g) in dry benzene (300 ml) was refluxed for 4 hours and evaporated to dryness. To a solution of the resulting residue and 2,6-lutidine in dry tetrahydrofuran (353 ml) was added dropwise thionyl chloride (10.93 g) at −10° to 15° C. under nitrogen atmosphere. The reaction mixture was stirred for 20 minutes at the same temperature, filtered to remove any insoluble materials and the filtrate was evaporated to dryness. A mixture of the resulting residue, 2,6-lutidine (6.56 g) and triphenylphosphine (17.66 g) in dry dioxane (884 ml) was stirred at 55° to 65° C. for 20 hours under nitrogen atmosphere, and then evaporated at room temperature. The residue was diluted with dichloromethane, washed successively with 1N hydrochloric acid and water, dried over anhydrous sodium sulfate and evaporated to give an oily residue which was then purified by silica gel chromatography to give 3-(1-p-nitrobenzyloxycarbonyloxyethyl)-4-acetylthio-1-p-nitrobenzyloxycarbonyltriphenylphosphoranylidenemethyl-2-azetidinone.

IR$_{max}{}^{CHCl_3}$(cm$^{-1}$): 1750, 1692, 1622, 1605, 1518, 1436, 1377, 1353, 1258, 1202, 1168, 1102, 1079, 842.

EXAMPLE 80

To a mixture of 3-(1-p-nitrobenzyloxycarbonyloxyethyl)-1-(1-p-nitrobenzyloxycarbonyltriphenylphosphoranylidenemethyl)-4-acetylthio-2-azetidinone (2.4 g) and silver trifuluoroacetate (0.71 g) in dichloromethane (30 ml) was added methanol (30 ml) and 1,5-diazabicyclo-[5,4,0]undecene-5 (0.49 g) at room temperature. The reaction mixture was stirred for 6 hours, evaporated, treated with methanol with ice-cooling to give crystals. The resulting crystals were collected by filtration to give crystals of silver 3-(1-p-nitrobenzyloxycarbonyloxyethyl)-1-(1-p-nitrobenzyloxycarbonyltriphenylphosphoranylidenemethyl-2-azetidinone-4-thiolate.

$IR_{max}^{KBr}(cm^{-1})$: 1746, 1620(sh), 1603, 1518, 1437, 1333, 1254, 1102, 845.

Further, silver 3-(1-p-nitrobenzyloxycarbonyloxyethyl)-1-(1-p-nitrobenzyloxycarbonyltriphenylphosphoranylidenemethyl)-2-azetidinone-4-thiolate was prepared by the procedure similar to that described above from the corresponding acetyl derivative. Also, this silver salt could be prepared by the method as described in Japanese Patent Application (OPI) No. 25110/81.

EXAMPLE 81

To a solution of silver 3-(1-p-nitrobenzyloxycarbonyloxyethyl)-1-p-nitrobenzyloxycarbonyltriphenylphosphoranylidenemethyl-2-azetidinone-4-thiolate (890 mg) in dry dichloromethane (24 ml) was added 4-dimethylaminopyridine (244 mg) and then a solution of β-4-(1-p-nitrobenzyloxycarbonyl)piperidineylacrylyl chloride (0.529 g) in dry dichloromethane (4 ml) at room temperature under nitrogen atmosphere. After stirring for 30 minutes at the same temperature, the reaction mixture was filtered over Celite. The filtrate was washed successively with 1N hydrochloric acid, water, aqueous sodium carbonate and again water, dried over anhydrous sodium sulfate and evaporated to give an oily residue which was purified by silica gel chromatography to give 3-(1-p-nitrobenzyloxycarbonyloxyethyl)-4-(1-(4-1-p-nitrobenzyloxycarbonyl)piperidinyl)ethenyl)carbonylthio-1-(p-nitrobenzylcarbonyltriphenylphosphoranylidenemethyl)-2-azetidinone.

$IR_{max}^{CHCl_3}(cm^{-1})$: 1746, 1680, 1616, 1600, 1512, 1430, 1320, 1245, 1100, 1005, 838.

β-(4-(1-p-nitrobenzyloxycarbonyl)piperidinylacrylyl chloride used above was obtained from the corresponding carboxylic acid derivative by the following procedure:

To a solution of β-(4-(1-p-nitrobenzyloxycarbonyl)piperidinylacrylic acid (501 mg) and a catalytic amount of dimethylformamide in dry benzene (5 ml) was added dropsise thionyl chloride (1.07 g). After refluxing for 5 hours, the reaction mixture was evaporated to dryness. The residue was dissolved in benzene and the benzene and excess of thionyl chloride were evaporated. The resulting acid chloride was used in the next reaction without further purification.

The following compounds were also obtained from the corresponding silver salts and active derivatives of the corresponding carboxylic acid by the procedure similar to that described in Example 81.

The acid chloride could be obtained from the corresponding carboxylic acid and thionyl chloride or oxalyl chloride by the procedure similar to that described in Example 81.

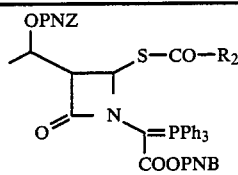

| Example No. | R₂ | Spectral Data |
|---|---|---|
| 82 | —CH₂S—⟨N—PNZ⟩ | $IR_{max}^{CHCl_3}$ (cm⁻¹): 1755, 1704(sh), 1690, 1630(sh), 1605, 1520, 1440, 1348, 1250, 1108, 1010, 844 |
| 83 | —CH₂CH₂—⟨N—PNZ⟩ | $IR_{max}^{CHCl_3}$ (cm⁻¹): 1753, 1690, 1620, 1608, 1520, 1437, 1346, 1260, 1107, 1080, 850 |
| 84 | —CH₂—⟨NPNZ⟩ | $IR_{max}^{CHCl_3}$ (cm⁻¹): 1750, 1700(sh), 1690, 1622(sh), 1605, 1520, 1435, 1343, 1255, 1103, 845 |
| 85 | H>=⟨N—PNZ⟩ | $IR_{max}^{CHCl_3}$ (cm⁻¹): 1760, 1708, 1625(sh), 1612, 1525, 1443, 1350, 1320, 1260, 1212, 1110, 1050, 930, 850 |
| 86 | H>=⟨NPNZ⟩ | $IR_{max}^{CHCl_3}$ (cm⁻¹): 1754, 1700, 1625(sh), 1608, 1520, 1438, 1400, 1349, 1260, 1107, 845 |
| 87 | —CH=CH—⟨NPNZ⟩ | $IR_{max}^{CHCl_3}$ (cm⁻¹): 1752, 1700, 1604, 1522, 1437, 1348, 1260, 1108, 850 |

-continued

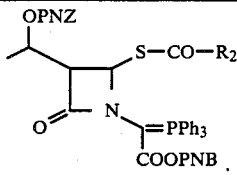

| Example No. | $R_2$ | Spectral Data |
|---|---|---|
| 88 | H₃C\C=CH— (cyclohexyl)NPNZ | $IR_{max}^{CHCl_3}$ (cm$^{-1}$): 1752, 1690, 1522, 1437, 1350, 1260, 1106 |
| 89 | —(cyclohexyl)—NHPNZ | $IR_{max}^{CHCl_3}$ (cm$^{-1}$): 3440, 1750, 1720(sh), 1607, 1515, 1440, 1345, 1255, 1205(sh), 1105, 1080, 1053, 1014, 943, 847 |
| 90 | —(cyclohexyl)—CH₂NHPNZ | $IR_{max}^{CHCl_3}$ (cm$^{-1}$): 1755, 1735(sh), 1610, 1520, 1515(sh), 1442, 1350, 1260, 1208, 1108, 848 |
| 91 | —(cyclohexyl)—CH₂CH₂NHPNZ | $IR_{max}^{CHCl_3}$ (cm$^{-1}$): 1750, 1720(sh), 1695(sh), 1602, 1514, 1345, 1252, 1210, 1102, 842 |
| 92 | —(cyclohexyl)—CH₂OPNZ | $IR_{max}^{CHCl_3}$ (cm$^{-1}$): 1752, 1690, 1610, 1524, 1352, 1260, 1208, 1108, 848 |
| 93 | —(cyclohexyl) | $IR_{max}^{CHCl_3}$ (cm$^{-1}$): 1752, 1685, 1619, 1606, 1517, 1435, 1343, 1258, 1205, 1103 |
| 94 | —CH=CH—CH₂—CH₂NHPNZ | $IR_{max}^{CHCl_3}$ (cm$^{-1}$): 1748, 1663, 1620, 1605, 1513, 1434, 1344, 1250, 1102, 840 |

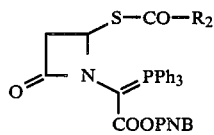

| Example No. | $R_2$ | Spectral Data |
|---|---|---|
| 95 | —(cyclohexyl)—NHPNZ | $IR_{max}^{film}$ (cm$^{-1}$): 1754(sh), 1713, 1600, 1510, 1435, 1385, 1342, 1248, 1214, 1102, 1080, 1034, 1007, 940, 840 |
| 96 | —(cyclohexyl)—CH₂NHPNZ | $IR_{max}^{Nujol}$ (cm$^{-1}$): 1750, 1717(sh), 1620, 1605, 1520, 1437, 1390, 1343, 1243, 1128, 1103, 1078, 1038, 1008, 935, 842 |
| 97 | —CH₂—(cyclohexyl)NPNZ | $IR_{max}^{film}$ (cm$^{-1}$): 1750, 1700(sh), 1690, 1620, 1603, 1516, 1435, 1342, 1260, 1242, 1104, 1078, 1010, 963, 842 |

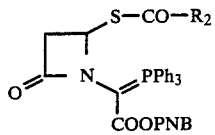

| Example No. | R$_2$ | Spectral Data |
|---|---|---|
| 98 | -CH= (piperidine-NPNZ) | IR$_{max}^{film}$ (cm$^{-1}$): 1752, 1703, 1650(sh), 1624, 1607, 1516, 1484, 1438, 1390, 1344, 1237, 1110, 1082, 1043, 1017, 1000, 984, 966, 850 |
| 99 | -CH=CH-C(CH$_3$)$_2$CH$_2$-NHPNZ | IR$_{max}^{film}$ (cm$^{-1}$): 1750, 1720, 1655, 1620, 1600, 1514, 1478, 1434, 1381, 1340, 1240, 1100, 1076, 1025, 990, 835 |
| 100 | (pyridyl) | IR$_{max}^{film}$ (cm$^{-1}$): 1763, 1670, 1625, 1606, 1520, 1440, 1346, 1263, 1223, 1200, 1110, 1090, 924 |
| 101 | (pyridyl) | IR$_{max}^{film}$ (cm$^{-1}$): 1747, 1660, 1615, 1513, 1430, 1340, 1260, 1100, 1076, 900 |

EXAMPLE 102

To a solution of 3-(1-p-nitrobenzyloxycarbonyloxyethyl)-4-acetoxy-2-azetidinone (2.46 g) in dioxane (10 ml) was added dropwise a solution of the sodium salt, which was prepared by treatment of 1-p-nitrobenzyloxycarbonylpiperidinyl-4-thioacetic acid (2.26 g) in dioxane (13 ml) with 1N-aqueous sodium hydroxide (7 ml) at 0° C. under nitrogen atmosphere. After stirring for 10 minutes, the reaction mixture was diluted with dichloromethane. The organic layer was washed with water, dried over anhydrous sodium sulfate and evaporated to give an oily residue which was then purified by silica gel chromatography to give 3-(1-p-nitrobenzyloxycarbonyloxyethyl)-4-(4-p-nitrobenzyloxycarbonylpiperidinylmethyl)carbonylthio-2-azetidinone.

IR$_{max}^{CHCl3}$(cm$^{-1}$): 1775, 1750(sh), 1685, 1608, 1520, 1435, 1345, 1260, 1127, 1012, 848.

NMRδ(CDCl$_3$): 1.43(3H, d, J=6 Hz), 3.39(1H, dd, J=2 and 6.5 Hz), 5.21(2H, s), 5.27(2H, s).

4-(1-p-Nitrobenzyloxycarbonyl)piperidinyl thioacetic acid was prepared from the corresponding carboxylic acid derivative by the following procedure:

To a solution of 4-(1-p-nitrobenzyloxycarbonyl)piperidinylacetic acid (2.25 g) and triethylamine (1.07 g) in dry dichloromethane (70 ml) was added ethyl chloroformate (0.74 g) at a temperature up to 0° C. The resulting mixture was cooled at −15° C. Hydrogen sulfide gas was bubbled into the mixture for 45 minutes and then nitrogen gas for 1 hour at −5° to −15° C. The reaction mixture was acidified with 2N sulfuric acid (4 ml), followed by stirring for 15 minutes. The organic layer was washed with saturated aqueous sodium chloride, dried over anhydrous sodium sulfate and evaporated to give 4-(1-p-nitrobenzyloxycarbonyl)-piperidinylthioacetic acid, which was used in the next process without further purification.

IR$_{max}^{film}$(cm$^{-1}$): 2550, 1688, 1602, 1510, 1340, 1270, 1232, 1200, 1122, 840.

Thiocarboxylic acids used in the following Examples were prepared by the procedure similar to that described above from the corresponding carboxylic acids via the acid chlorides or the mixed anhydrides.

EXAMPLE 103

3-(1-p-nitrobenzyloxycarbonyloxyethyl)-4-(1-p-nitrobenzyloxycarbonyl)piperidinylidenemethyl)carbonylthio-2-azetidinone was prepared by using 1-p-nitrobenzyloxycarbonylpiperidinylidenemethylthiocarboxylic acid (IR$_{max}^{film}$cm$^{-1}$: 2550, 1686, 1342, 1222, 1105) by the procedure similar to that described in Example 102. The product thus obtained had the following spectral data.

IR$_{max}^{CHCl3}$(cm$^{-1}$): 1775, 1750(sh), 1685, 1610, 1520, 1430, 1340, 1255, 1200, 1105, 1035, 975.

NMRδ(CDCl$_3$): 1.44(3H, d, J=6 Hz), 5.26(4H, s), 5.98(1H, br, s), 7.53(4H, d, J=9 Hz), 8.19(4H, d, J=9 Hz).

3-(1-p-Nitrobenzyloxycarbonyloxyethyl)-4-(4-p-nitrobenzyloxycarbonylaminomethylphenyl)-carbonylthio-2-azetidinone [IR$_{max}^{film}$cm$^{-1}$: 1760, 1720, 1664, 1606, 1520, 1345, 1260, 1215, 1173, 1045, 1014, NMRδ(CDCl$_3$): 1.49(3H, d, J=6.2 Hz), 3.47(1H, dd, J=2.2 and 6.4 Hz), 5.24 (4H, br, s), 5.44(1H, d, J=2.2 Hz)] and 3-(1-p-nitrobenzyloxycarbonyloxyethyl)-4-(4-p-nitrobenzyloxycarbonylamino-4-methylvaleryl)thio-2-azetizinone [IR$_{max}^{CHCl3}$cm$^{-1}$: 1773, 1728, 1690, 1520, 1345, 1256, 1078, NMRδ(CDCl$_3$): 1.31(6H, s), 1.43(3H, d, J=6 Hz), 3.34(1H, dd, J=2.5 and 6 Hz), 5.12(2H, s), 5.23(2H, s), 7.45(2H, d, J=8.5 Hz), 7.49(2H, d, J=8.5 Hz), 8.13(1H, d, J=8.5 Hz), 8.16(2H, d, J=8.5 Hz)] were also prepared from the corresponding thiocarboxylic acid by the procedure similar to that described above.

The following compounds were also prepared from 4-acetoxy-2-azetidinone and the corresponding thiocarboxylic acid sodium salt by the procedure similar to that described in example 102.

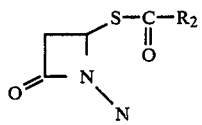

| Example No. | R₂ | Spectral Data |
|---|---|---|
| 104 | —CH₂CH₂C(CH₃)₂NHPNZ | IR$_{max}^{CHCl_3}$(cm⁻¹): 1773, 1726, 1688, 1605, 1520, 1344, 1080, 975<br>NMRδ(CDCl₃): 1.32(6H,s), 2.90(1H,ddd,J=1, 3 and 15.5Hz), 3.40(1H,ddd,J=1.5, 5 and 15.5Hz), 5.14(2H,s) |
| 105 | —CH₂C(CH₃)₂CH₂NHPNZ | IR$_{max}^{film}$(cm⁻¹): 1750, 1680, 1603, 1337, 1235, 1140, 1104, 1000, 950, 900, 855<br>NMRδ(CDCl₃): 1.03(6H,s), 2.49(2H,s), 2.88 (1H,ddd,J=1.5, 2.5 and 15Hz), 3.12(2H, d,J=6.5Hz), 3.39(1H,ddd,J=1.5, 5 and 15Hz), 5.16(2H,s) |
| 106 | —CH₂C(CH₃)₂NHPNZ | IR$_{max}^{film}$(cm⁻¹): 1760, 1725, 1690, 1608, 1520, 1345, 1240, 1086, 1002, 950, 905, 850<br>NMRδ(CDCl₃): 1.42(6H,s), 2.91(1H,ddd,J=1.5, 2.5 and 15.5Hz), 3.02(2H,s), 3.39(1H, ddd,J=1.5, 5.5 and 15.5Hz), 5.13(2H,s) |
| 107 | —CH₂CH₂C(CH₃)₂CH₂NHPNZ | IR$_{max}^{film}$(cm⁻¹): 1755, 1720, 1608, 1520, 1346, 1240, 1140, 1066, 1010, 982, 905, 860<br>NMRδ(CDCl₃): 0.90(6H,s), 3.02(2H,d,J=6.4Hz), 3.40(1H,ddd,J=2, 5 and 15.5Hz), 5.18 (2H,s) |
| 108 | —CH₂CH₂CH₂C(CH₃)₂NHPNZ | IR$_{max}^{film}$(cm⁻¹): 1760, 1710, 1608, 1520, 1348, 1260, 1216, 1160, 1090, 982, 856<br>NMRδ(CDCl₃): 1.28(6H,s), 2.96(1H,ddd,J=1.5, 3 and 15.5Hz), 3.41(1H,ddd,J=1.5, 5 and 15.5Hz), 5.12(2H,s) |
| 109 | —⟨cyclohexyl⟩—NPNZ | IR$_{max}^{film}$(cm⁻¹): 1760, 1700(sh), 1680, 1602, 1512, 1342, 1275, 1222, 1120, 1006,<br>NMRδ(CDCl₃): 3.40(1H,ddd,J=2, 5 and 15Hz), 5.20(2H,s), 6.80(1H,br,s), 7.49(2H,d, J=9Hz), 8.16(2H,d,J=9Hz) |
| 110 | —CH₂CH₂COO—ONB | IR$_{max}^{Nujol}$(cm⁻¹): 1760, 1720, 1692, 1608, 1515, 1330, 1185, 1080, 976, 965, 943, 855<br>NMRδ(CDCl₃): 3.40(1H,ddd,J=2, 5 and 15.5Hz), 5.22(1H,dd,J=2 and 5Hz), 5.33(2H,s) |
| 111 | —⟨phenyl⟩—CH₂CH₂NHPNZ | IR$_{max}^{Nujol}$(cm⁻¹): 1753, 1685, 1600, 1508, 1342, 1245, 1210, 1172, 1140, 1002, 910, 890, 842<br>NMRδ(CDCl₃): 5.18(2H,s), 5.42(1H,dd,J=2.5 and 5Hz), 6.68(1H,br,s) |
| 112 | —⟨phenyl⟩—NHPNZ | IR$_{max}^{Nujol}$(cm⁻¹): 1750(sh), 1730, 1652, 1597, 1540, 1520, 1342, 1220, 1172, 1072, 900, 840<br>NMRδ(DMSO—d₆): 5.32(2H,s), 8.20(2H,d,J=9Hz), 8.68(1H,br,s) |
| 113 | —⟨phenyl⟩—CH₂NHPNZ | IR$_{max}^{Nujol}$(cm⁻¹): 1783, 1675, 1660, 1600, 1513, 1340, 1260, 1140, 1048, 1000<br>NMRδ(CDCl₃—DMSO—d₆ 1:2): 3.03(1H,ddd,J=1.5, 2.5 and 15.5Hz), 3.55(1H,ddd,J=1.5, 5 and 15.5Hz), 4.31(2H,d,J=6.5Hz), 5.20 (2H,s), 5.36(1H,dd,J=2.5 and 5Hz) |
| 114 | —⟨phenyl⟩(OPNZ)(OPNZ) | IR$_{max}^{CHCl_3}$(cm⁻¹): 1770, 1655, 1602, 1520, 1370, 1345, 1248, 1205(sh), 1155, 1020, 965<br>NMRδ(CDCl₃): 3.05(1H,ddd,J=1, 2.5 and 16Hz), 3.51(1H,ddd,J=2.5 and 16Hz), 5.68(4H,s) |

-continued

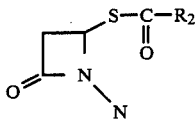

| Example No. | R$_2$ | Spectral Data |
|---|---|---|
| 115 | —⟨C$_6$H$_4$⟩—COOPMB | IR$_{max}^{Nujol}$(cm$^{-1}$): 1743, 1716, 1660, 1615, 1518, 1405, 1376, 1278, 1250, 1208, 1100, 1030, 925, 821<br>NMRδ(CDCl$_3$): 3.13(1H,ddd,J=1, 2.5 and 15Hz), 3.48(1H,ddd,J=2, 4.5 and 15Hz), 5.30 (2H,s), 5.35(1H,dd,J=2.5 and 4.5Hz) |

EXAMPLE 116

To 1-p-nitrobenzyloxycarbonyl-4-mercaptomethyl-piperidine (3.67 g) in ethanol (35 ml) was added dropwise potassium hydroxide (0.63 g) at 0° to 5° C. under argon atmosphere. After stirring for 30 minutes at the same temperature, carbon disulfide (1.80 g) was added to the reaction mixture at room temperature. After stirring for 3 hours, the resulting mixture was cooled on an ice bath and diluted with water (13 ml). To a solution of 3-(1-p-nitrobenzyloxycarbonyloxyethyl)-4-acetoxy-2-azetidinone (4.17 g) in dioxane (14 ml) was added dropwise the above mixture at 15° C. under argon atmosphere. After stirring for 30 minutes, the reaction mixture was diluted with dichloromethane, and the organic layer was washed with water, dried over anhydrous sodium sulfate and evaporated to give an oily residue which was then purified by silica gel chromatography to give 3-(1-p-nitrobenzyloxycarbonyloxyethyl)-4-[4-(1-p-nitrobenzyloxycarbonylpiperidinyl)methylthio]-thiocarbonylthio-2-azetidinone.

IR$_{max}^{film}$(cm$^{-1}$): 1770(sh), 1750, 1680, 1600, 1510, 1435, 1340, 1245, 1108, 1055, 845.

NMRδ(CDCl$_3$): 1.50(3H, d, J=6 Hz), 5.20(2H, s), 5.23(2H, s), 5.61(1H, d, J=2.5 Hz).

(3S,4R)-3-((R)-1-p-Nitrobenzyloxycarbonyloxyethyl)-4-(4-(1-p-nitrobenzyloxycarbonylpiperidinylmethylthio)thiocarbonylthio-2-azetidinone [specific rotation [α]$_D^{20}$=+101.2° (C=0.86, CHCl$_3$)] was prepared from (3R,4R)-3-((R)-1-p-nitrobenzyloxycarbonyloxyethyl)-4-acetoxy-2-azetidinone by the procedure similar to that described above. (IR and NMR spectra were identical with those of the above compound.)

EXAMPLE 117

To 3-(1-p-Nitrobenzyloxycarbonyloxyethyl-4-acetoxy-2-azetidinone (1.55 g) in dioxane (15 ml) was added dropwise a solution of potassium 4-(1-p-nitrobenzyloxycarbonyl)piperidinyltrithiocarbonate (1.90 g) in dioxane (15 ml) and water (15 ml) at room temperature under argon atmosphere. After stirring for 1 hour, the reaction mixture was diluted with dichloromethane. The organic layer was washed with water, dried over anhydrous sodium sulfate and evaporated to give an oily residue which was then purified by silica gel chromatography to give 3-(1-p-nitrobenzyloxycarbonyloxyethyl)-4-[4-(1-p-nitrobenzyloxypiperidinyl)thio]thiocarbonylthio-2-azetidinone.

IR$_{max}^{CHCl3}$(cm$^{-1}$): 1772, 1685, 1515, 1340, 1250.

NMRδ(CDCl$_3$): 1.45(3H, d, J=6 Hz), 3.43(1H, dd, J=2.5, 6 Hz), 5.23(2H, s), 5.62(1H, d, J=2.5 Hz), 7.50(2H, d, J=9 Hz), 8.17(2H, d, J=9 Hz).

The starting potassium trithiocarbonate was prepared by the following procedure:

To a solution of 1-(p-nitrobenzyloxycarbonyl)-4-mercaptopiperidine (1.54 g) in dry ethanol (25 ml) was added potassium hydroxide (292 mg) in dry ethanol (3 ml) at 0° C. under argon atmosphere. After stirring for 30 minutes at the same temperature, carbon disulfide (792 mg) was added to the reaction mixture. The mixture was stirred for 3 hours at room temperature. The resulting crystals were collected by filtration, washed with ethanol and dried to give potassium 4-(1-p-nitrobenzyloxycarbonylpiperidinyltrithiocarbonate.

(3S,4R)-3-((R)-1-p-Nitrobenzyloxycarbonyloxyethyl)-4-[4-(1-p-nitrobenzyloxypiperidinyl)thio]thiocarbonylthio-2-azetidinone was prepared from (3R,4R)-3-((R)-1-p-nitrobenzyloxycarbonyloxyethyl)-4-acetoxy-2-azetidinone by the procedure similar to that described above.

Specific rotation: [α]$_D^{22}$=+113.5° (C=0.75, CHCl$_3$)
(IR and NMR spectra were identical with those of the above compound.)

The following compounds were prepared from 3-(1-p-nitrobenzyloxycarbonylethyl)-4-acetoxy-2-azetidinone and the corresponding potassium trithiocarbonate obained from the mercaptane derivatives by the procedure similar to that described in Example 116 or 117.

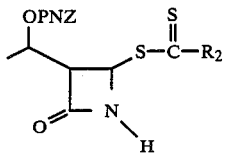

| Example No. | R$_2$ | Spectral Data | |
|---|---|---|---|
| 118 | SCH$_2$CH$_2$—(piperidine)N—PNZ | IR$_{max}^{CDCl_3}$(cm$^{-1}$): | 1780, 1750, 1695, 1525, 1441, 1351, 1260 |
| | | NMRδ(CDCl$_3$): | 1.45(3H,d,J=6Hz), 3.38(1H, dd,J=3 & 6Hz), 5.20(4H,s), 5.60(1H,d,J=3Hz), 7.46(4H, d,J=9Hz), 8.16(4H,d,J=9Hz) |
| 119 | SCH$_2$CH=(tetrahydropyridine)N—PNZ | IR$_{max}^{CDCl_3}$(cm$^{-1}$): | 1775, 1747, 1690, 1520, 1433, 1342, 1252, 1210, 1110, 1063 |
| | | NMRδ(CDCl$_3$): | 1.46(3H,d,J=7Hz), 4.00(2H,d J=8Hz), 5.22(4H,s), 5.66(1H, d,J=3Hz), 7.49(4H,d,J=8.5Hz), 8.17(4H,d,J=8.5Hz) |
| 120 | SCH$_2$—(tetrahydropyridine)N—PNZ | IR$_{max}^{CDCl_3}$(cm$^{-1}$): | 1775, 1745(sh), 1695, 1520, 1445, 1252, 1205 |
| | | NMRδ(CDCl$_3$): | 1.45(3H,d,J=6Hz), 3.40(1H, dd,J=3 & 6Hz), 3.58(2H,t, J=6Hz), 4.02(2H,s), 5.22(4H, s), 5.58(1H,d,J=3Hz), 7.46 (4H,d,J=8.5Hz), 8.13(4H,d, J=8.5Hz) |
| 121 | S—(cyclohexyl) | IR$_{max}^{CDCl_3}$(cm$^{-1}$): | 1775, 1745(sh), 1522, 1345, 1258, 1210, 1070 |
| | | NMRδ(CDCl$_3$): | 3.37(1H,dd,J=3 & 6Hz), 5.21 (2H,s), 5.58(1H,d,J=3Hz), 7.47(2H,d,J=9Hz), 8.15(2H, d,J=9Hz) |
| 122 | SCH$_2$C(CH$_3$)$_2$CH$_2$NHPNZ | IR$_{max}^{CDCl_3}$(cm$^{-1}$): | 1780, 1735, 1610, 1522, 1350, 1258, 1073 |
| | | NMRδ(CDCl$_3$): | 1.03(6H,s), 1.45(3H,d,J= 6Hz), 3.12(2H,d,J=6.5Hz), 3.42(2H,s), 5.18(2H,s), 5.23(2H,s), 5.61(1H,d,J= 2.2Hz) |

EXAMPLE 123

4-[4-(1-p-Nitrobenzyloxycarbonylpiperidinyl)thio]-thiocarbonylthio-2-azetizinone was prepared from 4-acetoxy-2-azetizinone and potassium 4-(1-p-nitrobenzyloxycarbonyl)piperidinyltrithiocarbonate by the procedure similar to that described in Example 117.

IR$_{max}^{CHCl_3}$(cm$^{-1}$): 3420, 1775, 1692, 1605, 1522, 1438, 1345, 1265, 1242, 1062, 1000, 817.

NMRδ(CDCl$_3$): 5.20(2H, s), 5.53(1H, dd, J=2.5 and 5 Hz), 7.45(2H, d, J=9 Hz), 8.17(2H, d, J=9 Hz).

The following compounds were also prepared from 4-acetoxy-2-azetidinone and the corresponding potassium trithiocarbonate obtained from the mercaptane derivatives, by the procedure similar to that described in Example 116 to 123.

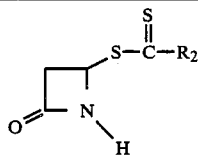

| Example No. | R$_2$ | Spectral Data | |
|---|---|---|---|
| 124 | —S(CH$_2$)$_3$C(CH$_3$)$_2$NHPNZ | IR$_{max}^{film}$(cm$^{-1}$): | 1767, 1620, 1605, 1517, 1450, 1343, 1252, 1212, 1150, 1080, 1065, 1010, 902, 820 |
| | | NMRδ(CDCl$_3$): | 1.28(6H,s), 3.01(1H,ddd,J=1, 2.5 and 15.5Hz), 5.15(2H,s), 5.58(1H,dd, J=2.5 and 5Hz) |
| 125 | —S(CH$_2$)$_2$C(CH$_3$)$_2$CH$_2$NHPNZ | IR$_{max}^{film}$(cm$^{-1}$): | 1760, 1715, 1600, 1512, 1470, 1398, 1360, 1338, 1232, 1132, 1060, |

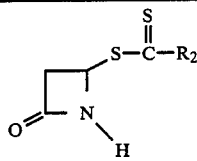

| Example No. | R$_2$ | Spectral Data |
|---|---|---|
| 126 | —S(CH$_2$)$_2$C(CH$_3$)$_2$NHPNZ | 1040, 1004, 970, 818<br>NMRδ(CDCl$_3$): 0.97(6H,s), 3.06(2H,d,J=7Hz), 5.33(2H,s), 5.53(1H,d,J=2.5 and 5Hz) |
| 127 | —SCH$_2$C(CH$_3$)$_2$NHPNZ | IR$_{max}^{film}$(cm$^{-1}$): 1775, 1730, 1602, 1520, 1447, 1384, 1341, 1252, 1152, 1083, 973, 820<br>NMRδ(CDCl$_3$): 1.39(6H,s), 3.04(1H, ddd, J=1, 2.5 and 15.5Hz), 3.46(1H, ddd, J=2.5 and 15.5Hz), 5.16(2H,s), 5.55(1H,dd,J=2.5 and 5Hz) |
| 128 | —SCH$_2$C(CH$_3$)$_2$CH$_2$NHPNZ | IR$_{max}^{film}$(cm$^{-1}$): 1760, 1720, 1605, 1519, 1450, 1403, 1380, 1344, 1262, 1233, 1080, 1067, 1065, 816<br>NMRδ(CDCl$_3$): 1.43(6H,s), 3.05(1H,ddd, J=1, 2.5 and 15Hz), 3.46(1H,ddd, J=2, 5.5 and 15Hz), 3.91(2H,s), 5.57(1H,dd,J=2.5 and 5.5Hz) |
| 129 | —SCH$_2$C(CH$_3$)$_2$CH$_2$CH$_2$NHPNZ | IR$_{max}^{film}$(cm$^{-1}$): 1753, 1720, 1607, 1520, 1465, 1405, 1345, 1237, 1142, 1087, 1066, 1039, 1010, 976, 818<br>NMRδ(CDCl$_3$): 1.03(6H,s), 3.12(2H,d,J=6Hz), 3.44(2H,s), 5.21(2H,s), 5.56(1H,dd,J=2.5 and 5Hz) |
| 130 | —SCH$_2$—[piperidinyl]N—PNZ | IR$_{max}^{film}$(cm$^{-1}$): 1760, 1705, 1602, 1513, 1461, 1400, 1338, 1240, 1137, 1060, 1040(sh), 1006, 971, 813<br>NMRδ(CDCl$_3$): 1.07(6H,s), 3.42(2H,s), 5.17(2H,s), 5.54(1H,dd,J=2.5 and 5Hz)<br>IR$_{max}^{film}$(cm$^{-1}$): 1772, 1680, 1604, 1522, 1350, 1317, 1238, 1202, 1178, 1125, 1040, 970, 882<br>NMRδ(CDCl$_3$): 3.34(2H,d,J=6Hz), 5.21(2H,s), 5.57(1H,dd,J=2.5 and 5Hz) |

EXAMPLE 131

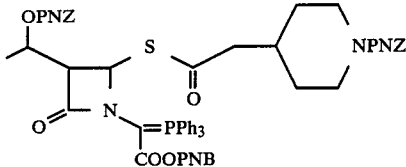

A mixture of 3-(1-p-nitrobenzyloxycarbonyloxyethyl)-4-(4-(1-p-nitrobenzyloxycarbonyl)piperidinyl)methylcarbonylthio-2-azetidinone (3.64 g) and p-nitrobenzyl glyoxylate (1.57 g) in dry benzene (100 ml) was refluxed for 10 hours and evaporated to dryness. The residue was dissolved in dry tetrahydrofuran (69 ml), and thionyl chloride (2.06 g) was added dropwise to the solution at −10° to −15° C. in the presence of 2,6-lutidine (2.04 g) under nitrogen atmosphere, followed by stirring for 20 minutes. The reaction mixture was evaporated to dryness. To the residue in dry dioxane (170 ml), 2,6-lutidine (1.25 g) and triphenylphosphine (3.33 g) were added and the mixture was stirred at 50° to 60° C. for 30 hours under nitrogen atmosphere. The reaction mixture was evaporated to dryness. The residue was diluted with dichloromethane and the solution was washed successively with 1N hydrochloric acid and water, dried over anhydrous sodium sulfate and evaporated to give an oily residue which was then purified by silica gel chromatography to give 3-(1-p-nitrobenzyloxycarbonyloxyethyl)-4-(4-(1-p-nitrobenzyloxycarbonyl)-piperidinyl)methylcarbonylthio-1-p-nitrobenzyloxycarbonyltriphenylphosphoranylidenemethyl-2-azetidinone.

IR$_{max}^{CHCl3}$(cm$^{-1}$): 1750, 1685, 1603, 1515, 1435, 1341, 1250, 1205(sh), 1114, 1102, 1080, 1007, 840.

The following compounds were prepared from the corresponding 2-azetidinone derivative by the procedure similar to that described above.

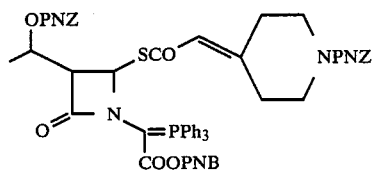

IR$_{max}^{CHCl3}$(cm$^{-1}$): 1753, 1623, 1602, 1438, 1342, 1260, 1165, 1105, 975, 842.

The following compounds were also prepared from the corresponding 2-azetidinone derivative by the procedure similar to that described in Example 131.

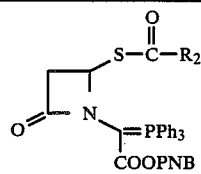

| Example No. | R$_2$ | Spectral Data |
|---|---|---|
| 132 | —CH$_2$CH$_2$C(CH$_3$)$_2$NHPNZ | IR$_{max}^{film}$ (cm$^{-1}$): 1750, 1725, 1624, 1605, 1514, 1480, 1434, 1385, 1344, 1253, 1212, 1186, 1101, 1077, 1009, 993, 841 |
| 133 | —CH$_2$C(CH$_3$)$_2$CH$_2$NHPNZ | IR$_{max}^{CHCl_3}$ (cm$^{-1}$): 1748, 1724, 1617(sh), 1606, 1516, 1434, 1344, 1116, 1104, 1019, 844 |
| 134 | —CH$_2$C(CH$_3$)$_2$NHPNZ | IR$_{max}^{CHCl_3}$ (cm$^{-1}$): 1748, 1723, 1616, 1603, 1515, 1435, 1343, 1273, 1115, 1100, 1077, 840 |
| 135 | —CH$_2$CH$_2$C(CH$_3$)$_2$CH$_2$NHPNZ | IR$_{max}^{CHCl_3}$ (cm$^{-1}$): 1750, 1724, 1618, 1605, 1518, 1436, 1390, 1346, 1260, 1228, 1107, 1081, 1013, 840 |
| 136 | —CH$_2$CH$_2$CH$_2$C(CH$_3$)$_2$NHPNZ | IR$_{max}^{CHCl_3}$ (cm$^{-1}$): 1750, 1727, 1685(sh), 1623(sh), 1607, 1520, 1440, 1350, 1260, 1205(sh), 1106, 1092, 1015, 842 |
| 137 | —CH$_2$CH$_2$COO—ONB | IR$_{max}^{CHCl_3}$ (cm$^{-1}$): 1744, 1686, 1615, 1520, 1435, 1380, 1342, 1258, 1102, 1075 |
| 138 | —C$_6$H$_4$—CH$_2$CH$_2$NHPNZ | IR$_{max}^{CHCl_3}$ (cm$^{-1}$): 1746, 1720, 1653, 1605, 1512, 1435, 1386, 1345, 1260, 1173, 1103, 1078, 905, 840 |
| 139 | —C$_6$H$_4$—NHPNZ | IR$_{max}^{film}$ (cm$^{-1}$): 1746(sh), 1735, 1653, 1620(sh), 1590, 1515, 1435, 1407, 1340, 1313, 1260, 1215, 1167, 1100, 1065, 897, 836 |
| 140 | —C$_6$H$_4$—CH$_2$NHPNZ (ortho) | IR$_{max}^{film}$ (cm$^{-1}$): 1753, 1723, 1662, 1625(sh), 1606, 1515, 1438, 1388, 1345, 1257, 1105, 1080, 1040, 1010, 996, 841 |
| 141 | —C$_6$H$_4$(OPNZ)$_2$ | IR$_{max}^{CHCl_3}$ (cm$^{-1}$): 1766, 1655(sh), 1625, 1610(sh), 1523, 1436, 1373, 1347, 1252, 1207(sh), 1157, 1120, 1108, 1080, 960 |
| 142 | —C$_6$H$_4$—COOPMB | IR$_{max}^{CHCl_3}$ (cm$^{-1}$): 1745, 1714, 1655, 1602, 1507, 1430, 1340, 1262, 1166, 1113, 902 |
| 143 | —piperidine-NPNZ | IR$_{max}^{CHCl_3}$ (cm$^{-1}$): 1748, 1688, 1615, 1603, 1515, 1434, 1343, 1260, 1220, 1118, 1103, 1077, 1010, 959, 838 |

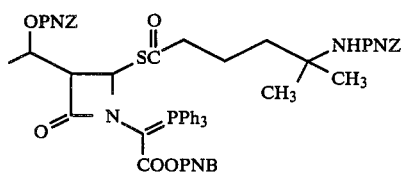

IR$_{max}^{CHCl_3}$(cm$^{-1}$): 1757, 1735(sh), 1612, 1526, 1440, 1350, 1262, 1110, 1087.

EXAMPLE 144

A mixture of 4-(4-p-methoxybenzyloxycarbonylbenzoylthio)-1-p-nitrobenzyloxycarbonyltriphenylphosphoranylidenemethyl-2-azetidinone (1.65 g) and anizole (0.54 g) in trifluoroacetic acid (4.1 ml) was stirred for 0.5 hour at 0° C. Evaporation of trifluoroacetic acid gave an oily residue which was dissolved in ethyl acetate. The ethyl acetate solution was extracted with aqueous potassium carbonate. The aqueous layer was washed with ether, acidified with hydrochloric acid and extracted with ethyl acetate. The ethyl acetate extract was washed with water, dried over anhydrous sodium sulfate and evaporated to give 4-(4-carboxybenzoylthio)-1-p-nitrobenzyloxycarbonyltriphenylphosphoranylidenemethyl-2-azetidinone.

IR$_{max}^{CHCl_3}$(cm$^{-1}$): 1750, 1710(sh), 1660, 1600, 1513, 1433, 1342, 1255, 1190, 1102, 906.

EXAMPLE 145

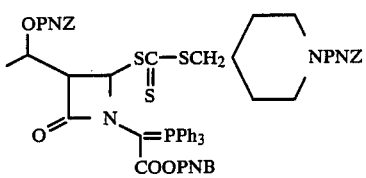

A mixture of 3-(1-p-nitrobenzyloxyethyl)-4-(4-(1-p-nitrobenzyloxycarbonylpiperidinyl)methylthio)thiocarbonylthio-2-azetidinone (3.17 g) and p-nitrobenzyl glyoxylate (1.08 g) in dry benzene (100 ml) was refluxed for 2 hours and evaporated to dryness. The residue was dissolved in dry tetrahydrofuran (60 ml). Thionyl chloride (1.67 g) was added dropwise to the solution in the presence of 2,6-lutidine (1.50 g) at −10° to −15° C. under nitrogen atmosphere. The reaction mixture was stirred at the same temperature for 15 minutes, and diluted with dichloromethane, washed with 1N hydrochloric acid and water, dried over anhydrous sodium sulfate and evaporated to dryness. The residue and triphenylphosphine (2.70 g) were dissolved in dry tetrahydrofuran (1.7 ml). The resulting solution was kept overnight at room temperature under argon atmosphere and diluted with dichloromethane, washed successively with saturated aqueous sodium bicarbonate and water, dried over anhydrous sodium sulfate and evaporated to give an oily residue which was purified by silica gel chromatography to give 3-(1-p-nitrobenzyloxycarbonyloxyethyl)-4-[4-(1-p-nitrobenzyloxycarbonylpiperidinyl)methylthio]thiocarbonylthio-1-(p-nitrobenzyloxycarbonyl)triphenylphosphoranylidenemethyl-2-azetidinone.

IR$_{max}^{CHCl_3}$(cm$^{-1}$): 1743, 1680, 1600, 1505, 1428, 1338, 1240, 1098, 835.

(3S,4R)-3-((R)-1-p-nitrobenzyloxycarbonyloxyethyl)-4-(4-(1-p-nitrobenzyloxycarbonylpiperidinyl)methylthio)thiocarbonylthio-1-(1-p-nitrobenzyloxycarbonyltriphenylphosphoranylidenemethyl)-2-azetidinone was prepared from (3S,4R)-3-((R)-1-p-nitrobenzyloxycarbonyloxyethyl)-4-(4-(1-p-nitrobenzyloxycarbonylpiperidinyl)methylthio)thiocarbonylthio-2-azetidinone by the procedure similar to that described above.

Specific rotation $[\alpha]_D^{20}$+74.3° (C=0.325, CHCl$_3$) (IR spectrum was identical with that of the above described compound.)

The following compounds were prepared from the corresponding azetidinone derivatives by the procedure similar to that described above.

EXAMPLE 146

3-(1-p-Nitrobenzyloxycarbonyloxyethyl)-4-[4-(1-p-nitrobenzyloxycarbonylpiperidinyl)thio]thiocarbonylthio-1-(p-nitrobenzyloxycarbonyl)triphenylphosphoranylidenemethyl-2-azetidinone

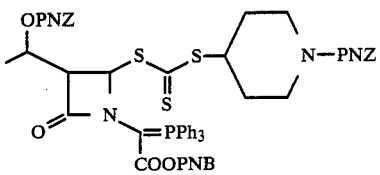

IR$_{max}^{CHCl_3}$(cm$^{-1}$): 1750, 1690, 1603, 1520, 1435, 1342, 1250, 1105, 1070, 1008.

Also, (3S,4R)-3-((R)-1-p-nitrobenzyloxycarbonyloxyethyl isomer of the above compound was prepared.

Specific rotation $[\alpha]_D^{20}$+70.4° (C=0.32, CHCl$_3$).

(IR spectrum was identical with that of the racemic compound described above.)

EXAMPLE 147

3-(1-p-Nitrobenzyloxycarbonyloxyethyl)-4-[3-(p-nitrobenzyloxycarbonylamino)-2,2-dimethylpropylthio]thiocarbonylthio-1-(p-nitrobenzyloxycarbonyl)triphenylphosphoranylidenemethyl-2-azetidinone

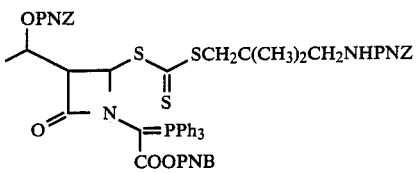

IR$_{max}^{film}$(cm$^{-1}$): 1755, 1626(sh), 1612, 1520, 1442, 1350, 1260, 1110, 1078, 850.

EXAMPLE 148

A mixture of 4-((1-p-nitrobenzyloxycarbonylpiperidinyl)thio)thiocarbonylthio-2-azetidinone (1.42 g) and p-nitrobenzylglyoxylate (0.73 g) in dry benzene (94 ml) was refluxed for 2 hours and evaporated to dryness. The residue was dissolved in dry tetrahydrofuran (42 ml). Thionyl chloride (1.15 g) was added dropwise to the solution at −10° to −15° C. in the presence of 2,6-lutidine (1.04 g) under nitrogen atmosphere. The reaction mixture was stirred for 20 minutes at the same temperature, diluted with dichloromethane, washed successively with 1N hydrochloric acid and water, dried over anhydrous sodium sulfate and evaporated to dryness. The residue and triphenylphosphine (1.69 g) in dry tetrahydrofuran (1.2 ml) were kept overnight at room temperature under argon atmosphere and diluted with dichloromethane. The solution was washed successively with saturated aqueous sodium bicarbonate and water, dried over anhydrous sodium sulfate and evaporated to give an oily residue which was purified by silica gel chromatography to give 4-[(1-p-nitrobenzyloxycarbonylpiperidinyl)thio]thiocarbonylthio-1-p-nitrobenzyloxycarbonyltriphenylphosphoranylidenemethyl-2-azetidinone.

IR$_{max}^{CHCl_3}$(cm$^{-1}$): 1758, 1690, 1520, 1435, 1343, 1272, 1248, 1107, 1079.

The following compounds were prepared from the corresponding 3-(1-p-nitrobenzyloxycarbonyloxyethyl)-2-azetidinone derivatives by the same procedures as described in Examples 145 and 148.

IR$_{max}^{Nujol}$(cm$^{-1}$): 1715, 1690, 1512, 1443, 1340, 1232, 1122.

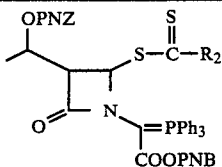

| Example No. | R$_2$ | | Spectral Data |
|---|---|---|---|
| 149 | —SCH$_2$CH$_2$-(piperidine)NPNZ | IR$_{max}^{CHCl_3}$ (cm$^{-1}$): | 1760, 1695, 1530, 1445, 1352, 1112 |
| 150 | —SCH$_2$CH=(piperidine)NPNZ | IR$_{max}^{CHCl_3}$ (cm$^{-1}$): | 1755, 1692, 1523, 1438, 1350, 1260, 1110 |
| 151 | —SCH$_2$-(tetrahydropyridine)NPNZ | IR$_{max}^{CHCl_3}$ (cm$^{-1}$): | 1762, 1705, 1615, 1530, 1445, 1355, 1265, 1115 |
| 152 | —S-(cyclohexyl) | IR$_{max}^{CHCl_3}$ (cm$^-$): | 1755, 1620, 1608, 1520, 1440, 1346, 1260, 1105 |
| 153 | —S(CH$_2$)$_3$C(CH$_3$)$_2$NHPNZ | IR$_{max}^{CHCl_3}$ (cm$^{-1}$): | 1760, 1730, 1625, 1610, 1521, 1348, 1252, 1082 |
| 154 | —S(CH$_2$)$_2$C(CH$_3$)$_2$CH$_2$NHPNZ | IR$_{max}^{CHCl_3}$ (cm$^{-1}$): | 1755, 1722, 1616, 1602, 1515, 1435, 1340, 1260, 1102, 1078, 1061 |
| 155 | —S(CH$_2$)$_2$C(CH$_3$)$_2$NHPNZ | IR$_{max}^{CHCl_3}$ (cm$^{-1}$): | 1756, 1723, 1618, 1603, 1514, 1435, 1385, 1340, 1255, 1103, 1080, 840 |
| 156 | —SCH$_2$C(CH$_3$)$_2$NHPNZ | IR$_{max}^{CHCl_3}$ (cm$^{-1}$): | 1761, 1730, 1625, 1612, 1523, 1440, 1390, 1353, 1268, 1210(sh), 1110, 1086, 845 |
| 157 | —SCH$_2$C(CH$_3$)$_2$CH$_2$NHPNZ | IR$_{max}^{CHCl_3}$ (cm$^{-1}$): | 1760, 1727, 1625, 1610, 1523, 1440, 1348, 1266(sh), 1225, 1108, 1082, 1065, 844 |
| 158 | —SCH$_2$C(CH$_3$)$_2$CH$_2$CH$_2$NHPNZ | IR$_{max}^{CHCl_3}$ (cm$^{-1}$): | 1755, 1720(sh), 1623(sh), 1608, 1513, 1436, 1346, 1103 |
| 159 | —SCH$_2$-(piperidine)NPNZ | IR$_{max}^{CHCl_3}$ (cm$^{-1}$): | 1760, 1690, 1620, 1606, 1520, 1470, 1438, 1347, 1273, 1235, 1105, 1080, 960, 844 |

EXAMPLE 160

To a mixture of piperidone monohydrate hydrochloride (6.14 g) and N,N-dimethylaminopyridine (10.7 g) in tetrahydrofuran (120 ml) and water (10 ml) was added dropwise a solution of p-nitrobenzylchloroformate (9.5 g) in tetrahydrofuran (25 ml) with ice-cooling, followed by stirring for 30 minutes at the same temperature and for 1 hour at room temperature. The reaction mixture was diluted with ethyl acetate, washed successively with 1N hydrochloric acid and water, dried over anhydrous sodium sulfate and evaporated to give crude crystals of 1-(p-nitrobenzyloxycarbonyl)-4-piperidone which were then recrystallized from isopropyl ether-diethyl ether to give pure crystals.

m.p. 123°–124° C.

EXAMPLE 161

To a mixture of 1-(p-nitrobenzyloxycarbonyl)-4-piperidone (5.46 g) in methanol (54 ml) and tetrahydrofuran (27 ml) was added sodium borohydride (373 mg), followed by stirring at 0° C. for 10 minutes. The reaction mixture was diluted with water and extracted with ethyl acetate. The extract was washed with water, dried over anhydrous sodium sulfate and evaporated to give 1-(p-nitrobenzyloxycarbonyl)-4-hydroxypiperidine.

m.p.: 91.5°~94° C.

IR$_{max}^{Nujol}$(cm$^{-1}$): 3420, 1670, 1510, 1340, 1272, 1230, 1077.

EXAMPLE 162

To a solution of 1-(p-nitrobenzyloxycarbonyl)-4-hydroxypiperidine (10.54 g) in dry pyridine (105 ml) was added p-toluenesulfonyl chloride (14.35 g) at 0° C., followed by stirring at 25° C. for 23 hours. The reaction mixture was diluted with water and extracted with diethyl ether-dichloromethane (9:1). The extract was washed successively with saturated aqueous sodium chloride, 1N hydrochloric acid, saturated aqueous sodium chloride and saturated aqueous sodium bicarbonate, dried over anhydrous sodium suflate and evaporated to give 1-(p-nitrobenzyloxycarbonyl)-4-(p-toluenesulfonyloxy)piperidine.

IR$_{max}^{Nujol}$(cm$^{-1}$): 1702, 1512, 1340, 1225,, 1173.

NMRδ(CDCl$_3$): 1.78(4H, q, J=6 Hz), 2.47(3H, s), 3.13–4.00(4H, m), 4.75(1H, quintet), 5.22(2H, s), 7.37 (2H, d, J=8 Hz), 7.50(2H, d, J=9 Hz), 8.22(2H, d, J=9 Hz).

EXAMPLE 163

A mixture of 1-(p-nitrobenzyloxycarbonyl)-4-(p-toluenesulfonyloxy)piperidine (14.78 g) in acetone (222 ml) and sodium iodide (12.71 g) was refluxed for 23 hours. The reaction mixture was filtered and the filtrate was evaporated to dryness. The residue was diluted with ethyl acetate and the extract was washed successively with aqueous 10% sodium sulfite and saturated aqueous sodium chloride, dried over anhydrous sodium sulfate and evaporated to give 1-(p-nitrobenzyloxycarbonyl)-4-iodopiperidine.

m.p.: 102.5°~104.5° C.

IR$_{max}^{Nujol}$(cm$^{-1}$): 1685, 1512, 1338, 1265, 1225.

EXAMPLE 164

To a suspension of 50% sodium hydride (1.21 g) in dry dimethylformamide (23.5 ml) was added dropwise at 10° C. a solution of thioacetic acid (2.37 g) in dry dimethylformamide (23.5 ml) under nitrogen atmosphere, followed by stirring at room temperature for 20 minutes. To the solution, a solution of 1-(p-nitrobenzyloxycarbonyl)-4-iodopiperidine (9.34 g) in dry dimethylformamide (47 ml) was added, followed by stirring at room temperature for 20 hours. The reaction mixture was diluted with water and extracted with ethyl acetate.

The extract was washed successively with 10% aqueous sodium sulfite and water, dried over anhydrous sodium sulfate and evaporated to dryness. The residue was crystallized from diethyl ether to give 1-(p-nitrobenzyloxycarbonyl)-4-thioacetoxypiperidine.

m.p.: 106.5°~107° C.

IR$_{max}^{film}$(cm$^{-1}$): 1710, 1695, 1520, 1343, 1210, 1112

EXAMPLE 165

To a solution of 1-(p-nitrobenzyloxycarbonyl)-4-thioacetoxypiperidine (3.15 g) in methanol (126 ml) was added 1N aqueous sodium hydroxide (8.9 ml) at room temperature under nitrogen atmosphere, followed by stirring at the same temperature for 10 minutes. The reaction mixture was diluted with dichloromethane. The dichloromethane layer was washed with water, dried over anhydrous sodium sulfate and evaporated to give 1-(p-nitrobenzyloxycarbonyl)-4-mercaptopiperidine.

IR$_{max}^{film}$(cm$^{-1}$): 1695, 1520, 1435, 1342, 1272, 1210.

NMRδ(CDCl$_3$): 2.68–3.32(4H, m), 3.78–4.30(2H, m), 5.22(2H, s), 7.48(2H, d, J=8.5 Hz), 8.17(2H, d, J=8.5 Hz).

EXAMPLE 166

To a solution of 4-piperidinecarboxylic acid (3.23 g) in 4N aqueous sodium hydroxide (15.6 ml) was added dropwise a solution of p-nitrobenzylchloroformate (6.45 g) in dioxane (16 ml) at 10° to 15° C., and the mixture was stirred for 1.5 hours. The resulting crystals were collected by filteration, washed with water and dried in vacuo to give 4-N-p-nitrobenzyloxycarbonyl-piperidinecarboxylic acid.

m.p.: 123°~126° C.

IR$_{max}^{Nujol}$(cm$^{-1}$): 1700(sh), 1688, 1512.

EXAMPLE 167

To a mixture of 4-N-p-nitrobenzyloxycarbonyl-piperidinylcarboxylic acid (6.16 g) and triethylamine (2.43 g) in dry tetrahydrofuran (120 ml) was added dropwise ethyl chloroformate (2.6 g) with ice-cooling, and the mixture was stirred for 30 minutes at a temperature up to 0° C. The precipitate was removed by filtration. To the filtrate was added dropwise a solution of sodium borohydride (1.52 g) in water (5 ml) with ice-cooling, The reaction mixture was stirred for 1 hour, diluted with water and the unreacted sodium borohydride was decomposed with dilute hydrochloric acid. The mixture was extracted with ethyl acetate and the extract was washed with water, dried over anhydrous sodium sulfate and evaporated to give N-p-nitrobenzyloxycarbonyl-4-hydroxymethylpiperidine.

m.p.: 67°~69° C.

IR$_{max}^{Nujol}$(cm$^{-1}$): 1695(sh), 1680, 1528, 1240.

EXAMPLE 168

To a solution of N-p-nitrobenzyloxycarbonyl-4-hydroxymethylpiperidine (20 g) in dry pyridine (127 ml) was added p-toluenesulfonyl chloride (25.8 g) with ice-cooling, and the reaction mixture was kept overnight at the same temperature, diluted with ice water and extracted with diethyl ether dichloromethane. The extract was washed successively with water, dilute hydrochloric acid, aqueous sodium bicarbonate and again water, dried over anhydrous sodium sulfate and evaporated to give an oily residue which was crystallized from methanol to give N-p-nitrobenzyloxycarbonyl-4-p-toluenesulfonyloxymethylpiperidine.

m.p.: 96.5°~99° C.

IR$_{max}^{Nujol}$(cm$^{-1}$); 1700, 1610, 1595, 1518, 1342, 1172.

EXAMPLE 169

A solution of N-p-nitrobenzyloxycarbonyl-4-p-toluenesulfonyloxymethylpiperidine (3.72 g) in dry dimethylformamide (10 ml) was added to a solution of sodium thioacetic acid (1 g) prepared from thioacetic acid and sodium hydride in dry dimethylformamide (10 ml). The reaction mixture was stirred at room temperature for 4 hours, diluted with water and extracted with ethyl acetate. The extract was washed with water, dried over anhydrous sodium sulfate and evaporated to give a residue which was then purified by silica gel column chromatography to give N-p-nitrobenzyloxycarbonyl-4-acetylthiomethylpiperidine.

m.p.: 81°~83° C.

IR$_{max}^{Nujol}$(cm$^{-1}$): 1700, 1688, 1512.

EXAMPLE 170

N-p-Nitrobenzyloxycarbonyl-4-mercaptomethyl-piperidine was prepared from N-p-nitrobenzyloxycarbonyl-4-acetylthiomethylpiperidine by the procedure similar to that described in Example 165.

m.p.: 73°~75° C.

IR$_{max}^{Nujol}$(cm$^{-1}$): 1685, 1517, 1340, 1242.

EXAMPLE 171

To a solution of oxalyl chloride (2 ml) in dry dichloromethane (50 ml) was added dropwise dry dimethyl sulfoxide (3.4 ml) at −60° C. and the resulting mixture was stirred for 10 minutes. To the mixture was added a solution of N-p-nitrobenzyloxycarbonyl-4-hydroxymethylpiperidine (5.88 g) in dry dichloromethane (40 ml) at the same temperature. After stirring for 15 minutes, triethylamine (14 ml) was added to the mixture. The reaction mixture was stirred at −60° C. for 5 minutes and at room temperature for 30 minutes, and diluted with dichloromethane. The reaction mixture was washed successively with water, dilute hydrochloric acid and again water, dried over anhydrous sodium sulfate and evaporated to give N-p-nitrobenzyloxycarbonyl-4-formylpiperidine.

IR$_{max}^{film}$(cm$^{-1}$): 2720, 1715(sh), 1690, 1512, 1345, 1220, 1125, 1080, 1010.

EXAMPLE 172

A mixture of 1-p-nitrobenzyloxycarbonyl-4-formylpiperidine (4.23 g) and t-butyloxycarbonylmethylenetriphenylphosphorane (13.54 g) in dry dichloromethane (150 ml) was stirred for 1 hour at room temperature. The reaction mixture was evaporated to give an oily residue which was purified by silica gel column chromatography to give 3-(4-(1-p-nitrobenzyloxycarbonyl)-piperidinyl)acrylic acid t-butyl ester.

m.p.: 101°~103° C.

IR$_{max}^{Nujol}$(cm$^{-1}$): 1710(sh), 1688, 1650, 1515, 1155.

EXAMPLE 173

A mixture of 3-(4-N-p-nitrobenzyloxycarbonylpiperidinyl)acrylic acid t-butyl ester (3.9 g) in m-dimethoxybenzene (2 ml) and trifluoroacetic acid (5 ml) was stirred for 15 minutes at room temperature and concentrated in vacuo. The resulting residue was dissolved in diethyl ether and the resulting crystals were collected by filtration, dried in vacuo to give 3-(4-N-p-nitrobenzyloxycarbonylpiperidinyl)acrylic acid.

m.p.: 170°~171.5° C.

IR$_{max}^{Nujol}$(cm$^{-1}$): 1690, 1640, 1350, 1223.

EXAMPLE 174

A mixture of 2,2-dimethylglutaric anhydride (19.34 g), anise alcohol (22.08 g) and triethylamine (19.39 g) in dry dioxane (360 ml) was stirred at 80° C. for 3.5 hours. The reaction mixture was evaporated and the residue was diluted with water and adjusted to pH 9 with potassium carbonate. The aqueous layer was washed with benzene, acidified with dilute hydrochloric acid and extracted with benzene. The extract was washed with water, dried over anhydrous sodium sulfate and evaporated to give p-methoxybenzyl 4-carboxy-4-methylvalerate.

IR$_{max}^{film}$(cm$^{-1}$): 1720, 1690, 1608, 1510, 1240, 1167, 1025.

NMRδ(CDCl$_3$): 1.23(6H, s), 3.76(3H, s), 4.98(2H, s).

EXAMPLE 175

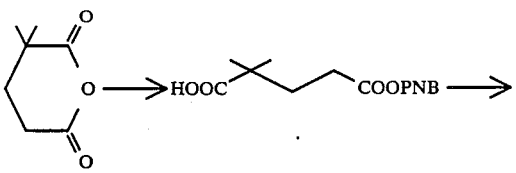

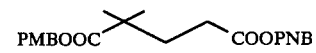

To a solution of p-nitrobenzyl 4-carboxy-4-methylvalerate (17.26 g) in dry dimethylformamide (100 ml), prepared by the procedure similar to that described in Example 174 from 2,2-dimethylglutaric anhydride and p-nitrobenzyl alcohol, was added p-methoxybenzyl chloride (9.16 g) and triethylamine (5.91 g). The reaction mixture was stirred at 80° C. for 9.5 hours, diluted with water and extracted with diethyl ether. The extract was washed successively with aqueous potassium carbonate, water, dilute hydrochloric acid and again water, dried over anhydrous sodium sulfate and evaporated to give p-nitrobenzyl 4-p-methoxybenzyloxycarbonyl-4-methylvalerate.

IR$_{max}^{film}$(cm$^{-1}$): 1730, 1614, 1517, 1345, 1300, 1246, 1175, 1030, 823.

NMRδ(CDCl$_3$): 1.20(6H, s), 3.77(3H, s), 5.03(2H, s), 5.17(2H, s).

EXAMPLE 176

To a solution of sodium sulfite hydrade (12.35 g) in water (70 ml) was added a solution of p-nitrobenzyl 4-p-methoxybenzyloxycarbonyl-4-methylvalerate (25.4 g) in tetrahydrofuran (140 ml). The reaction mixture was stirred at room temperature for 7.5 hours, diluted with water and washed with diethyl ether. The aqueous layer was acidified with hydrochloric acid and extracted with diethyl ether. The extract was washed with water, dried over anhydrous sodium sulfate and evaporated to give 4-p-methoxybenzyloxycarbonyl-4-methylvaleric acid.

IR$_{max}^{film}$(cm$^{-1}$): 1715, 1612, 1513, 1305, 1248, 1175, 1128, 1032.

NMRδ(CDCl$_3$): 1.20(6H, s), 3.76(3H, s), 5.01(2H, s).

EXAMPLE 177

Succinic acid mono-o-nitrobenzyl ester was prepared from succinic anhydride and o-nitrobenzyl alcohol by the procedure similar to that described in Example 174.

m.p.: 63°~65° C.

IR$_{max}^{Nujol}$(cm$^{-1}$): 1726, 1693, 1528, 1333, 1152,

EXAMPLE 178

To a solution of 3,3-dimethylglutaric acid (6.4 g) in dry dimethylformamide (100 ml) was added in four portions sodium hydride (50%) (1.92 g) at 30° to 40° C. under nitrogen atmosphere. The resulting mixture was stirred for 30 minutes, and p-methoxybenzyl chloride (6.28 g) in dry dimethylformamide (20 ml) was added to the mixture. The reaction mixture was stirred at 60° to 70° 1 C. for 10 hours, diluted with saturated aqueous sodium chloride and ethyl acetate. The ethyl acetate layer was extracted with aqueous potassium carbonate. The aqueous layer was acidified on ice-bath with concentrated hydrochloric acid and extracted with benzene. The extract was washed with water, dried over anhydrous sodium sulfate and evaporated to give 3,3-dimethylglutaric acid mono-p-methoxybenzyl ester.

$IR_{max}^{CHCl_3}(cm^{-1})$: 1715, 1612, 1510, 1240, 1170, 1037.

NMRδ(CDCl$_3$): 1.13(6H, s), 3.80(3H, s), 5.04(2H, s).

EXAMPLE 179 trans-1,4-Cyclohexane dicarboxylic acid mono-p-methoxybenzyl ester was prepared from trans-1,4-cyclohexanedicarboxylic acid by the procedure similar to that described in Example 178.

m.p.: 87°~89° C.

$IR_{max}^{Nujol}(cm^{-1})$: 1722, 1692, 1613, 1255, 1165.

EXAMPLE 180

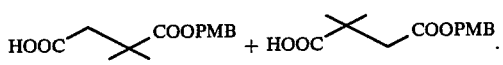

A mixture of 3-carboxy-isovaleric acid p-methoxybenzyl ester and 3-p-methoxybenzyloxycarbonylisovaleric acid was prepared from 3-carboxyisovaleric acid by the procedure similar to that described in Example 178.

$IR_{max}^{CHCl_3}(cm^{-1})$: 1720, 1610, 1240, 1170.

NMRδ(CDCl$_3$): 1.29(6H, s), 2.62(2H, s), 3.78(3H, s), 5.05(2H, bs).

The above mixture was used in the next step (Example 186) without further purification.

Example 181

To a mixture of 4-carboxy-4-methylvaleric acid p-methoxybenzyl ester (35.43 g) and triethylamine (14.14 g) in dry tetrahydrofuran (167 ml) was added dropwise a solution of ethyl chloroformate (15.23 g) in dry tetrahydrofuran (50 ml) with ice-cooling, and the mixture was stirred at 0° C. for 15 minutes. The precipitate was removed by filtration, and the filtrate was added dropwise to sodium azide (7.4 g) in water (67 ml) at a temperature up to 0° C. with stirring, followed by stirring for 30 minutes at the same temperature. The reaction mixture was diluted with benzene (200 ml) and the aqueous layer was extracted with benzene (100 ml). The combined benzene solution was washed with water, dried over anhydrous sodium sulfate and allowed to stand overnight at room temperature. After concentration to a volume of 100 to 120 ml in vacuo at a temperature below 30° C., the solution was stirred for 1 hour at 80° to 90° C. and evaporated to give an oily residue. p-Nitrobenzyl alcohol (23.32 g) and dry dioxane (22 ml) was added to the residue and the mixture was stirred for 7 hours at 120° to 130° C. and evaporated in vacuo to give an oily residue which was then purified by silica gel chromatography to give 4-methyl-4-p-nitrobenzyloxycarbonylaminovaleric acid p-methoxybenzyl ester.

$IR_{max}^{CHCl_3}(cm^{-1})$: 1725, 1610, 1515, 1342, 1244, 1118, 1080, 1030, 820.

NMRδ(CDCl$_3$): 1.29(6H, s), 3.77(3H, s), 4.98(2H, s), 5.06(2H, s).

EXAMPLE 182

A mixture of 4-methyl-4-p-nitrobenzyloxycarbonylaminovaleric acid p-methoxybenzyl ester (25 g), anisole (25 g) and trifluoroacetic acid (125 ml) was stirred for 15 minutes at room temperature. Evaporation of trifluoroacetic acid gave an oily residue which was then dissolved in diethyl ether. The ether solution was extracted with aqueous sodium carbonate. The aqueous layer was washed with diether ether, acidified with dilute hydrochloric acid and extracted with benzene. The benzene extract was washed with water, dried over anhydrous sodium sulfate and evaporated to give 4-methyl-4-p-nitrobenzyloxycarbonylaminovaleric acid.

m.p.: 108°~112° C.

$IR_{max}^{film}(cm^{-1})$: 1715, 1606, 1520, 1350, 1260, 1218, 1085, 845.

EXAMPLE 183

The following compounds were prepared from the corresponding carboxylic acids using the procedures similar to those described in Examples 180, 181 and 182.

| Starting Materials | Products |
|---|---|
| (1) 3-(p-Methoxybenzyloxycarbonyl)methyl-isovaleric acid | 3-(p-Nitrobenzyloxycarbonyl)aminomethyl-isovaleric acid<br>m.p. 142~145° C.<br>$IR_{max}^{Nujol}$ (cm$^{-1}$): 1705, 1602, 1523, 1343, 1275 |
| (2) 2-(p-Methoxybenzyloxycarbonyl)methyl-isobutyric acid | 3-(p-Nitrobenzyloxycarbonyl)amino-isovaleric acid*<br>m.p. 123~125.5° C.<br>$IR_{max}^{Nujol}$ (cm$^{-1}$): 1716, 1695, 1606, 1525, 1228 |
| (3) 3-(p-Methoxybenzyloxycarbonyl)-isovaleric acid | 2-(p-Nitrobenzyloxycarbonyl)aminomethyl-isobutyric acid*<br>m.p. 118~120° C.<br>$IR_{max}^{Nujol}$ (cm$^{-1}$): 1732, 1690, 1604, 1514, 1161 |
| (4) 4-(p-Methoxybenzyloxycarbonyl)-4-methylvaleric acid | 2-[2-(p-Nitrobenzyloxycarbonyl)amino-ethyl]isobutyric acid<br>m.p. 122~126° C.<br>$IR_{max}^{Nujol}$ (cm$^{-1}$): 1720, 1680, 1604, 1340, 1225, 1126, 1068, 920 |
| (5) trans-4-(p-Methoxybenzyloxycarbonyl)-cyclohexane carboxylic acid | trans-4-(p-Nitrobenzyloxycarbonyl)amino-cyclohexanecarboxylic acid<br>m.p. 214~217° C.<br>$IR_{max}^{Nujol}$ (cm$^{-1}$): 1685, 1604, 1541, 1515, |

| Starting Materials | Products |
|---|---|
| | 1264, 1050 |

*These two products were prepared from the mixture of compounds described in Example 180 by purification of silica gel chromatography.

EXAMPLE 184

To 3-hydroxymethylbenzylamine (1.37 g) in tetrahydrofuran (30 ml), a solution of S-p-nitrobenzyloxycarbonyl-4,6-dimethyl-2-mercaptopyrimidine (6.2 g) in tetrahydrofuran (20 ml) was added at room temperature, followed by stirring for 1 hours. The resulting precipitates were removed by filtration and the filtrate was diluted with ethyl acetate, washed with water, dried over anhydrous sodium sulfate and evaporated in vacuo to give an oily residue which was then crystallized from diethyl etherdichloromethane to give 3-(p-nitrobenzyloxycarbonyl)aminomethylbenzyl alcohol.

$IR_{max}^{film}(cm^{-1})$: 1720, 1600, 1515, 1340, 1250, 1340, 845.

Starting 3-hydroxymethylbenzylamine was prepared by reduction of m-cyanobenzoic acid with lithium aluminum hydride.

EXAMPLE 185

To 3-(p-nitrobenzyloxycarbonyl)aminomethylbenzaldehyde (1.5 g) in acetone (30 ml) was added Jones' reagent with ice-cooling, and the mixture was stirred for 2 hours. After addition of methanol (1.5 ml), the mixture was diluted with ethyl acetate, washed with water, dried over anhydrous sodium sulfate and evaporated to give 3-(p-nitrobenzyloxycarbonyl)aminomethylbenzoic acid m.p.: 180°~183° C.

$IR_{max}^{Nujol}(cm^{-1})$: 1691, 1610, 1525, 1340, 1265, 1048.

The starting 3-(p-nitrobenzyloxycarbonyl)aminomethylbenzaldehyde was prepared from the corresponding benzyl alcohol by the procedure similar to that described in Example 171.

EXAMPLE 186

To a mixture of 4-methyl-4-(p-nitrobenzyloxycarbonyl)aminovaleric acid (14.0 g) and triethylamine (5.25 g) in tetrahydrofuran (280 ml), ethyl chloroformate (5.64 g) was added with ice-cooling and then stirred for 30 minutes. The resulting triethylamine hydrochloride was removed by filtration. To filtrate was added sodium borohydride (5 g) in water (90 mg) with ice-cooling, and the mixture was stirred for 1.5 hours. The reaction mixture was concentrated to a volume of 120 ml in vacuo and extracted with dichloromethane. The dichloromethane layer was washed with diluted hydrochloric acid and then water, dried over anhydrous sodium sulfate and evaporated in vacuo to give an oily residue which was then purified by silica gel chromatography to give 4-methyl-4-(p-nitrobenzyloxycarbonyl)aminopentanol.

$IR_{max}^{film}(cm^{-1})$: 1710, 1607, 1515, 1343, 1260, 1213, 1086.

NMRδ(CDCl$_3$): 1.32(6H, s), 5.09(2H, s).

EXAMPLE 187

A mixture of 4-methyl-4-(p-nitrobenzyloxycarbonyl)aminopentanol (1.63 g) and p-toluenesulfonyl chloride (2.3 g) in pyridine (17 ml) was allowed to stand at 5° C. overnight. The reaction mixture was diluted with diethyl ether and water, washed successively with dilute hydrochloric acid, aqueous sodium bicarbonate and water, dried over anhydrous sodium sulfate and evaporated to give 5-p-toluenesulfonyloxy-2-methyl-2-(p-nitrobenzyloxycarbonyl)aminopentane.

$IR_{max}^{film}(cm^{-1})$: 1725, 1605, 1520, 1343, 1258, 1173, 1092, 958, 915.

NMRδ(CDCl$_3$): 1.25(6H, s), 2.42(3H, s), 5.08(2H, s).

EXAMPLE 188

A mixture of thiobenzoic acid (890 mg) and sodium hydride (50%) (220 mg) in dimethylformamide (8 ml) was stirred for 10 minutes with ice-cooling. 5-p-Toluenesulfonyloxy-2-methyl-2-(p-nitrobenzyloxycarbonyl)aminopentane (1.64 g) in dimethylformamide (8 ml) was added thereto, followed by stirring for 25 minutes. The reaction mixture was diluted with ethyl acetate, washed with dilute hydrochloric acid and then water, dried over anhydrous sodium sulfate and evaporated to give an oily residue which was then purified by silica gel chromatography to give 5-benzoylthio-2-methyl-2-(p-nitrobenzyloxycarbonyl)aminopentane.

$IR_{max}^{film}(cm^{-1})$: 1723, 1658, 1606, 1515, 1343, 1252, 1206, 1080, 910.

NMRδ(CDCl$_3$): 1.30(6H, s), 5.06(2H, s).

EXAMPLE 189

The following compounds were prepared from the corresponding carboxylic acids using the procedures similar to those described in Examples 186, 187 and 188.

| Starting Materials | Products |
|---|---|
| (1) 4-(p-Nitrobenzyloxycarbonyl)amino-3,3-dimethyl-n-butyric acid | 4-Benzoylthio-2,2-dimethyl-1-(p-nitrobenzyloxycarbonyl)aminobutane<br>m.p. 69~70° C.<br>$IR_{max}^{Nujol}(cm^{-1})$: 1702, 1650, 1550, 1520, 1252, 1210 |
| (2) 3-(p-Nitrobenzyloxycarbonyl)amino-3-methyl-n-butyric acid | 4-Acetylthio-2-methyl-2-(p-nitrobenzyloxycarbonyl)aminobutane<br>$IR_{max}^{film}(cm^{-1})$: 1720, 1682, 1518, 1340, 1255, 1210, 1094, 950, 850<br>NMRδ(CDCl$_3$): 1.37(6H,s), 2.33(3H,s), 5.23(2H,s) |
| (3) 3-(p-Nitrobenzyloxycarbonyl)amino-2,2-dimethylpropionic acid | 3-Acetylthio-2,2-dimethyl-3-(p-nitrobenzyloxycarbonyl)aminopropane<br>$IR_{max}^{film}(cm^{-1})$: 1720, 1680, 1600, 1528, 1340, 1120, 950, 845 |

| Starting Materials | Products |
|---|---|
| (4) 4-(p-Nitrobenzyloxycarbonyl)amino-2,2-dimethyl-n-butyric acid | 4-(p-Nitrobenzyloxycarbonyl)amino-2,2-dimethyl-1-acetylthiobutane<br>NMRδ(CDCl$_3$): 0.95(6H,s), 2.37(3H,s), 5.22(2H,s)<br>IR$_{max}^{film}$(cm$^{-1}$): 1700, 1600, 1510, 1340, 1240, 1125, 950, 845 |

EXAMPLE 190

4-(p-Nitrobenzyloxycarbonyl)amino-4-methylpentanethiol was prepared from 5-benzoylthio-2-methyl-2-(p-nitrobenzyloxycarbonyl)aminopentane by the procedure similar to that described in Example 165.

IR$_{max}^{film}$(cm$^{-1}$): 1715, 1605, 1515, 1342, 1250, 1208, 1080.

NMRδ(CDCl$_3$): 1.32(6H, s), 2.52(2H, q, J=6.5 Hz), 5.15(2H, s).

The following thiol derivatives were prepared from the corresponding thioacetate or thiobenzoate derivatives by the procedure similar to that described above and were used in the next reaction.

| Starting Materials | Products |
|---|---|
| (1) 4-Benzoylthio-2,2-dimethyl-1-(p-nitrobenzyloxycarbonyl)aminobutane | 4-(P-Nitrobenzyloxycarbonyl)amino-3,3-dimethylbutanethiol<br>IR$_{max}^{film}$(cm$^{-1}$): 1710, 1608, 1520, 1350, 1250, 1088 |
| (2) 4-Acetylthio-2-methyl-2-(p-nitrobenzyloxycarbonyl)aminobutane | 3-(p-nitrobenzyloxycarbonyl)amino-3-methylbutanethiol<br>IR$_{max}^{film}$(cm$^{-1}$): 1715, 1605, 1517, 1342, 1258, 1212, 1085 |
| (3) 3-Acetylthio-2,2-dimethyl-3-(p-nitrobenzyloxycarbonyl)aminopropane | 3-(p-Nitrobenzyloxycarbonyl)amino-2,2-dimethylpropanethiol<br>IR$_{max}^{film}$(cm$^{-1}$): 1710, 1608, 1520, 1343, 1237 |
| (4) 4-(p-Nitrobenzyloxycarbonyl)amino-2,2-dimethyl-1-acetylthiobutane | 4-(p-Nitrobenzyloxycarbonyl)amino-2,2-dimethylbutanethiol<br>IR$_{max}^{film}$(cm$^{-1}$): 1710, 1602, 1512, 1342, 1245 |

EXAMPLE 191

1-p-Nitrobenzyloxycarbonyl-4-piperididenemethylcarboxylic acid was prepared from 1-p-nitrobenzyloxycarbonyl-4-piperidone and t-butoxycarbonylmethylenetriphenylphosphorane by the procedures similar to those described in Examples 172 and 173.

m.p.: 188°~191° C.

IR$_{max}^{Nujol}$(cm$^{-1}$): 1678, 1625, 1510, 1210.

EXAMPLE 192

(a) After dropwise addition of 1N sodium hydroxide to a solution of 1-p-nitrobenzyloxycarbonyl-4-piperididenemethylcarboxylic acid t-butyl ester (7.54 g), p-toluenesulfonyl hydrazide (4.46 g) and triethyl borate (3.65 g) in ethanol (100 ml) under refluxing over 1.5 hours. The mixture was refluxed for 1 hour, and the reaction mixture was diluted with water and extracted with dichloromethane. The dichloromethane layer was washed successively with 2N sodium hydroxide and water, dried over anhydrous sodium sulfate and evaporated to give an oily residue which was then purified by silica gel chromatography to give 1-p-nitrobenzyloxycarbonyl-4-piperidinylacetic acid t-butyl ester.

m.p.: 99°~100° C.

IR$_{max}^{Nujol}$(cm$^{-1}$): 1732, 1685, 1605, 1518

(b) 1-p-Nitrobenzyloxycarbonyl-4-piperidinylacetic acid was prepared from the t-butyl ester obtained above by the procedure similar to that described in Example 173.

m.p.: 136°~137.5° C.

IR$_{max}^{Nujol}$(cm$^{-1}$): 1733, 1662, 1515, 1255.

EXAMPLE 193

1-p-Nitrobenzyloxycarbonyl-3-piperidone was prepared from 3-hydroxypiperidine by the procedures similar to those described in Examples 184 and 171.

IR$_{max}^{film}$(cm$^{-1}$): 1708, 1520, 1430, 1342, 1315, 1266, 1215, 1108.

NMRδ(CDCl$_3$): 3.69(2H, t, J=6 Hz), 4.10(2H, s), 5.24(2H, s).

EXAMPLE 194

Cis and trans isomers of 1-p-nitrobenzyloxycarbonyl-3-piperidinylidenemethylcarboxylic acid were prepared from 1-p-nitrobenzyloxycarbonyl-3-piperidone by the procedures similar to those described in Examples 172 and 173.

trans isomer m.p.: 164°-165.5° C.

IR$_{max}^{Nujol}$(cm$^{-1}$): 1705, 1688, 1642, 1523, 1223, 1109.

cis isomer m.p.: 202°~203° C.

IR$_{max}^{Nujol}$(cm$^{-1}$): 1700, 1643, 1512, 1342, 1232.

EXAMPLE 195

1-p-Nitrobenzyloxycarbonyl-3-piperidinylacetic acid was prepared from the mixture of cis and trans isomers of 1-p-nitrobenzyloxycarbonyl-3-piperidinylidenemethylcarboxylic acid t-butyl ester by the procedure similar to that described in Example 192.

m.p.: 165°~166.5° C.

IR$_{max}^{Nujol}$(cm$^{-1}$): 1712, 1692, 1518, 1260, 1155.

EXAMPLE 196

3-(4-(1-p-Nitrobenzyloxycarbonyl)piperidinyl)propionic acid was prepared from 3-(4-(1-p-nitrobenzyloxycarbonyl)piperidinyl)acrylic acid t-butyl ester by the procedure similar to that described in Example 192.

m.p.: 99°~101° C.

$IR_{max}^{CH_2Cl_2}(cm^{-1})$: 1700, 1607, 1525, 1218, 1122.

EXAMPLE 197

5-p-Nitrobenzyloxycarbonylamino-4,4-dimethyl-2-pentenoic acid p-methoxybenzyl ester was prepared from 2-(p-nitrobenzyloxycarbonylamino)methyl-isobutylic acid by the procedures similar to those described in Examples 186, 171 and 172.

$IR_{max}^{film}(cm^{-1})$: 1718, 1650, 1613, 1520, 1462, 1347, 1243, 1032, 820.

NMRδ(CDCl$_3$): 1.08(6H, s), 3.17(2H, d, J=6.5 Hz), 3.79(3H, s), 5.10(2H, s), 5.15(2H, s), 5.83(1H, d, J=16 Hz), 6.87(1H, d, J=16 Hz).

EXAMPLE 198

5-p-Nitrobenzyloxycarbonylamino-4,4-dimethyl-2-pentenoic acid was prepared from 5-p-nitrobenzyloxycarbonylamino-4,4-dimethyl-2-pentenoic acid p-methoxybenzyl ester by the procedure similar to that described in Example 173.

m.p.: 123~126° C.

$IR_{max}^{Nujol}(cm^{-1})$: 1725, 1693, 1642, 1611, 1520, 1142.

EXAMPLE 199

5-p-Nitrobenzyloxycarbonylamino-4,4-dimethylpentanic acid was prepared from 5-p-nitrobenzyloxycarbonylamino-4,4-dimethyl-2-pentenoic acid p-methoxybenzyl ester by the procedure similar to that described in Example 192.

$IR_{max}^{Nujol}(cm^{-1})$: 1708, 1660, 1603, 1519, 1240, 1132, 1065.

NMRδ(CDCl$_3$): 0.89(6H, s), 3.06(2H, d, J=7 Hz), 5.25(2H, s).

EXAMPLE 200

5-p-Nitrobenzyloxycarbonylamino-5-methylhexanoic acid was prepared from 3-p-nitrobenzyloxycarbonylaminoisovaleric acid by the procedures similar to those described in Examples 197 and 199.

m.p.: 105°~108° C.

$IR_{max}^{film}(cm^{-1})$: 1710, 1520, 1260, 1212, 1090.

EXAMPLE 201

(a) A mixture of 1-p-nitrobenzyloxycarbonyl-4-mercaptopiperidine (1.19 g), t-butyl bromoacetate (780 mg) and 1,8-diazabicyclo[5,4,0]undec-7-ene (DBU) (608 mg) in benzene (10 ml) was stirred for 5 minutes under nitrogen atmosphere. The reaction mixture was washed successively with water, dilute hydrochloric acid and water, dried over anhydrous sodium sulfate and evaporated to give 1-p-nitrobenzyloxycarbonyl-4-t-butoxycarbonylmethylthiopiperidine.

$IR_{max}^{film}(cm^{-1})$: 1723(sh), 1713, 1610, 1523, 1350, 1298, 1278, 1250, 1213, 1013, 853.

NMRδ(CDCl$_3$): 1.46(9H, s), 3.15(2H, s), 5.18(2H, s).

(b) 1-p-Nitrobenzyloxycarbonyl-4-carboxymethylthiopiperidine was prepared from 1-p-nitrobenzyloxycarbonyl-4-t-butoxycarbonylmethylthiopiperidine by the procedure similar to that described in Example 173.

m.p.: 82°~86° C.

$IR_{max}^{film}(cm^{-1})$: 1725(sh), 1714, 1608, 1518, 1346, 1273, 1248, 1210, 1010.

EXAMPLE 202

To a solution of sodium β-chloropivalate, prepared from β-chloropivalic acid (13.66 g) and 50% sodium hydride (4.80 g) in dimethylformamide (110 ml) was added dropwise trimethyl chlorosilane (10.85 g) in dimethylformamide (10 ml) at −5° C. to −3° C. After stirring for 1 hour sodium thiobenzoate, prepared from thiobenzoic acid (13.8 g) and 50% sodium hydride (4.80 g) in dimethylformamide (70 ml), was added dropwise thereto at −5° C. to −8° C. After addition of sodium iodide (15.0 g), the mixture was stirred at room temperature for 3 days and then at 40° C. for 7 days. The reaction mixture was diluted with ice-water and extracted with ethyl acetate. The ethyl acetate extract was washed with water, dried over anhydrous sodium sulfate and evaporated in vacuo. The residue was recrystallized from diisopropyl ether-petroleum ether to give β-benzoylthiopivalic acid.

$IR_{max}^{film}(cm^{-1})$: 1703, 1663, 1472, 1448, 1208, 1175, 905.

NMR(CDCl$_3$): 1.35(6H, s), 3.39(2H, s).

EXAMPLE 203

2-(p-Nitrobenzyloxycarbonyl)amino-2-methyl-propanethiol was prepared from β-benzoylthiopivalic acid by the procedures similar to those described in Examples 181, 182 and 165.

$IR_{max}^{film}(cm^{-1})$: 1718, 1600, 1518, 1343, 1242.

EXAMPLE 204

(a) To 4-formylbenzoic acid t-butyl ester (12.27 g) in dichloromethane (250 ml) were added dropwise 50% aqueous sodium hydroxide (5.86 g) and then triethylphosphonoacetate (16.44 g), and the mixture was stirred under nitrogen atmosphere at 25° C. for 40 minutes. The reaction mixture was washed with water, dried over anhydrous sodium sulfate, evaporated to give an oily residue which was then purified by silica gel chromatography to give 3-(4-tert-butyloxycarbonylphenyl)acrylic acid ethyl ester.

The starting 4-formylbenzoic acid t-butyl ester was prepared from 4-formylbenzoic acid chloride by esterification with t-butanol.

$IR_{max}^{film}(cm^{-1})$: 1720, 1710, 1638, 1605, 1366, 1295, 1117, 1105.

NMRδ(CDCl$_3$): 1.33(3H, t, J=6.5 Hz), 1.60(9H, s), 4.24(2H, q, J=6.5 Hz, 6.46(1H, d, J=15 Hz).

(b) A mixture of 3-(4-t-butyloxycarbonylphenyl)acrylic acid ethyl ester (11.52 g) and 5% palladium-charcoal in ethanol (115 ml) was stirred under hydrogen atmosphere at room temperature. The catalyst was removed by filtration and washed with ethanol. The combined solution was evaporated to give 3-(4-tert-butyloxycarbonylphenyl)propionic acid ethyl ester.

$IR_{max}^{film}(cm^{-1})$: 1737, 1712, 1368, 1292, 1265, 1166, 1116, 850.

NMRδ(CDCl$_3$): 1.20(3H, t, J=7.5 Hz), 1.59(9H, s), 4.09(2H, q, J=7.5 Hz).

(c) 4-(t-Butoxycarbonyl)phenylpropionic acid was prepared from the above ethyl ester by the procedure similar to that described in Example 65.

m.p.: 89°~90° C.

$IR_{max}^{Nujol}(cm^{-1})$: 1696, 1603, 1285, 1161, 1105.

EXAMPLE 205

4-(2-(p-Nitrobenzyloxycarbonylamino)ethyl)benzoic acid was prepared from 4-t-butoxycarbonyl)phenylpropionic acid by the procedures similar to those described in Examples 181 and 182.

m.p.: 173°~175° C.

IR$_{max}^{Nujol}$(cm$^{-1}$): 1688, 1607, 1543, 1510, 1255.

EXAMPLE 206

To trans-4-aminomethylcyclohexanecarboxylic acid (3.93 g) in 4N aqueous sodium hydroxide (8 ml), p-nitrobenzylchloroformate (3.38 g) in dioxane (8 ml) was added dropwise with ice-cooling and stirred for 1.5 hours. After filtration to remove the insoluble material, the filtrate was acidified with hydrochloric acid with ice-cooling. The resulting crystals were filtered, washed with cooled water and dried up in vacuo to give trans-4-p-nitrobenzyloxycarbonylaminomethylcyclohexanecarboxylic acid.

m.p.: 164°~166° C.

IR$_{max}^{Nujol}$(cm$^{-1}$): 1713, 1674, 1602, 1512, 1340, 1275, 1263.

EXAMPLE 207

A mixture of p-aminobenzoic acid (2.06 g) and bis trimethylsilylacetamide (7.42 ml) in tetrahydrofuran (42 ml) was stirred under nitrogen atmosphere at 0° C. for 4 hours, and p-nitrobenzylchloroformate (3.23 g) in tetrahydrofuran (10 ml) was added thereto at the same temperature. The mixture was stirred for 3 hours and, after addition of methanol (3 ml) at -°~25° C., stirred for 25 minutes and diluted with diethyl ether (130 ml). The resulting crystals were filtrated, washed with diethyl ether and dried in vacuo to give 4-p-nitrobenzyloxycarbonylaminobenzoic acid.

m.p. (dec): 245°~254° C.

IR$_{max}^{Nujol}$(cm$^{-1}$): 1730, 1667, 1590, 1531, 1508, 1346, 1218, 1050, 848.

EXAMPLE 208

3,4-Di(p-nitrobenzyloxycarbonyloxy)benzoic acid was prepared from 3,4-dihydroxybenzaldehyde by the procedures similar to those described in Examples 66 and 185.

m.p.: 170°~172° C.

IR$_{max}^{KBr}$(cm$^{-1}$): 1772, 1758, 1686, 1525, 1280, 1240.

EXAMPLE 209

A mixture of 4-formylbenzoic acid (7.5 g), triethylamine (5.2 g) and p-methoxybenzyl chloride (7.6 g) in dimethylformamide (75 ml) was stirred at room temperature for 2 hours and then at 80° C. for 6 hours. The reaction mixture was diluted with water and extracted with diethyl ether. The ether extract was washed with aqueous sodium bicarbonate and then water, dried over anhydrous sodium sulfate and evaporated to give 4-formylbenzoic acid p-methoxybenzyl ester which was then converted into 4-carboxybenzoic acid p-methoxybenzyl ester by the procedure similar to that described in Example 185.

m.p.: 164°~165° C.

IR$_{max}^{Nujol}$(cm$^{-1}$): 1712, 1686, 1275, 1255, 1102.

EXAMPLE 210

(a) To methyl methylthiomethyl sulfoxide (2.23 g) in dry tetrahydrofuran (10 ml) was added dropwise n-butyl lithium (1.15 g) in dry hexane (11.6 ml) at −60° to −70° C. under nitrogen atmosphere and the mixture was stirred for 20 minutes at the same temperature. Subsequently, 1-p-nitrobenzyloxycarbonyl-4-piperidone (5.0 g) in dry tetrahydrofuran (30 ml) was added dropwise thereto at −55° to −70° C. under nitrogen atmosphere. The reaction mixture was diluted with dichloromethane (200 ml) and water (215 ml), warmed slowly to room temperature, dried over anhydrous sodium sulfate and evaporated to give an oily residue which was then purified by silica gel chromatography to give 1-p-nitrobenzyloxycarbonyl-4-hydroxy-4-methylsulfinylmethylthiomethylpiperidine.

(b) A solution of the above methylsulfinylmethylthiomethyl derivative (1.61 g) in hydrochloric acid (8.05 ml) and tetrahydrofuran (20 ml) was stirred for 1.5 hours at room temperature. The reaction mixture diluted with dichloromethane was washed with water, dried over anhydrous sodium sulfate and evaporated to give 1-p-nitrobenzyloxycarbonyl-4-hydroxy-4-formylpiperidine.

IR$_{max}^{film}$(cm$^{-1}$): 3370, 1700, 1610, 1522, 1420, 1350, 1242, 1090, 1015, 852.

NMRδ(CDCl$_3$): 5.22(2H, s), 7.49(2H, d, J=8.5 Hz), 8.17(2H, d, J=8.5 Hz), 9.49(1H, s).

EXAMPLE 211

To 1-p-nitrobenzyloxycarbonyl-4-hydroxy-4-(2-t-butoxycarbonylethenyl)piperidine (1.65 g) in pyridine (16.5 ml) was added dropwise phosphoryl chloride (2.5 ml) with ice-cooling. The reaction mixture was stirred for 6 hours at room temperature, diluted with water and extracted with dichloromethane. The dichloromethane layer was washed successively with water, dilute hydrochloric acid, water, aqueous sodium bicarbonate and water, dried over anhydrous sodium sulfate and evaporated to give 1-p-nitrobenzyloxycarbonyl-4-(2-t-butoxycarbonylethenyl)-3,4-dehydropiperidine which was then converted into 1-p-nitrobenzyloxycarbonyl-4-(2-carboxylethenyl)-3,4-dehydropiperidine by a procedure similar to that described in Example 173.

IR$_{max}^{Nujol}$(cm$^{-1}$): 1692, 1620, 1542, 1416, 1345, 1281, 1235, 1097, 858.

NMRδ(CD$_3$SOCD$_3$): 5.24(2H, s), 5.80(1H, d, J=16 Hz), 6.22(1H, m), 7.22(1H, d, J=16 Hz), 7.63(2H, d, J=8.5 Hz), 8.18(2H, d, J=8.5 Hz).

The starting 1-p-nitrobenzyloxycarbonyl-4-hydroxy-4-(2-t-butoxycarbonylethenyl)piperidine was prepared from 1-p-nitrobenzyloxycarbonyl-4-hydroxy-4-formylpiperidine and t-butoxycarbonylmethylene triphenyl phosphorane by the procedure similar to that described in Example 172.

EXAMPLE 212

A (E),(Z)-mixture of 2-methyl-3-(4-N-p-nitrobenzyloxycarbonylpiperidinyl)acrylic acid was prepared from 1-p-nitrobenzyloxycarbonyl-4-formylpiperidine and α-t-butoxycarbonylethylidene-triphenylphosphorane by the procedures similar to those described in Examples 172 and 173.

IR$_{max}^{Nujol}$(cm$^{-1}$): 1680, 1517, 1338, 1222, 1158, 1103.

NMRδ(CDCl$_3$): 1.86(3/2H, s), 1.89(3/2H, s), 5.26(2H, s), 6.69(½H, d, J=8 Hz), 6.72 (½H, d, J=8 Hz), 7.54(2H, d, J=8 Hz), 8.26 (2H, d, J=8 Hz).

EXAMPLE 213

1-p-Nitrobenzyloxycarbonyl-4-(2-mercaptoethyl)-piperidine was prepared from 1-p-nitrobenzyloxycarbonyl-4-piperidinylacetic acid by the procedures similar to those described in Examples 167, 168, 169 and 170.

IR$_{max}^{film}$(cm$^{-1}$): 1700, 1608, 1521, 1345, 1239, 1120, 1080, 1013, 845.

NMRδ(CDCl₃): 1.33(1H, t, J=7 Hz), 5.20(2H, s), 7.47(2H, d, J=8.5 Hz), 8.17(2H, d, J=8.5 Hz).

EXAMPLE 214

To 1-p-nitrobenzyloxycarbonyl-4-hydroxy-4-acetylthiomethylpiperidine (1.1 g) in pyridine (11 ml) was added dropwise thionyl chloride (0.4 ml) with ice-cooling.

The reaction mixture was stirred for 30 minutes, diluted with water and extracted with ethyl acetate. The extract was washed with water, dried over anhydrous sodium sulfate and evaporated in vacuo. The resulting oily residue was purified by silica gel chromatography to give 1-p-nitrobenzyloxycarbonyl-4-acetylthiomethyl-3,4-dehydropiperidine which was then converted into 1-p-nitrobenzyloxycarbonyl-4-mercaptomethyl-3,4-dehydropiperidine by the procedure similar to that described in Example 170.

IR$_{max}^{film}$(cm⁻¹): 1704, 1612, 1521, 1435, 1343, 1280, 1239, 1108, 966, 853.

NMRδ(CDCl₃): 1.45(1H, t, J=8 Hz), 3.13(2H, d, J=8 Hz), 3.60(2H, t, J=5.5 Hz), 5.22(2H, s), 5.58(1H, m), 7.46(2H, d, J=8 Hz), 8.13(2H, d, J=8 Hz).

The starting 1-p-nitrobenzyloxycarbonyl-4-hydroxy-4-acetylthiomethylpiperidine was prepared from 1-p-nitrobenzyloxycarbonyl-4-hydroxy-4-formylpiperidine by the procedures similar to those described in Examples 161, 168 and 169.

EXAMPLE 215

4-p-Nitrobenzyloxycarbonyloxymethyl-cyclohexanecarboxylic acid was prepared from 4-formylcyclohexanecarboxylic acid p-methoxybenzyl ester by the procedures similar to those described in Examples 162, 66 and 182.

IR$_{max}^{Nujol}$(cm⁻¹): 1741, 1702, 1610, 1532, 1347, 1262, 995, 840.

NMRδ(CDCl₃): 4.01(2H, d, J=5.5 Hz), 5.24(2H, s), 7.51(2H, d, J=8 Hz), 8.17(2H, d, J=8 Hz), 10.10 (1H, br. s).

EXAMPLE 216

To a mixture of 2-(1-p-nitrobenzyloxycarbonyl-4-piperidinylidene)ethyl alcohol (1.13 g) and triphenyl phosphine (1.94 g) in tetrahydrofuran (65 ml) was added N-bromosuccinimide (1.31 g) at room temperature and stirred for 2 hours. The reaction mixture was filtered to remove any insoluble materials and the filtrate was concentrated in vacuo to give an oily residue which was purified by silica gel chromatography to give 2-(1-p-nitrobenzyloxycarbonyl-4-piperidinylidene)ethylbromide.

IR$_{max}^{CHCl3}$(cm⁻¹): 1695, 1605, 1520, 1432, 1342, 1218, 1108, 981, 850.

NMRδ(CDCl₃): 2.27(4H, dd, J=5 and 12 Hz), 3.53(4H, t, J=6 Hz), 3.97(2H, d, J=8 Hz), 5.20(2H, s), 5.62(1H, t, J=8 Hz), 7.44(2H, d, J=8 Hz), 8.16 (2H, d, J=8 Hz).

The starting alcohol was prepared from 1-p-nitrobenzyloxycarbonyl-4-piperidinylidenemethylcarboxylic acid by the procedure similar to that described in Example 186.

EXAMPLE 217

2-(1-p-Nitrobenzyloxycarbonyl-4-piperidinylidene)ethylmercaptan was prepared from the bromide prepared in Example 216 by treatment with sodium thioacetate by the procedure similar to that described in Example 202 and hydrolysis by the procedure similar to that described in Example 165. The resulting product had the following spectra.

IR$_{max}^{Nujol}$(cm⁻¹): 1695, 1528, 1346, 1220, 1105, 997, 858.

NMRδ(CDCl₃): 1.45(1H, t, J=7 Hz), 2.24(4H, dd, J=5 and 11 Hz), 3.18(2H, t, J=7 Hz), 5.24(2H, s), 5.46(1H, t, J=7 Hz), 7.50(2H, d, J=8 Hz), 8.16 (2H, d, J=8 Hz).

EXAMPLE 218

4-[2-(p-Nitrobenzyloxycarbonyl)amino ethyl]-1-cyclohexanecarboxylic acid was prepared from 4-formyl-1-cyclohexanecarboxylic acid p-methoxybenzyl ester and p-nitrobenzyloxycarbonylmethylenetriphenylphosphorane by the procedures similar to those described in Examples 172, 192(a), 176, 181 and 182.

IR$_{max}^{film}$(cm⁻¹): 3400, 1680, 1515, 1340, 1245.

EXAMPLE 219

5-(p-Nitrobenzyloxycarbonyl)amino-2-pentenoic acid was prepared from β-alanine by the procedures similar to those described in Examples 184, 186, 171, 172 and 173.

IR$_{max}^{Nujol}$(cm⁻¹): 3320, 1700(sh), 1688, 1648, 1510, 1345, 1268, 1147, 970.

The symbols used herein have the meanings defined below.

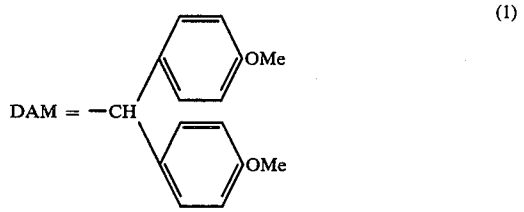

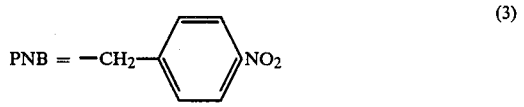

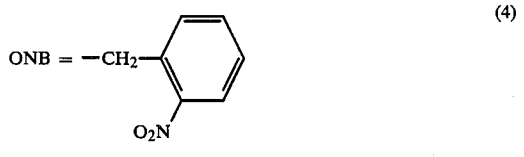

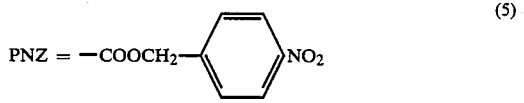

Me = —CH₃ n-Bu = —CH₂CH₂CH₂CH₃

-continued

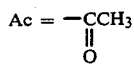 (9)

While the invention has been described in detail and with reference to specific embodiments thereof, it will be apparent to one skilled in the art that various changes and modifications can be made therein without departing from the spirit and scope thereof.

What is claimed is:

1. A compound of the formula:

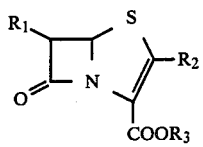

wherein:
$R_1$ is hydrogen, 1-hydroxyethyl or a protected 1-hydroxyethyl conventional protecting group for a hydroxyl group,
$R_2$ is a group of the formula (1) to (5):

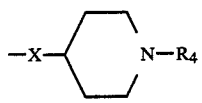 (1)

wherein $R_4$ is hydrogen or a conventional protecting group for an amino group, and X is a group of the formula: —(CH$_2$)$_l$—, —S(CH$_2$)$_l$—, —CH$_2$S—, —CH=CH— or —C(CH$_3$)=CH— wherein $l$ is 0, 1 or 2;

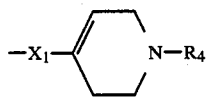 (2)

wherein $R_4$ is as defined above, and $X_1$ is a group of the formula: —CH=CH— or —SCH$_2$—;

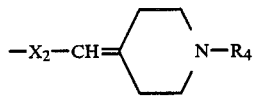 (3)

wherein $R_4$ is as defined above, and $X_2$ is a chemical bond (a direct linkage) or a group of the formula: —SCH$_2$—;

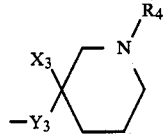 (4)

wherein $R_4$ is as defined above, $X_3$ is hydrogen and $Y_3$ is a methylene group (—CH$_2$—), or $X_3$ and $Y_3$ may be linked together to form a methylinilydene group (—CH=);

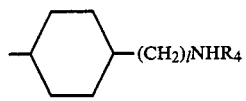 (5)

wherein $R_4$ and $l$ are as defined above;
$R_3$ is hydrogen or a conventional protecting group for a carboxyl group.

2. A compound as claimed in claim 1, wherein $R_1$ is hydrogen or 1-hydroxyethyl;
$R_2$ is a group of the formula:

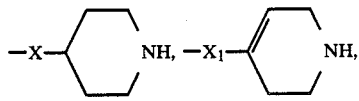

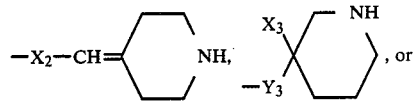

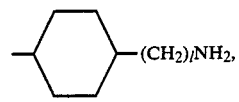

wherein $l$, X, $X_1$, $X_2$, $X_3$ and $Y_3$ are as defined above; and
$R_3$ is hydrogen.

3. A compound as claimed in claim 1, wherein:
$R_1$ is 1-hydroxyethyl,
$R_2$ is the group of the formula:

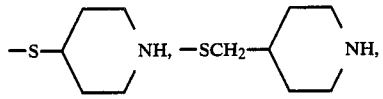

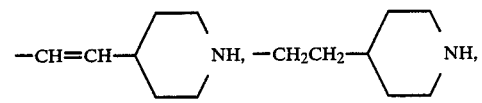

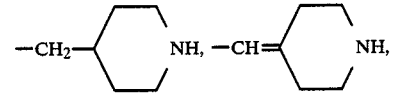

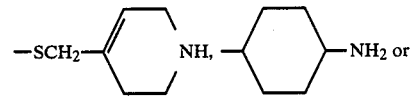

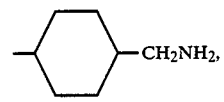

and
$R_3$ is hydrogen.

4. A compound as claimed in claim 2, wherein $R_2$ is a group of the formula:

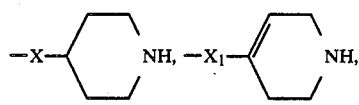

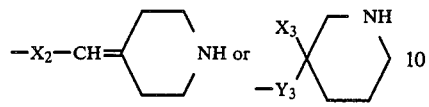

wherein X, X₁, X₂, X₃ and Y₃ are as defined above.

5. A compound as claimed in claim 2, wherein $R_2$ is a group of the formula:

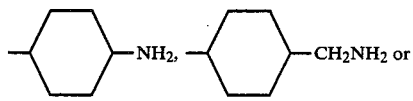

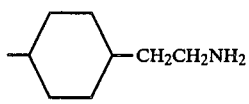

6. 2-(4-Piperidinylthio)-6-(1-hydroxyethyl)-penem-3-carboxylic acid or 2-(4-piperidinylmethylthio)-6-(1-hydroxyethyl)-penem-3-carboxylic acid.

7. 2-(4-Aminocyclohexyl)-6-(1-hydroxyethyl)-penem-3-carboxylic acid or 2-(4-aminomethylcyclohexyl)-6-(1-hydroxyethyl)-penem-3-carboxylic acid.

8. A non-toxic, pharmaceutically acceptable salt of a compound claimed in any one of claims 2, 3, 4, 6 and 7.

9. A (5R)-compound of the compound as claimed in any one of claims 2, 3, 4, 6 and 7.

10. A (5R, 6S, 8R)-compound of the compound as claimed in any one of claims 6 and 7.

11. A (5R, 6R, 8R)-compound of the compound as claimed in any one of claims 6 and 7.

12. A compound of the formula:

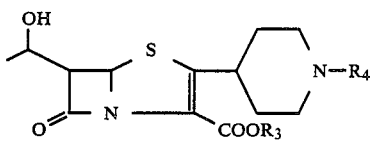

wherein $R_3$ is hydrogen or a conventional protecting group for a carboxyl group and $R_4$ is hydrogen or $C_4$-$C_{10}$ tert-alkyl or a pharmaceutically acceptable salt thereof.

13. A pharmaceutical composition comprising an effective amount of an antibacterial compound of the formula

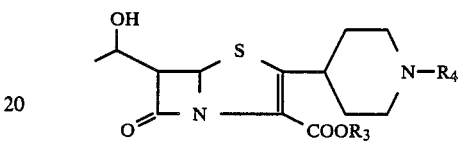

wherein $R_3$ is hydrogen or a conventional protecting group for a carboxyl group and $R_4$ is hydrogen or $C_4$-$C_{10}$ tert-alkyl or a pharmaceutically acceptable salt thereof.

14. A composition according to claim 13 adapted for oral administration.

15. A composition according to claim 13 adapted for parenteral administration.

16. A method of preventing bacterial infections in warm-blooded animals in need of said treatment which comprises administering thereto an antibacterial effective amount of a compound of the formula

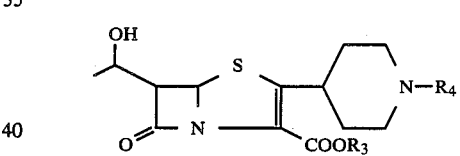

wherein $R_3$ is hydrogen or a conventional protecting group for a carboxyl group and $R_4$ is hydrogen or $C_4$-$C_{10}$ tert-alkyl or a pharmaceutically acceptable salt thereof.

* * * * *